(12) United States Patent
Hoogenboom

(10) Patent No.: US 9,631,017 B2
(45) Date of Patent: Apr. 25, 2017

(54) FAB FRAGMENT LIBRARIES AND METHODS FOR THEIR USE

(71) Applicant: Dyax Corp., Burlington, MA (US)

(72) Inventor: Hendricus Renerus Jacobus Mattheus Hoogenboom, Maastricht (NL)

(73) Assignee: Dyax Corp., Burlington, MA (US)

( * ) Notice: Subject to any disclaimer, the term of this patent is extended or adjusted under 35 U.S.C. 154(b) by 680 days.

(21) Appl. No.: 14/090,842

(22) Filed: Nov. 26, 2013

(65) Prior Publication Data

US 2014/0200165 A1 Jul. 17, 2014

Related U.S. Application Data

(60) Division of application No. 11/862,791, filed on Sep. 27, 2007, now abandoned, which is a continuation of application No. 09/988,899, filed on Nov. 19, 2001, now abandoned, which is a continuation of application No. PCT/US00/13682, filed on May 18, 2000.

(30) Foreign Application Priority Data

May 18, 1999 (EP) ..................... 99201558

(51) Int. Cl.
| | |
|---|---|
| C40B 50/06 | (2006.01) |
| C07K 16/26 | (2006.01) |
| C07K 16/00 | (2006.01) |
| C07K 16/18 | (2006.01) |

(52) U.S. Cl.
CPC .............. C07K 16/26 (2013.01); C07K 16/00 (2013.01); C07K 16/18 (2013.01); C07K 2317/55 (2013.01); C40B 50/06 (2013.01)

(58) Field of Classification Search
None
See application file for complete search history.

(56) References Cited

U.S. PATENT DOCUMENTS

| | | | |
|---|---|---|---|
| 5,427,908 A | 6/1995 | Dower et al. | |
| 5,658,727 A | 8/1997 | Barbas et al. | |
| 5,969,108 A | 10/1999 | McCafferty et al. | |

(Continued)

FOREIGN PATENT DOCUMENTS

| | | |
|---|---|---|
| EP | 0 844 306 | 5/1998 |
| EP | 0 866 136 | 9/1998 |
| WO | WO 90/14443 | 11/1990 |

(Continued)

OTHER PUBLICATIONS

Boeke et al., A prokaryotic membrane anchor sequence: carboxyl terminus of bacteriophage f1 gene III protein retains it in the membrane. Proc Natl Acad Sci U S A. Sep. 1982;79(17):5200-4.

(Continued)

Primary Examiner — Christian Boesen
(74) Attorney, Agent, or Firm — Wolf, Greenfield & Sacks, P.C.

(57) ABSTRACT

The present invention provides Fab libraries and methods for using the Fab libraries to obtain antibodies against a target. The Fab library of the invention contains at least $10^9$ different Fabs, and in some embodiments, at least $10^{10}$ different Fabs. The Fab libraries of the invention are used to isolate polyclonal or monoclonal Fabs that bind with high specificity to targets.

22 Claims, 8 Drawing Sheets

(56) References Cited

U.S. PATENT DOCUMENTS 6,172,197 B1    1/2001   McCafferty et al.

FOREIGN PATENT DOCUMENTS

WO    WO 92/01047    1/1992
WO    WO 94/05781    3/1994

OTHER PUBLICATIONS

Third party observations from EP Application Serial No. 09151233.5, dated Dec. 11, 2009.
[No Author Listed], "Cloning Vector" and "MCS" downloaded from Wikipedia; downloaded Mar. 3, 2007.
Andersson et al., A tandem repeat of MUC1 core protein induces a weak in vitro immune response in human B cells. Cancer Immunol Immunother. Jan. 1999;47(5):249-56.
Baecher-Allan et al., Generation of a polyclonal Fab phage display library to the protozoan parasite *Cryptosporidium parvum*. Comb Chem High Throughput Screen. Dec. 1999;2(6):319-25.
Barbas et al., Assembly of combinatorial antibody libraries on phage surfaces: the gene III site. Proc Natl Acad Sci U S A. Sep. 15, 1991;88(18):7978-82.
Davies et al., Characterisation of a recombinant Fv fragment of anti-MUC1 antibody HMFG1. Cancer Lett. Jul. 29, 1994;82(2):179-84.
De Haard et al., A large non-immunized human Fab fragment phage library that permits rapid isolation and kinetic analysis of high affinity antibodies. J Biol Chem. Jun. 25, 1999;274(26):18218-30.
Doleza et al., *Escherichia coli* expression of a bifunctional Fab-peptide epitope reagent for the rapid diagnosis of HIV-1 and HIV-2. Immunotechnology. Dec. 1995;1(3-4):197-209.
Fiorentini et al., Humanization of an antibody recognizing a breast cancer specific epitope by CDR-grafting. Immunotechnology. Mar. 1997;3(1):45-59.
Hoogenboom et al., Antibody phage display technology and its applications. Immunotechnology. Jun. 1998;4(1):1-20.
Huse et al., Generation of a large combinatorial library of the immunoglobulin repertoire in phage lambda. Science. Dec. 8, 1989;246(4935):1275-81.
McGuinness et al., Phage diabody repertoires for selection of large numbers of bispecific antibody fragments. Nat Biotechnol. Sep. 1996;14(9):1149-54.
Rader et al., Phage display of combinatorial antibody libraries. Curr Opin Biotechnol. Aug. 1997;8(4):503-8.
Siegel et al., Expression and characterization of recombinant anti-Rh(D) antibodies on filamentous phage: a model system for isolating human red blood cell antibodies by repertoire cloning. Blood. Apr. 15, 1994;83(8):2334-44.
EP 99201558, mailed Jan. 20, 2000, European Search Report.
PCT/US00/13682, mailed Sep. 6, 2000, International Search Report.
EP 09151233, mailed Mar. 8, 2010, European Search Report.

SCHEMATIC REPRESENTATION OF THE PHAGEMID VECTOR pCES1

Oligonucleotide primers used for construction of the library

A. Primary amplifications

IgM heavy chain constant region
HuIgMFOR    5'-TGG AAG AGG CAC GTT CTT TTC TTT-3' (SEQ ID NO:9)

κ light chain constant region
HuCkFOR     5'-ACA CTC TCC CCT GTT GAA GCT CTT-3' (SEQ ID NO:10)

λ light chain constant region
HuCl2-FOR   5'-TGA ACA TTC TGT AGG GGC CAC TG-3' (SEQ ID NO:11)
HuCl7-FOR   5'-AGA GCA TTC TGC AGG GGC CAC TG-3' (SEQ ID NO:12)

VH back
HuVH1B/7A-BACK   5'-CAG RTG CAG CTG GTG CAR TCT GG-3' (SEQ ID NO:13)
HuVH1C-BACK      5'-SAG GTC CAG CTG GTR CAG TCT GG-3' (SEQ ID NO:14)
HuVH2B-BACK      5'-CAG RTC ACC TTG AAG GAG TCT GG-3' (SEQ ID NO:15)
HuVH3B-BACK      5'-SAG GTG CAG CTG GTG GAG TCT GG-3' (SEQ ID NO:16)
HuVH3C-BACK      5'-GAG GTG CAG CTG GTG GAG WCY GG-3' (SEQ ID NO:17)
HuVH4B-BACK      5'-CAG GTG CAG CTA CAG CAG TGG GG-3' (SEQ ID NO:18)
HuVH4C-BACK      5'-CAG STG CAG CTG CAG GAG TCS GG-3' (SEQ ID NO:19)
HuVH5B-BACK      5'-GAR GTG CAG CTG GTG CAG TCT GG-3' (SEQ ID NO:20)
HuVH6A-BACK      5'-CAG GTA CAG CTG CAG CAG TCA GG-3' (SEQ ID NO:21)

B. Secondary amplifications

κ light chain constant region
HuCk-FOR-ASC

λ light chain constant region
HuCl2-FOR-ASC
HuCl7-FOR-ASC

VH back
HuVH1B/7A-BACK-SFI
HuVH1C-BACK-SFI
HuVH2B-BACK-SFI
HuVH3B-BACK-SFI
HuVH3C-BACK-SFI
HuVH4B-BACK-SFI
HuVH4C-BACK-SFI
HuVH5B-BACK-SFI
HuVH6A-BACK-SFI

FIG.2A

Oligonucleotide primers used for construction of the library

Vκ back
| | | |
|---|---|---|
| HuVk1B-BACK | 5'-GAC ATC CAG WTG ACC CAG TCT CC-3' | (SEQ ID NO:22) |
| HuVk2-BACK | 5'-GAT GTT GTG ATG ACT CAG ACT CAG TCT CC-3' | (SEQ ID NO:23) |
| HuVk3B-BACK | 5'-GAA ATT GTG WTG ACR CAG TCT CC-3' | (SEQ ID NO:24) |
| HuVk4B-BACK | 5'-GAT ATT GTG ATG ACC CAC ACT CC-3' | (SEQ ID NO:25) |
| HuVk5-BACK | 5'-GAA ACG ACA CTC ACG CAG TCT CC-3' | (SEQ ID NO:26) |
| HuVk6-BACK | 5'-GAA ATT GTG CTG ACT CAG TCT CC-3' | (SEQ ID NO:27) |

VH forward
HuJH1/2-FOR
HuJH3-FOR
HuJH4/5-FOR
HuJH6-FOR

Vκ back
HuVk1B-BACK-APA
HuVk2-BACK-APA
HuVk3B-BACK-APA
HuVk4B-BACK-APA
HuVk5-BACK-APA
HuVk6-BACK-APA

FIG.2B

Oligonucleotide primers used for construction of the library

| Vλ back | | Vλ back |
|---|---|---|
| HuVλ1A-BACK | 5'-CAG TCT GTG CTG ACT CAG CCA CC-3' (SEQ ID NO:28) | HuVλ1A-BACK-APA |
| HuVλ1B-BACK | 5'-CAG TCT GTG YTG ACG CAG CCG CC-3' (SEQ ID NO:29) | HuVλ1B-BACK-APA |
| HuVλ1C-BACK | 5'-CAG TCT GTC GTG ACG CAG CCG CC-3' (SEQ ID NO:30) | HuVλ1C-BACK-APA |
| HuVλ2-BACK | 5'-CAR TCT GCC CTG ACT CAG CCT-3' (SEQ ID NO:31) | HuVλ2-BACK-APA |
| HuVλ3A-BACK | 5'-TCC TAT GWG CTG ACT CAG CCA CC-3' (SEQ ID NO:32) | HuVλ3A-BACK-APA |
| HuVλ3B-BACK | 5'-TCT TCT GAG CTG ACT CAG GAC CC-3' (SEQ ID NO:33) | HuVλ3B-BACK-APA |
| HuVλ4-BACK | 5'-CAC GTT ATA CTG ACT CAA CCG CC-3' (SEQ ID NO:34) | HuVλ4-BACK-APA |
| HuVλ5-BACK | 5'-CAG GCT GTG CTG ACT CAG CCG TC-3' (SEQ ID NO:35) | HuVλ5-BACK-APA |
| HuVλ6-BACK | 5'-AAT TTT ATG CTG ACT CAG CCC CA-3' (SEQ ID NO:36) | HuVλ6-BACK-APA |
| HuVλ7/8-BACK | 5'-CAG RCT GTG GTG ACY CAG GAG CC-3' (SEQ ID NO:37) | HuVλ7/8-BACK-APA |
| HuVλ9-BACK | 5'-CWG CCT GTG CTG ACT CAG CCM CC-3' (SEQ ID NO:38) | HuVλ9-BACK-APA |

FIG.2C

Oligonucleotide primers used for construction of the library

5'-ACC GCC TCC ACC GGG CGC GCC TTA TTA ACA CTC TCC CCT GTT GAA GCT CTT-3' (SEQ ID NO:39)

5'-ACC GCC TCC ACC GGG CGC GCC TTA TTA TGA ACA TTC TGT AGG GGC CAC TG-3' (SEQ ID NO:40)
5'-ACC GCC TCC ACC GGG CGC GCC TTA TTA AGA GCA TTC TGC AGG GGC CAC TG-3' (SEQ ID NO:41)

5'-GTC CTC GCA ACT GCG GCC CAG CCG GCC ATG GCC CAG RTG CAG CTG GTG CAR TCT GG-3' (SEQ ID NO:42)
5'-GTC CTC GCA ACT GCG GCC CAG CCG GCC ATG GCC CAG SAG GTC CAG CTG GTR CAG TCT GG-3' (SEQ ID NO:43)
5'-GTC CTC GCA ACT GCG GCC CAG CCG GCC ATG GCC CAG RTC ACC TTG AAG GAG TCT GG-3' (SEQ ID NO:44)
5'-GTC CTC GCA ACT GCG GCC CAG CCG GCC ATG GCC SAG GTG CAG CTG GTG GAG TCT GG-3' (SEQ ID NO:45)
5'-GTC CTC GCA ACT GCG GCC CAG CCG GCC ATG GCC GAG GTG CAG CTG GTG GAG WCY GG-3' (SEQ ID NO:46)
5'-GTC CTC GCA ACT GCG GCC CAG CCG GCC ATG GCC CAG GTG CAG CTA CAG CAG TGG GG-3' (SEQ ID NO:47)
5'-GTC CTC GCA ACT GCG GCC CAG CCG GCC ATG GCC CAG STG CAG CTG CAG GAG TCS GG-3' (SEQ ID NO:48)
5'-GTC CTC GCA ACT GCG GCC CAG CCG GCC ATG GCC GAR GTG CAG CTG GTG CAG TCT GG-3' (SEQ ID NO:49)
5'-GTC CTC GCA ACT GCG GCC CAG CCG GCC ATG GCC CAG GTA CAG CTG CAG CAG TCA GG-3' (SEQ ID NO:50)

FIG.2D

Oligonucleotide primers used for construction of the library

5'-TGA GGA GAC GGT GAC CAG GGT GCC-3' (SEQ ID NO:51)
5'-TGA AGA GAC GGT GAC CAT TGT CCC-3' (SEQ ID NO:52)
5'-TGA GGA GAC GGT GAC CAG GGT TCC-3' (SEQ ID NO:53)
5'-TGA GGA GAC GGT GAC CGT GGT CCC-3' (SEQ ID NO:54)

5'-ACC GCC TCC ACC AGT GCA CTT GAC ATC CAG WTG ACC CAG TCT CC-3' (SEQ ID NO:55)
5'-ACC GCC TCC ACC AGT GCA CTT GAT GTT GTG ATG ACT CAG TCT CC-3' (SEQ ID NO:56)
5'-ACC GCC TCC ACC AGT GCA CTT GAA ATT GTG WTG ACR CAG TCT CC-3' (SEQ ID NO:57)
5'-ACC GCC TCC ACC AGT GCA CTT GAT ATT GTG ATG ACC CAC ACT CC-3' (SEQ ID NO:58)
5'-ACC GCC TCC ACC AGT GCA CTT GAA ACG ACA CTC ACG CAG TCT CC-3' (SEQ ID NO:59)
5'-ACC GCC TCC ACC AGT GCA CTT GAA ATT GTG CTG ACT CAG TCT CC-3' (SEQ ID NO:60)

FIG.2E

Oligonucleotide primers used for construction of the library

5'-ACC GCC TCC ACC AGT GCA CAG TCT GTG CTG ACT CAG CCA CC-3' (SEQ ID NO:61)
5'-ACC GCC TCC ACC AGT GCA CAG TCT GTG YTG ACG CAG CCG CC-3' (SEQ ID NO:62)
5'-ACC GCC TCC ACC AGT GCA CAG TCT GTC GTG ACG CAG CCG CC-3' (SEQ ID NO:63)
5'-ACC GCC TCC ACC AGT GCA CAR TCT GCC CTG ACT CAG CCT-3' (SEQ ID NO:64)
5'-ACC GCC TCC ACC AGT GCA CTT TCC TAT GWG CTG ACT CAG CCA CC-3' (SEQ ID NO:65)
5'-ACC GCC TCC ACC AGT GCA CTT TCT TCT GAG CTG ACT CAG GAC CC-3' (SEQ ID NO:66)
5'-ACC GCC TCC ACC AGT GCA CAC GTT ATA CTG ACT CAA CCG CC-3' (SEQ ID NO:67)
5'-ACC GCC TCC ACC AGT GCA CAG GCT GTG CTG ACT CAG CCG TC-3' (SEQ ID NO:68)
5'-ACC GCC TCC ACC AGT GCA CTT AAT TTT ATG CTG ACT CAG CCC CA-3' (SEQ ID NO:69)
5'-ACC GCC TCC ACC AGT GCA CAG RCT GTG GTG ACY CAG GAG CC-3' (SEQ ID NO:70)
5'-ACC GCC TCC ACC AGT GCA CWG CCT GTG CTG ACT CAG CCM CC-3' (SEQ ID NO:71)

FIG.2F

FAB FRAGMENT LIBRARIES AND METHODS FOR THEIR USE

CROSS-REFERENCE TO RELATED APPLICATIONS

This application is a divisional application of U.S. patent application Ser. No. 11/862,791, filed on Sep. 27, 2007, which is a continuation application of U.S. application Ser. No. 09/988,899, filed on Nov. 19, 2001, which is a continuation of international application no. PCT/US00/13682, filed on May 18, 2000 which claims priority to European application no. 99201558.6, filed on May 18, 1999. The contents of these applications are herein incorporated by reference in their entireties.

This invention relates in general to phage display libraries of human Fab fragments, and methods using the Fab fragment libraries to isolate high affinity antibodies. Especially, the invention relates to polynucleotides encoding a Fab library, Fab libraries, and methods for designing, constructing and selecting from Fab libraries.

Display on filamentous phage in combination with selection forms a powerful tool for the identification of peptide- or protein-based drugs (Winter et al., 1994; Clackson et al., 1994). Of these, antibodies are especially of interest, due to their capacity to recognize a variety of targets with high specificity and affinity. Particularly the use of partial or complete human antibodies, which elicit no or minimal immune response when administered to patients, is yielding an increasing list of FDA-approved protein-based drugs (Holliger et al. 1998). Phage display technology enables the generation of large repertoires of human antibodies (Marks et al., 1991, Hoogenboom et al., 1992; Griffiths et al., 1993; Vaughan et al., 1996), and biopanning procedures permit the selection of individual antibodies with a desired specificity.

Key to the success of the technology were two critical observations: (i) the expression of functional antibody fragments by secretion into the periplasm of *E. coli* (Better et al., 1988; Skerra et al., 1988), and, (ii) the rapid access to variable region gene pools by the polymerase chain reaction (Larrick et al., 1989; Ward et al., 1989; Marks et al., 1991). For the construction of antibody libraries, V-genes are amplified from B-cell cDNA and heavy and light chain genes are randomly combined and cloned to encode a combinatorial library of single-chain Fv (scFv) or Fab antibody fragments (Marks et al., 1991; Clackson et al. 1991; Persson et al., 1991; Orum et al., 1993). The natural primary (unselected) antibody repertoire within B-cells contains a large array of antibodies that recognize a variety of antigens; this array can be cloned as a 'naïve' repertoire of rearranged genes, by harvesting the V-genes from the IgM mRNA of B-cells of unimmunized human donors, isolated from peripheral blood lymphocytes (Marks et al., 1991), bone marrow or tonsils (Vaughan et al., 1996), or from similar animal sources (Gram et al., 1992). This procedure provides access to antibodies that have not yet encountered antigen, although the frequency of those genuine 'germline' antibodies will depend heavily on the source of B-cells (Klein et al., 1997). A single 'naïve' library, if sufficiently large and diverse, can indeed be used to generate antibodies to a large panel of antigens, including self, non-immunogenic and relatively toxic antigens (Griffiths et al., 1993; Marks et al., 1991). In a different approach, antibodies may be built artificially, by in vitro assembly of V-gene segments and D/J segments, yielding 'synthetic' antibodies (Hoogenboom et al., 1992). A major drawback of these procedures is that from the initial 'naive' and 'synthetic' libraries, only moderate affinity antibodies were isolated (Marks et al., 1991; Nissim et al., 1994). Over the last few years more efficient techniques have been developed to build larger libraries of antibody fragments, using sophisticated in vivo recombination methods (Griffiths et al., 1993) or brute force cloning procedures (Vaughan et al., 1996; Sheets et al., 1998). Such large libraries have yielded a greater number of human antibodies per antigen tested, with an average much higher affinity (up to sub-nanomolar). However, technical restrictions on the size of libraries that may be obtained or handled in selection, the loss of library diversity upon library amplification, and the relatively long down-stream analysis path of the selected antibodies, i.e., large scale affinity analysis, have limited the spread of these libraries as generic tools in antibody generation.

Most large libraries made to date use the single chain format for display on phage (Vaughan et al., 1996; Sheets et al. 1998). One report described the use of a human naive Fab library on phage (not permitting immediate screening of selected soluble Fab fragments) (Griffiths et al., 1994). scFv's have the tendency to form dimers and higher order multimers in a clone-dependent and relatively unpredictable way (Weidner, et al. 1992; Holliger, et al. 1993; Marks et al., 1993). As a consequence, the affinity assay used (such as BIAcore analysis) often necessitates purification of the selected antibody fragments. For example, ranking for off-rates using BIAcore is not easily possible with unpurified scFv fragments; the monomeric fraction of selected scFv clones first needs to be purified by affinity chromatography and gel-filtration (Sheets et al., 1998; Schier et al., 1996).

As was postulated and observed by Griffiths and colleagues (Griffiths et al., 1994), the size of the antibody library dictates the probability of the selection of high affinity antibodies to the antigen. Comparison of the first naVve scFv repertoire containing $2.9 \times 10^7$ clones (Marks et al., 1991), with a recently constructed scFv repertoire of approximately $10^{12}$ clones (Vaughan et al., 1996; Sheets et al. 1998), confirms this postulation: increasing the library size 500-fold resulted in approximately 100-fold higher affinities. This increase is caused by lowering the off-rates from $10^{-1}$-$10^{-2}$ s$^{-1}$ for fragments selected from the smaller sized library to $10^3$-$10^{-4}$ s$^{-1}$ for those from the larger library.

It is an object of the invention to create a Fab library that is a valuable source of antibodies for many different targets, and which will play a vital role in target discovery and validation in the area of functional genomics.

The invention provides a plurality of polynucleotides encoding a Fab library comprising a plurality of vector wherein the vector comprises:

a first and second cloning region, wherein
each cloning region comprises at least one, for the vector unique, restriction enzyme cleavage site,
each cloning region being 5' flanked by a ribosome binding site and a signal sequence,
a polynucleotide encoding an anchor region, located 3' of the second cloning region,
a first and a second plurality of variable polynucleotides,
each encoding a complete antibody variable region or part of an antibody variable region, possibly followed by a complete antibody constant region or part of an antibody constant region,
the first plurality of variable polynucleotides being cloned into the vector at the restriction enzyme cleavage site(s) of the first cloning region,
the second plurality of variable polynucleotides being cloned into the vector at the restriction enzyme cleavage site(s) of the second cloning region.

It is to be understood that the term "for the vector unique restriction enzyme cleavage site" refers to the presence of one of such a restriction site in the vector sequence, without taking into account the possible presence of such a site on the above-mentioned first and/or second polynucleotides encoding a complete antibody variable region or part of an antibody variable region, possibly followed by a complete antibody constant region or part of an antibody constant region. The said first and second polynucleotides may comprise restriction sites identical to the "unique" site. This means that the said restriction site was "unique" before both first and second polynucleotide sequences were cloned into the vector.

The first and second variable polynucleotides are preferably cloned in the cloning region in a predetermined orientation. Therefore, in case the cloning region comprises a single unique restriction site, this site is preferably of such a type that non-identical restriction ends are generated, such as e.g, generated by the restriction enzyme SfiI. However, the cloning region may comprise two or more unique restriction sites, so that the variable polynucleotides can be conveniently cloned as a restriction fragment that has the corresponding ends.

Preferably, in the vector according to the invention, the first and second cloning regions, both ribosomal binding sites, signal sequences and the anchor sequence are part of a single polylinker sequence. Both cloning regions may therefore be part of a single cassette, comprising the first cloning region, 5' flanked by a ribosomal binding site and a signal sequence, lying adjacent to the second cloning region, also 5' flanked by its corresponding ribosomal binding site and a signal sequence, and 3' flanked by the anchor sequence.

Preferably, the first plurality of variable polynucleotides are $V_L$ polynucleotides, and the second plurality of variable polynucleotides are $V_H$ polynucleotides. More preferably, the $V_L$ polynucleotides are $V_6$ polynucleotides, $V_6C_6$ polynucleotides, $V_8$ polynucleotides, $V_8C_8$ polynucleotides, a mixture of $V_6$ and $V_8$ polynucleotides, or a mixture of $V_6C_6$ and $V_8C_8$ polynucleotides.

In another embodiment of the polynucleotides according to the invention, the vector further comprises a tag for purification or detection of an antibody, said tag for purification of the antibody preferably comprising a poly-histidine tail; the tag for detection of the antibody is preferably a c-myc-derived tag.

In another embodiment of the polynucleotides according to the invention, the vector further comprises an amber stop codon located between the second variable polynucleotide and the anchor protein.

In still another embodiment of the polynucleotides according to the invention, the vector further comprises a $C_{H1}$ domain located between the second variable polynucleotide and the anchor protein, the $C_{H1}$ domain preferably being a human gamma-1 $C_{H1}$ domain.

"Anchor protein" is defined as a protein or part thereof that can at least partially be accomodated in the outer coat of a particle generated by an organism expressing the library, such as a phage or virus particle, or in the outer coat of an organism itself, in case the organism itself expresses the library. The outer coat is herein defined as the structure of a cell, virus or phage particle defining the outer surface thereof. In case of a phage or phagemid expressing the library, the anchor protein may be a coat protein, such as the gene III product. However, other systems, known to the skilled person, may be used to obtain a library according to the present invention. Therefore, e.g., transmembrane proteins, or the transmembrane domain thereof, may be contemplated to be used as anchor protein in eukaryotic expression systems. In the invention, the anchor protein may be fused to an antibody variable region or part thereof, resulting in the presentation of the said variable region to the outer environment of the organism, the region being anchored in its outer coat. In a preferred embodiment of the polynucleotides according to the invention, the anchor protein is a minor coat protein III of a filamentous phage $f_d$.

In one embodiment of the invention, the polynucleotides according to the invention, and therefore the Fab library, encodes at least $10^9$ different Fabs. In another embodiment of the invention, the Fab library of the invention encodes at least $10^{10}$ different Fabs. In still another embodiment of the invention, the Fab library encodes at least $3.7 \times 10^{10}$ different Fabs. In still another embodiment of the invention, the Fab library encodes $10^9$ to $3.7 \times 10^{10}$ different Fabs.

Further, the invention provides a Fab library, comprising
a plurality of vectors as defined above,
the second cloning region in each vector forming a fusion polynucleotide encoding a plurality of fusion proteins,
a plurality of capsid particles, wherein the plurality of vector containing the first and second pluralities of variable polynucleotides is packaged into the capsid particles, wherein
at least some of the capsid particles display the fusion protein encoded by the vector packaged into the capsid on the surface of the capsid.

Further the invention relates to a method of making a plurality of polynucleotides encoding a Fab library, comprising the steps of:
amplifying a first plurality of variable polynucleotides with a first set of primers,
amplifying a second plurality of variable polynucleotides with a second set of primers,
wherein each set of primers comprises oligonucleotides designed to be homologous to the 5' and 3' end of variable polynucleotides encoding antibody variable regions or parts thereof, such that they can be used to amplify variable polynucleotide pools from natural or synthetic sources of genes while retaining all or part of the antibody's antigen combining site;
cloning the first and second plurality of variable polynucleotides into a plurality of vectors,
wherein the vector comprises:
a first and a second cloning region, wherein
each cloning region comprises at least one, for the vector unique, restriction enzyme cleavage site,
each cloning region being 5' flanked by a ribosome binding site and a signal sequence,
a polynucleotide encoding an anchor region, located 3' of the second cloning region,
wherein the first plurality of variable polynucleotides is cloned into the restriction enzyme cleavage site(s) of the first cloning region of the vector and the second plurality of variable polynucleotides into the restriction enzyme cleavage site(s) of the second cloning region of the vector.

In one embodiment, the method of constructing the Fab library comprises the steps of: amplifying a plurality of variable gene pools with a set of the primers, wherein the primers comprise oligonucleotides designed to be homologous to the 5' and 3' end of variable polynucleotides encoding antibody variable regions or parts thereof, such that they can be used to amplify variable polynucleotide pools from natural or synthetic sources of genes while retaining all or part of the antibody's antigen combining site; cloning the amplified variable gene pools into a vector with a two-step procedure to obtain a Fab library; wherein the vector comprises a phage or phagemid vector which will accommodate expression of the cloned antibody variable polynucleotides as antibody Fab fragments, wherein one of the two antibody chains is fused to one of the phage coat proteins (e.g., geneIII product).

In one embodiment, the BACK primers were designed to have at the most three mutations in a total of twentyone to twentythree nucleotides when compared to the human germline gene segment region they would have to bind to, but with at least 3 homologous residues towards the 3' site of the oligonucleotide. This set of olignucleotides will recognise approximately 90% of human germline gene segments and as such provide access to most of the present diversity of the B-cells in non-immunized sources. In another embodiment, the heavy chain primers should end with 'GG' to ensure stable binding at high annealing temperatures (at least 55EC). Similarly the VkappaBACK primers and most of the VlambdaBACK primers will be designed to preferentially end in 'CC'. In an alternate embodiment, the primers consist of the sequences in FIG. 2.

The invention also provides methods for obtaining antibodies specific to an antigen from the Fab library. In certain embodiments, the methods of the invention allow a rapid initial screen of off-rates using the Fab libraries of the invention. In alternate embodiments, the methods of the patent are used to screen off-rates for a large series of antigen specific Fabs using the Fab libraries of the invention.

The present invention also relates to isolated antibodies specific to an antigen of choice, and their corresponding nucleic acids, that are isolated from the Fab libraries of the invention. In an alternative embodiment, these isolated antibodies are high affinity antibodies. The antibodies may be used as research reagents or as therapeutic products. The antibodies of the invention will be ideal for investigating the nature and localization of their targets, and the antibodies can be used to purify the target. Thus, the antibodies of the invention will be important for target validation and target discovery in the area of functional genomics.

The invention also relates to a vector as is defined above, comprising one of the first and one of the second plurality of the variable polynucleotides cloned into the first and second cloning region respectively.

The present invention further relates to host cells containing the Fab libraries of the invention or the polynucleotides that encode the Fab libraries of the invention.

In one aspect the invention involves linking the desired specific binding pair member, such as an antibody molecule, to a phage coat protein. By then enriching for the specific binding pair member, such as by affinity techniques, for example, the DNA which encodes the specific binding pair member is also enriched and may then be isolated. The DNA so obtained may then be cloned and expressed in other systems, yielding potentially large quantities of the desired specific binding pair member, or may be subjected to sequencing and further cloning and genetic manipulations prior to expression.

Typically the target for the specific binding pair member, e.g., an antigen or hapten when the specific binding pair member is an antibody, is known, and the methods herein provide a means for creating and/or identifying a specific binding pair member which specifically binds the target of interest. Thus, when the protein is an antibody the present invention provides a novel means for producing antibodies, particularly monoclonal antibodies, with specificity for pre- determined targets, thereby circumventing the laborious, time-consuming and often unpredictable process of conventional monoclonal antibody technology.

BRIEF DESCRIPTION OF THE DRAWINGS

FIG. 2A. lists oligonucleotide primers (SEQ ID Nos:9-21) used for construction of the library.

FIG. 2B. lists oligonucleotide primers (SEQ ID Nos:22-27) for construction of the library.

FIG. 2C. lists oligonucleotide primers (SEQ ID Nos:28-38) for construction of the library.

FIG. 2D. lists oligonucleotide primers (SEQ ID Nos:39-50) for construction of the library.

FIG. 2E. lists oligonucleotide primers (SEQ ID Nos:51-60) for construction of the library.

FIG. 2F. lists oligonucleotide primers (SEQ ID Nos:61-71) for construction of the library.

Figure 1A:
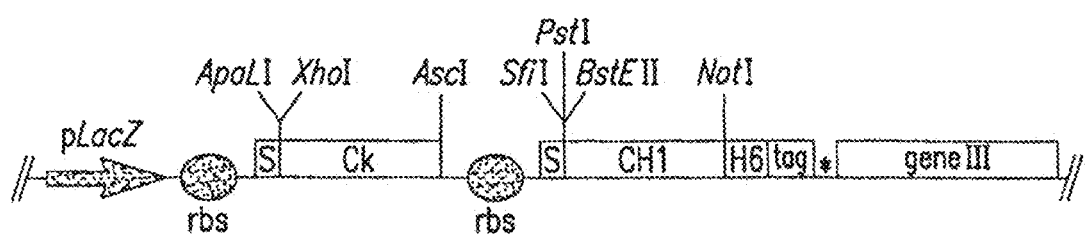
FIG. 1A. Phagemid vector pCES1 for display of antibody Fab fragments. Schematic representation (A) and polylinker region (SEQ ID NOS: 5-8) (B) of pCES1. The polylinker region comprises two signal sequences ('S'; pelB and the geneIII leader sequence), the C6 domain, ribosome binding site (rbs), CH1 domain, hexa histidine tag (H6) and a c-myc derived sequence. Variable domain genes can be cloned as ApaLI-XhoI or ApaLI-Asc fragments (for VL or VLCL respectively) and SfiI/PstI-BstEII or SfiI-NotI fragments (for VH or VHCH1 respectively. The amber stop codon (*) between the antibody genes and bacteriophage gene III enables the production of soluble Fab fragments in a non-suppressor strain of E. coli. Expression of the bicistronic operon is under control of the LacZ promotor (pLacZ).

The term "active" refers to those forms of the polypeptide which retain the biologic and/or immunologic activities of any naturally occurring polypeptide.

The term "activated" cells as used in this application are those which are engaged in extracellular or intracellular membrane trafficking, including the export of neurosecretory or enzymatic molecules as part of a normal or disease process.

The term 'antibody' means an immunoglobulin whether natural or partly or wholly synthetically produced. The term also covers any protein or polypeptide having a binding domain which is homologous to an immunoglobulin binding domain. These proteins can be derived from natural sources, or partly or wholly synthetically produced. Example antibodies are the immunoglobulin isotypes and the Fab, scFv, Fv, dAab, VHH, Fd fragments.

The term 'antibody polypeptide dimer' means an association of two polypeptide chain components of an antibody, capable of binding an antigen. Thus, it may be one arm of an antibody consisting of a heavy chain and a light chain, it may be a Fab fragment consisting of $V_L$, $V_H$, $C_L$ and $C_{H1}$ antibody domains, or an Fv fragment consisting of a $V_L$ domain and a $V_H$ domain.

The term 'capsid' means a replicable genetic display package, with or without the genetic information. The capsids display a member of a specific binding pair at its surface. The package may be a population of bacteriophages which display an antigen binding domain, e.g., a Fab, at the surface of some or all of the capsids within the population. This type of package has been called a phage antibody (pAb).

The term '$C_{H1}$ domain' means the first constant region of the heavy chain of an antibody or part thereof or extended with aminoacids from the hinge regions as to allow pairing of the expressed (VH)CH1 fragment with the antibody's light chain, and possible disulphide-bridge formation. This may be the CH1 domain of a human antibody of isotype gamma-1.

A "component part of an antibody antigen-binding site" may be or correspond to a polypeptide chain component, e.g., a $V_H$ or a $V_L$ domain. However, it may be a CDR, or a $V_L$ sequence plus CDR of a $V_H$, a $V_H$ sequence plus CDR of a $V_L$, a $V_H$ plus $V_L$ sequence lacking only a CDR, and so on. The proviso is that the first and second component parts of an antigen-binding site of an antibody must in combination (together) form an antigen-binding site. Thus, if the second component part of an antigen-binding site of a non-human antibody specific for an antigen of interest is a CDR, then the first component part of an antigen-binding site of a human antibody will comprise the remainder of a $V_H$ and $V_L$ region required to form a antigen-binding site (with or without associated antibody constant domains (in a Fab format), or with or without a linker peptide sequence (in a Fv format). The second component part of an antigen-binding site of a non-human antibody may comprise a $V_L$ domain plus part of a $V_H$ domain, that part being one or more CDRs, for instance, perhaps CDR3. In such case, the first component part of an antigen-binding site of a human antibody would comprise the remainder of a $V_H$ sequence which in combination with the second component part forms an antigen-binding site. Of course, the converse situation holds and the person skilled in the art will be able to envisage other combinations of first and second component parts which together form an antigen-binding site.

The term 'conditionally defective' means a gene which does not express a particular polypeptide under one set of conditions, but expresses it under another set of conditions. An example, is a gene containing an amber mutation expressed in non-suppressing or suppressing hosts respectively. Alternatively, a gene may express a protein or polypeptide which is defective under one set of conditions, but not under another set. An example is a gene with a temperature sensitive mutation.

The term "derivative" refers to polypeptides chemically modified by such techniques as ubiquitination, labeling (e.g., with radionuclides or various enzymes), pegylation (derivatization with polyethylene glycol) and insertion or substitution by chemical synthesis of amino acids such as ornithine, which do not normally occur in human proteins.

The term 'domain' means a part of a protein or polypeptide that is folded within itself and independently of other parts of the same protein or polypeptide and independently of a complementary binding member.

The term 'eluant' means a solution used to breakdown the linkage between two molecules. The linkage can be a non-covalent or covalent bond(s). The two molecules can be members of a sbp.

The term 'expression modulating fragment,' EMF, means a series of nucleotides which modulates the expression of an operably linked ORF or another EMF.

As used herein, a sequence is said to 'modulate the expression of an operably linked sequence' when the expression of the sequence is altered by the presence of the EMF. EMFs include, but are not limited to, promoters, and promoter modulating sequences (inducible elements). One class of EMFs are fragments which induce the expression or an operably linked ORF in response to a specific regulatory factor or physiological event.

The term "Fab" refers to antibody fragments including fragments which comprise two N-terminal portions of the heavy chain polypeptide joined by at least one disulfide bridge in the hinge region and two complete light chain polypeptides, where each light chain is complexed with one N-terminal portion of a heavy chain. Fab also includes Fab fragments which comprise all or a large portion of a light chain polypeptide (e.g., $V_L C_L$) complexed with the N-terminal portion of a heavy chain polypeptide (e.g., $V_H C_{H1}$).

The term "Fab library" refers to a collection of Fab polynucleotide sequences within clones; or a genetically diverse collection of Fab polypeptides displayed on rgdps capable of selection or screening to provide an individual Fab polypeptide or a mixed population of Fab polypeptides.

The term 'folded unit' means a specific combination of an alpha-helix and/or beta-strand and/or beta-turn structure. Domains and folded units contain structures that bring together amino acids that are not adjacent in the primary structure.

The term 'genetically diverse population' means antibodies or polypeptide components thereof, this is referring not only to diversity that can exist in the natural population of cells or organisms, but also diversity that can be created by artificial mutation in vitro or in vivo. Mutation in vitro may for example, involve random mutagenesis using oligonucleotides having random mutations of the sequence desired to be varied. In vivo mutagenesis may for example, use mutator strains of host microorganisms to harbour the DNA (see Example 38 of WO 92/01047). The words "unique population" may be used to denote a plurality of e.g., polypeptide chains, which are not genetically diverse i.e., they are all the same. A restricted population is one which is diverse but less so than the full repertoire of an animal. The diversity may have been reduced by prior selection, e.g., using antigen binding specificity.

The term 'helper phage' means a phage which is used to infect cells containing a defective phage genome and which functions to complement the defect. The defective phage genome can be a phagemid or a phage with some function encoding gene sequences removed. Examples of helper phages are M13KO7, M13K07 gene III no. 3; and phage displaying or encoding a binding molecule fused to a capsid protein.

The term 'homologs' means polypeptides having the same or conserved residues at a corresponding position in their primary, secondary or tertiary structure. The term also extends to two or more nucleotide sequences encoding the homologous polypeptides. Example homologous peptides are the immunoglobulin isotypes.

The term "host cell" refers to a prokaryotic or eukaryotic cell into which the vectors of the invention may be introduced, expressed and/or propagated. Typical prokaryotic host cells include various strains of *E. coli*. Typical eukaryotic host cells are yeast or filamentous fungi, or mammalian cells, such as Chinese hamster ovary cells, murine NIH 3t3 fibroblasts, or human embryonic kidney 193 cells.

The term 'immunoglobulin superfamily' means a family of polypeptides, the members of which have at least one domain with a structure related to that of the variable or constant domain of immunoglobulin molecules. The domain contains two B-sheets and usually a conserved disulphide bond (see A. F. Williams and A. N. Barclay 1988 Ann. Rev Immunol. 6 381-405). Example members of an immunoglobulin superfamily are CD4, platelet derived growth factor receptor (PDGFR), intercellular adhesion molecule. (ICAM). Except where the context otherwise dictates, reference to immunoglobulins and immunoglobulin homologs in this application includes members of the immunoglobulin superfamily and homologs thereof.

The term "infection" refers to the introduction of nucleic acids into a suitable host cell by use of a virus or viral vector.

The term "intermediate fragment" means a nucleic acid between 5 and 1000 bases in length, and preferably between 10 and 40 bp in length.

The term "isolated" as used herein refers to a nucleic acid or polypeptide separated not only from other nucleic acids or polypeptides that are present in the natural source of the nucleic acid or polypeptide, but also from polypeptides, and preferably refers to a nucleic acid or polypeptide found in the presence of (if anything) only a solvent, buffer, ion, or other component normally present in a solution of the same. The terms "isolated" and "purified" do not encompass nucleic acids or polypeptides present in their natural source.

The term 'mutator strain' means a host cell which has a genetic defect which causes DNA replicated within it to be mutated with respect to its parent DNA. Example mutator strains are NR9046mutD5 and NR9046 mut T1 (See Example 38 of WO 92/01047).

The term "naturally occurring polypeptide" refers to polypeptides produced by cells that have not been genetically engineered and specifically contemplates various polypeptides arising from post-translational modifications of the polypeptide including, but not limited to, acetylation, carboxylation, glycosylation, phosphorylation, lipidation and acylation.

The term 'nucleotide sequence' refers to a heteropolymer of nucleotides or the sequence of these nucleotides. The terms 'nucleic acid' and 'polynucleotide' are also used interchangeably herein to refer to a heteropolymer of nucleotides. Generally, nucleic acid segments provided by this invention may be assembled from fragments of the genome and short oligonucleotide linkers, or from a series of oligonucleotides, or from individual nucleotides, to provide a synthetic nucleic acid which is capable of being expressed in a recombinant transcriptional unit comprising regulatory elements derived from a microbial or viral operon, or a eukaryotic gene.

The terms "oligonucleotide fragment" or a "polynucleotide fragment", "portion," or "segment" is a stretch of polypeptide nucleotide residues which is long enough to use in polymerase chain reaction (PCR) or various hybridization procedures to identify or amplify identical or related parts of mRNA or DNA molecules.

The terms "oligonucleotides" or "nucleic acid probes" are prepared based on the polynucleotide sequences provided in the present invention. Oligonucleotides comprise portions of such a polynucleotide sequence having at least about 15 nucleotides and usually at least about 20 nucleotides. Nucleic acid probes comprise portions of such a polynucleotide sequence having fewer nucleotides than about 6 kb, usually fewer than about 1 kb. After appropriate testing to eliminate false positives, these probes may, for example, be used to determine whether specific mRNA molecules are present in a cell or tissue or to isolate similar nucleic acid sequences from chromosomal DNA as described by Walsh et al. (Walsh, P. S. et al., 1992, PCR Methods Appl 1:241-250).

The term "open reading frame," ORF, means a series of nucleotide triplets coding for amino acids without any termination codons and is a sequence translatable into protein.

The term 'phage vector' means a vector derived by modification of a phage genome, containing an origin of replication for a bacteriophage, but not one for a plasmid.

The term 'phagemid vector' means a vector derived by modification of a plasmid genome, containing an origin of replication for a bacteriophage as well as the plasmid origin of replication.

The term "phenotype" refers to a physical (e.g., pigment, or cell shape) and/or metabolic property of a cell which can be measured or exploited in some fashion and which is effected by the reporter gene.

The term 'polylinker region' means a polynucleotide that contains at least two restriction enzyme sites that are unique in the vector that contains the polylinker region, i.e., these restriction sites are easily used cloning sites in the vector.

A polypeptide "fragment," "portion," or "segment" is a stretch of amino acid residues of at least about 5 amino acids, often at least about 7 amino acids, typically at least about 9 to 13 amino acids, and, in various embodiments, at least about 17 or more amino acids. To be active, any polypeptide must have sufficient length to display biologic and/or immunologic activity.

The term "probes" includes naturally occurring or recombinant or chemically synthesized single- or double-stranded nucleic acids. They may be labeled by nick translation, Klenow fill-in reaction, PCR or other methods well known in the art. Probes of the present invention, their preparation and/or labeling are elaborated in Sambrook, J. et al., 1989, Molecular Cloning: A Laboratory Manual, Cold Spring Harbor Laboratory, NY; or Ausubel, F. M. et al., 1989, Current Protocols in Molecular Biology, John Wiley & Sons, New York N.Y., both of which are incorporated herein by reference in their entirety.

The term "purified" as used herein denotes that the indicated nucleic acid or polypeptide is present in the substantial absence of other biological macromolecules, e.g., polynucleotides, proteins, and the like. In one embodiment, the polynucleotide or polypeptide is purified such that it constitutes at least 95% by weight, more preferably at least 99.8% by weight, of the indicated biological macromolecules present (but water, buffers, and other small molecules, especially molecules having a molecular weight of less than 1000 daltons, can be present).

The term "recombinant," when used herein to refer to a polypeptide or protein, means that a polypeptide or protein is derived from recombinant (e.g., microbial or mammalian) expression systems. 'Microbial' refers to recombinant polypeptides or proteins made in bacterial or fungal (e.g., yeast) expression systems. As a product, 'recombinant microbial' defines a polypeptide or protein essentially free of native endogenous substances and unaccompanied by associated native glycosylation. Polypeptides or proteins expressed in most bacterial cultures, e.g., *E. coli*, will be free of glycosylation modifications; polypeptides or proteins expressed in yeast will have a glycosylation pattern in general different from those expressed in mammalian cells.

The term 'recombinant expression vehicle or vector' refers to a plasmid or phage or virus or vector, for expressing a polypeptide from a DNA (RNA) sequence. An expression vehicle can comprise a transcriptional unit comprising an assembly of (1) a genetic element or elements having a regulatory role in gene expression, for example, promoters or enhancers, (2) a structural or coding sequence which is transcribed into mRNA and translated into protein, and (3) appropriate transcription initiation and termination sequences. Structural units intended for use in yeast or eukaryotic expression systems preferably include a leader sequence enabling extracellular secretion of translated protein by a host cell. Alternatively, where recombinant protein is expressed without a leader or transport sequence, it may include an N-terminal methionine residue. This residue may or may not be subsequently cleaved from the expressed recombinant protein or polypeptide to provide a final product.

The term "recombinant expression system" means host cells which have stably integrated a recombinant transcriptional unit into chromosomal DNA or carry the recombinant transcriptional unit extrachromosomally. Recombinant expression systems as defined herein will express heterologous polypeptides or proteins upon induction of the regulatory elements linked to the DNA segment or synthetic gene to be expressed. This term also means host cells which have stably integrated a recombinant genetic element or elements having a regulatory role in gene expression, for example, promoters or enhancers. Recombinant expression systems as defined herein will express polypeptides or proteins endogenous to the cell upon induction of the regulatory elements linked to the endogenous DNA segment or gene to be expressed. The cells can be prokaryotic or eukaryotic.

The term "recombinant variant" refers to any polypeptide differing from naturally occurring polypeptides by amino acid insertions, deletions, and substitutions, created using recombinant DNA techniques. Guidance in determining which amino acid residues may be replaced, added or deleted without abolishing activities of interest, such as cellular trafficking, may be found by comparing the sequence of the particular polypeptide with that of homologous peptides and minimizing the number of amino acid sequence changes made in regions of high homology.

Preferably, amino acid "substitutions" are the result of replacing one amino acid with another amino acid having similar structural and/or chemical properties, i.e., conservative amino acid replacements. Amino acid substitutions may be made on the basis of similarity in polarity, charge, solubility, hydrophobicity, hydrophilicity, and/or the amphipathic nature of the residues involved. For example, nonpolar (hydrophobic) amino acids include alanine, leucine, isoleucine, valine, proline, phenylalanine, tryptophan, and methionine; polar neutral amino acids include glycine, serine, threonine, cysteine, tyrosine, asparagine, and glutamine; positively charged (basic) amino acids include arginine, lysine, and histidine; and negatively charged (acidic) amino acids include aspartic acid and glutamic acid.

"Insertions" or "deletions" are typically in the range of about 1 to 5 amino acids. The variation allowed may be experimentally determined by systematically making insertions, deletions, or substitutions of amino acids in a polypeptide molecule using recombinant DNA techniques and assaying the resulting recombinant variants for activity.

Alternatively, where alteration of function is desired, insertions, deletions or non-conservative alterations can be engineered to produce altered polypeptides. Such alterations can, for example, alter one or more of the biological functions or biochemical characteristics of the polypeptides of the invention. For example, such alterations may change polypeptide characteristics such as ligand-binding affinities, interchain affinities, or degradation/turnover rate. Further, such alterations can be selected so as to generate polypeptides that are better suited for expression, scale up and the like in the host cells chosen for expression. For example, cysteine residues can be deleted or substituted with another amino acid residue in order to eliminate disulfide bridges.

Alternatively, recombinant variants encoding these same or similar polypeptides may be synthesized or selected by making use of the "redundancy" in the genetic code. Various codon substitutions, such as the silent changes which produce various restriction sites, may be introduced to optimize cloning into a plasmid or viral vector or expression in a particular prokaryotic or eukaryotic system. Mutations in the polynucleotide sequence may be reflected in the polypeptide or domains of other peptides added to the polypeptide to modify the properties of any part of the polypeptide, to change characteristics such as ligand-binding affinities, interchain affinities, or degradation/turnover rate.

The term 'repertoire of artificially rearranged immunoglobulin genes' means a collection of nucleotide e.g., DNA, sequences derived wholly or partly from a source other than the rearranged immunoglobulin sequences from an animal. This may include for example, DNA sequences encoding VH domains by combining unrearranged V segments with D and J segments and DNA sequences encoding VL domains by combining V and J segments. Part or all of the DNA sequences may be derived by oligonucleotide synthesis.

The term 'repertoire of rearranged immunoglobulin genes' means a collection of naturally occurring nucleotides e.g., DNA sequences which encoded expressed immunoglobulin genes in an animal. The sequences are generated by the in vivo rearrangement of e.g., V, D and J segments for H chains and e.g., the V and J segments for L chains. Alternatively the sequences may be generated from a cell line immunised in vitro and in which the rearrangement in response to immunisation occurs intracellularly. The word "repertoire" is used to indicate genetic diversity.

The term 'replicable genetic display package' (Rgdp) means a biological particle which has genetic information providing the particle with the ability to replicate. The particle can display on its surface at least part of a polypeptide. The polypeptide can be encoded by genetic information native to the particle and/or artificially placed into the particle or an ancestor of it. The displayed polypeptide may be any member of a specific binding pair e.g., heavy or light chain domains based on an immunoglobulin molecule, an enzyme or a receptor etc. The particle may be a virus e.g., a bacteriophage such as fd or M13.

The term "reporter gene" refers to a nucleic acid which encodes a protein or polypeptide that produces a phenotypic change in the host cell that may be measured and/or used to separate host cells. For example, the reporter gene may encode a protein or polypeptide that has flourescent properties, e.g., β-galactosidase, auto-fluorescent protein GFP, etc.; or the reporter gene may encode a selectable marker, e.g., antibiotic resistance; or an epitope that is expressed on the surface of the host cell.

The term 'ribosome binding site' means a polyribonucleotide that allows a ribosome to select the proper initiation codon during the initiation of translation. In some prokaryotes, this polyribonucleotide is called the Shine-Dalgarno sequence, and the Shine-Delgarno sequence base pairs with the 16S RNA of the ribosome.

The term "secreted" protein or polypeptide refers to a protein or polypeptide that is transported across or through a membrane, including transport as a result of signal sequences in its amino acid sequence when it is expressed in a suitable host cell. "Secreted" proteins or polypeptides include without limitation proteins or polypeptides secreted wholly (e.g., soluble proteins) or partially (e.g., receptors) from the cell in which they are expressed. "Secreted" proteins or polypeptides also include without limitation proteins or polypeptides which are transported across the membrane of the endoplasmic reticulum.

The term 'signal sequence' means an amino acid sequence that is found at the amino terminus of a polypeptide and directs transportation of the polypeptide across or through a membrane. Signal sequences include amino terminal polypeptides that are 13-36 residues long, and have a 7 to 13 residue hydrophobic core flanked by several hydrophilic residues that usually include one or more basic residues near the N-terminus.

The term "stringent" is used to refer to conditions that are commonly understood in the art as stringent. An exemplary set of conditions include a temperature of 60-70° C., (preferably about 65° C.) and a salt concentration of 0.70 M to 0.80 M (preferably about 0.75M). Further exemplary conditions include, hybridizing conditions that (1) employ low ionic strength and high temperature for washing, for example, 0.015 M NaCl/0.0015 M sodium citrate/0.1% SDS at 50° C.; (2) employ during hybridization a denaturing agent such as formamide, for example, 50% (vol/vol) formamide with 0.1% bovine serum albumin/0.1% Ficoll/0.1% polyvinylpyrrolidone/50 mM sodium phosphate buffer at pH 6.5 with 750 mM NaCl, 75 mM sodium citrate at 42° C.; or (3) employ 50% formamide, 5×SSC (0.75 M NaCl, 0.075 M Sodium pyrophosphate, 5×Denhardt's solution, sonicated salmon sperm DNA (50 g/ml), 0.1% SDS, and 10% dextran sulfate at 42° C., with washes at 42° C. in 0.2×SSC and 0.1% SDS.

In instances wherein hybridization of deoxyoligonucleotides is concerned, additional exemplary stringent hybridization conditions include washing in 6×SSC/0.05% sodium pyrophosphate at 37EC (for 14-base oligos), 48EC (for 17-base oligos), 55EC (for 20-base oligos), and 60EC (for 23-base oligos).

As used herein, "substantially equivalent" can refer both to nucleotide and amino acid sequences, for example a mutant sequence, that varies from a reference sequence by one or more substitutions, deletions, or additions, the net effect of which does not result in an adverse functional dissimilarity between the reference and subject sequences. Typically, such a substantially equivalent sequence varies from one of those listed herein by no more than about 20% (i.e., the number of individual residue substitutions, additions, and/or deletions in a substantially equivalent sequence, as compared to the corresponding reference sequence, divided by the total number of residues in the substantially equivalent sequence is about 0.2 or less). Such a sequence is said to have 80% sequence identity to the listed sequence. In one embodiment, a substantially equivalent, e.g., mutant, sequence of the invention varies from a listed sequence by no more than 10% (90% sequence identity); in a variation of this embodiment, by no more than 5% (95% sequence identity); and in a further variation of this embodiment, by no more than 2% (98% sequence identity). Substantially equivalent, e.g., mutant, amino acid sequences according to the invention generally have at least 95% sequence identity with a listed amino acid sequence, whereas substantially equivalent nucleotide sequence of the invention can have lower percent sequence identities, taking into account, for example, the redundancy or degeneracy of the genetic code. For the purposes of the present invention, sequences having substantially equivalent biological activity and substantially equivalent expression characteristics are considered substantially equivalent. For the purposes of determining equivalence, truncation of the mature sequence (e.g., via a mutation which creates a spurious stop codon) should be disregarded.

Nucleic acid sequences encoding such substantially equivalent sequences, e.g., sequences of the recited percent identities, can routinely be isolated and identified via standard hybridization procedures well known to those of skill in the art.

The term 'suppressible translational stop codon' means a codon which allows the translation of nucleotide sequences downstream of the codon under one set of conditions, but under another set of conditions translation ends at the codon. Example of suppressible translational stop codons are the amber, ochre and opal codons.

The term 'tag' means an extension of the antibody Fab fragment, for example expressed at the carboxyterminus of the heavy chain, that comprises at least one amino acids but more typically five to fifteen amino acids, and that can be specifically recognised by an antibody or other binding ligand or binding matrix for the sequence. Tags may be combined in the same Fab. Examples are a stretch of five histidine residues that can be recognised by specific antibodies and by defined immobilised metal ions, and a stretch of the following 12 amino acids (EQKLISEEDLN) that are recognised by the 9E10 antibody (Marks et al., 1991).

The term 'target' means any molecule that is antigenic, e.g., can be recognized with reasonably specificity by an antibody from the Fab library.

The term 'target element' refers to a nucleic acid sequence that alters the expression of the target gene. Target elements include, but are not limited to, promoters, and promoter modulating sequences (inducible elements). One class of target elements are fragments which induce the expression in response to a specific regulatory factor or physiological event.

The term "transfection" refers to the taking up of an expression vector by a suitable host cell, whether or not any coding sequences are in fact expressed.

The term "transformation" means introducing DNA into a suitable host cell so that the DNA is replicable, either as an extrachromosomal element, or by chromosomal integration.

The term "universal set" refers to a set of nucleic acids, most preferably a set of oligonucleotides, which represent all possible combinations of sequence for a given length of nucleotides, e.g., all 4096 insert oligonucleotides six nucleotides in length. In a preferred embodiment, the term universal set refers to the set of all possible oligonucleotides of a given length, wherein one or more positions in the oligonucleotides are held constant (i.e., the same nucleotide is present at this position in all members of the set).

As used herein, an 'uptake modulating fragment,' UMF, means a series of nucleotides which mediate the uptake of a linked DNA fragment into a cell. UMFs can be readily identified using known UMFs as a target sequence or target motif with the computer-based systems described below.

The presence and activity of a UMF can be confirmed by attaching the suspected UMF to a marker sequence. The resulting nucleic acid molecule is then incubated with an appropriate host under appropriate conditions and the uptake of the marker sequence is determined. As described above, a UMF will increase the frequency of uptake of a linked marker sequence.

The term 'vector' refers to a plasmid or phage or virus or vector, for expressing a polypeptide from a DNA (RNA) sequence. The vector can comprise a transcriptional unit comprising an assembly of (1) a genetic element or elements having a regulatory role in gene expression, for example, promoters or enhancers, (2) a structural or coding sequence which is transcribed into mRNA and translated into protein, and (3) appropriate translation initiation and termination sequences. Structural units intended for use in yeast or eukaryotic expression systems may include a leader sequence enabling extracellular secretion of translated protein by a host cell.

The term 'V$_L$ polynucleotides' means polynucleotides encoding the CDR containing domains of some or all of the light chain genes from the V$_6$- and/or V$_8$-families.

The term 'V$_H$ polynucleotides' means polynucleotides encoding the CDR containing domains of some or all of the heavy chain genes from the heavy chain gene family.

Each of the above terms is meant to encompasses all that is described for each, unless the context dictates otherwise.

The recombinant constructs of the present invention comprise a vector, such as a plasmid or viral vector, into which a nucleic acid(s) of interest may be inserted. The vector may further comprise regulatory sequences, including for example, a promoter, operably linked to the nucleic acid(s) of interest. Large numbers of suitable vectors and promoters are known to those of skill in the art and are commercially available for generating the recombinant constructs of the present invention. The following vectors are provided by way of example. Bacterial: pBs, phagescript, PsiX174, pBluescript SK, pBs KS, pNH8a, pNH16a, pNH18a, pNH46a (Stratagene); pTrc99A, pKK223-3, pKK233-3, pDR540, pRIT5 (Pharmacia). Eukaryotic: pWLneo, pSV2cat, pOG44, PXTI, pSG (Stratagene) pSVK3, pBPV, pMSG, pSVL (Pharmacia).

Methods which are well known to those skilled in the art can be used to construct vectors containing a polynucleotide of the invention and appropriate transcriptional/translational control signals. These methods include in vitro recombinant DNA techniques, synthetic techniques and in vivo recombination/genetic recombination. See, for example, the techniques described in Maniatis et al., *Molecular Cloning A Laboratory Manual*, Cold Spring Harbor Laboratory, N.Y. (1989) and Ausubel et al., *Current Protocols in Molecular Biology*, Greene Publishing Associates and Wiley Interscience, N.Y. (1989).

Promoter regions can be selected from any desired gene using CAT (chloramphenicol transferase) vectors or other vectors with selectable markers. Two appropriate vectors are pKK232-8 and pCM7. Particular named bacterial promoters include lacI, lacZ, T3, T7, gpt, lambda P, and trc. Eukaryotic promoters include CMV immediate early, HSV thymidine kinase, early and late SV40, LTRs from retrovirus, and mouse metallothionein-I.

Generally, recombinant expression vectors will include origins of replication and selectable markers permitting transformation of the host cell, e.g., the ampicillin resistance gene of *E. coli* and *S. cerevisiae* TRP1 gene, and a promoter derived from a highly-expressed gene to direct transcription of a downstream structural sequence. Such promoters can be derived from operons encoding glycolytic enzymes such as 3-phosphoglycerate kinase (PGK), a-factor, acid phosphatase, or heat shock proteins, among others. The polynucleotide of the invention is assembled in appropriate phase with translation initiation and termination sequences, and preferably, a leader sequence capable of directing secretion of translated protein into the periplasmic space or extracellular medium. Optionally, the polynucleotide of the invention can encode a fusion protein including an N-terminal identification peptide imparting desired characteristics, e.g., stabilization or simplified purification of expressed recombinant product.

Useful expression vectors for bacteria are constructed by inserting a polynucleotide of the invention together with suitable translation initiation and termination signals, optionally in operable reading phase with a functional promoter. The vector will comprise one or more phenotypic selectable markers and an origin of replication to ensure maintenance of the vector and to, if desirable, provide amplification within the host. Suitable prokaryotic hosts for transformation include *E. coli, Bacillus subtilis, Salmonella typhimurium* and various species within the genera *Pseudomonas, Streptomyces*, and *Staphylococcus*, although others may also be employed as a matter of choice.

As a representative but nonlimiting example, useful expression vectors for bacteria can comprise a selectable marker and bacterial origin of replication derived from commercially available plasmids comprising genetic elements of the well known cloning vector pBR322 (ATCC 37017). Such commercial vectors include, for example, pKK223-3 (Pharmacia Fine Chemicals, Uppsala, Sweden) and GEM 1 (Promega Biotec, Madison, Wis., USA). These pBR322 'backbone' sections are combined with an appropriate promoter and the structural sequence to be expressed.

The present invention further provides host cells containing the vectors of the present invention, wherein the nucleic acid has been introduced into the host cell using known transformation, transfection or infection methods. The host cell can be a higher eukaryotic host cell, such as a mammalian cell, a lower eukaryotic host cell, such as a yeast cell, or the host cell can be a prokaryotic cell, such as a bacterial cell. Introduction of the recombinant construct into the host cell can be effected, for example, by calcium phosphate transfection, DEAE, dextran mediated transfection, or electroporation (Davis, L. et al., *Basic Methods in Molecular Biology* (1986)).

Any host/vector system can be used to identify one or more of the target elements of the present invention. These include, but are not limited to, eukaryotic hosts such as HeLa cells, Cv-1 cell, COS cells, and Sf9 cells, as well as prokaryotic host such as *E. coli* and *B. subtilis*. The most preferred cells are those which do not normally express the particular reporter polypeptide or protein or which expresses the reporter polypeptide or protein at low natural level.

The host of the present invention may also be a yeast or other fungi. In yeast, a number of vectors containing constitutive or inducible promoters may be used. For a review see, *Current Protocols in Molecular Biology*, Vol. 2, Ed. Ausubel et al., Greene Publish. Assoc. & Wiley Interscience, Ch. 13 (1988); Grant et al., *Expression and Secretion Vectors for Yeast*, in *Methods in Enzymology*, Ed. Wu & Grossman, Acad. Press, N.Y. 153:516-544 (1987); Glover, DNA Cloning, Vol. II, IRL Press, Wash., D.C., Ch. 3 (1986); Bitter, *Heterologous Gene Expression in Yeast*, in *Methods in Enzymology*, Eds. Berger & Kimmel, Acad. Press, N.Y. 152:673-684 (1987); and *The Molecular Biology of the Yeast Saccharomyces*, Eds. Strathern et al., Cold Spring Harbor Press, Vols. I and II (1982).

The host of the invention may also be a prokaryotic cell such as *E. coli*, other enterobacteriaceae such as *Serratia marescans*, bacilli, various pseudomonads, or other prokaryotes which can be transformed, transfected, infected, etc. (i.e., a method exists for introducing nucleic acids to the host cell).

The present invention further provides host cells genetically engineered to contain the polynucleotides of the invention. For example, such host cells may contain nucleic acids of the invention introduced into the host cell using known transformation, transfection or infection methods. The present invention still further provides host cells genetically engineered to express the polynucleotides of the invention, wherein such polynucleotides are in operative association with a regulatory sequence heterologous to the host cell which drives expression of the polynucleotides in the cell.

The host cell can be a higher eukaryotic host cell, such as a mammalian cell, a lower eukaryotic host cell, such as a yeast cell, or the host cell can be a prokaryotic cell, such as a bacterial cell. Introduction of the recombinant construct into the host cell can be effected by calcium phosphate transfection, DEAE, dextran mediated transfection, or electroporation (Davis, L. et al., Basic Methods in Molecular Biology (1986)). The host cells containing one of polynucleotides of the invention, can be used in conventional manners to produce the gene product encoded by the isolated fragment (in the case of an ORF) or can be used to produce a heterologous protein under the control of the EMF.

Any host/vector system can be used to express one or more of the ORFs of the present invention. These include, but are not limited to, eukaryotic hosts such as HeLa cells, Cv-1 cell, COS cells, and Sf9 cells, as well as prokaryotic host such as E. coli and B. subtilis. The most preferred cells are those which do not normally express the particular polypeptide or protein or which expresses the polypeptide or protein at low natural level. Mature proteins can be expressed in mammalian cells, yeast, bacteria, or other cells under the control of appropriate promoters. Cell-free translation systems can also be employed to produce such proteins using RNAs derived from the DNA constructs of the present invention. Appropriate cloning and expression vectors for use with prokaryotic and eukaryotic hosts are described by Sambrook, et al., in Molecular Cloning: A Laboratory Manual, Second Edition, Cold Spring Harbor, N.Y. (1989), the disclosure of which is hereby incorporated by reference.

Various mammalian cell culture systems can also be employed to express recombinant protein. Examples of mammalian expression systems include the COS-7 lines of monkey kidney fibroblasts, described by Gluzman, Cell 23:175 (1981), and other cell lines capable of expressing a compatible vector, for example, the C127, 3T3, CHO, HeLa and BHK cell tines. Mammalian expression vectors will comprise an origin of replication, a suitable promoter and also any necessary ribosome binding sites, polyadenylation site, splice donor and acceptor sites, transcriptional termination sequences, and 5' flanking nontranscribed sequences. DNA sequences derived from the SV40 viral genome, for example, SV40 origin, early promoter, enhancer, splice, and polyadenylation sites may be used to provide the required nontranscribed genetic elements. Recombinant polypeptides and proteins produced in bacterial culture are usually isolated by initial extraction from cell pellets, followed by one or more salting-out, aqueous ion exchange or size exclusion chromatography steps. Protein refolding steps can be used, as necessary, in completing configuration of the mature protein. Finally, high performance liquid chromatography (HPLC) can be employed for final purification steps. Microbial cells employed in expression of proteins can be disrupted by any convenient method, including freeze-thaw cycling, sonication, mechanical disruption, or use of cell lysing agents.

A number of types of cells may act as suitable host cells for expression of the protein. Mammalian host cells include, for example, monkey COS cells, Chinese Hamster Ovary (CHO) cells, human kidney 293 cells, human epidermal A431 cells, human Colo205 cells, 3T3 cells, CV-1 cells, other transformed primate cell lines, normal diploid cells, cell strains derived from in vitro culture of primary tissue, primary explants, HeLa cells, mouse L cells, BHK, HL-60, U937, HaK or Jurkat cells.

Alternatively, it may be possible to produce the protein in lower eukaryotes such as yeast or in prokaryotes such as bacteria. Potentially suitable yeast strains include Saccharomyces cerevisiae, Schizosaccharomyces pombe, Kluyveromyces strains, Candida, or any yeast strain capable of expressing heterologous proteins. Potentially suitable bacterial strains include Escherichia coli, Bacillus subtilis, Salmonella typhimurium, or any bacterial strain capable of expressing heterologous proteins. If the protein is made in yeast or bacteria, it may be necessary to modify the protein produced therein, for example by phosphorylation or glycosylation of the appropriate sites, in order to obtain the functional protein. Such covalent attachments may be accomplished using known chemical or enzymatic methods.

In another embodiment of the present invention, cells and tissues may be engineered to express an endogenous gene comprising the polynucleotides of the invention under the control of inducible regulatory elements, in which case the regulatory sequences of the endogenous gene may be replaced by homologous recombination. As described herein, gene targeting can be used to replace a gene's existing regulatory region with a regulatory sequence isolated from a different gene or a novel regulatory sequence synthesized by genetic engineering methods. Such regulatory sequences may be comprised of promoters, enhancers, scaffold-attachment regions, negative regulatory elements, transcriptional initiation sites, regulatory protein binding sites or combinations of said sequences. Alternatively, sequences which affect the structure or stability of the RNA or protein produced may be replaced, removed, added, or otherwise modified by targeting, including polyadenylation signals. mRNA stability elements, splice sites, leader sequences for enhancing or modifying transport or secretion properties of the protein, or other sequences which alter or improve the function or stability of protein or RNA molecules.

The targeting event may be a simple insertion of the regulatory sequence, placing the gene under the control of the new regulatory sequence, e.g., inserting a new promoter or enhancer or both upstream of a gene. Alternatively, the targeting event may be a simple deletion of a regulatory element, such as the deletion of a tissue-specific negative regulatory element. Alternatively, the targeting event may replace an existing element; for example, a tissue-specific enhancer can be replaced by an enhancer that has broader or different cell-type specificity than the naturally occurring elements. Here, the naturally occurring sequences are deleted and new sequences are added. In all cases, the identification of the targeting event may be facilitated by the use of one or more selectable marker genes that are contiguous with the targeting DNA, allowing for the selection of cells in which the exogenous DNA has integrated into the host cell genome. The identification of the targeting event may also be facilitated by the use of one or more marker genes exhibiting the property of negative selection, such that the negatively selectable marker is linked to the exogenous DNA, but configured such that the negatively selectable marker flanks the targeting sequence, and such that a correct homologous recombination event with sequences in the host cell genome does not result in the stable integration of the negatively selectable marker. Markers useful for this purpose include the Herpes Simplex Virus thymidine kinase (TK) gene or the bacterial xanthine-guanine phosphoribosyl-transferase (gpt) gene.

The gene targeting or gene activation techniques which can be used in accordance with this aspect of the invention are more particularly described in U.S. Pat. No. 5,272,071 to Chappel; U.S. Pat. No. 5,578,461 to Sherwin et al.; International Application No. PCT/US92/09627 (WO93/09222) by Selden et al.; and International Application No. PCT/

US90/06436 (WO91/06667) by Skoultchi et al., each of which is incorporated by reference herein in its entirety.

In general, techniques for preparing polyclonal and monoclonal antibodies as well as hybridomas capable of producing the desired antibody are well known in the art (Campbell, A. M., *Monoclonal Antibodies Technology: Laboratory Techniques in Biochemistry and Molecular Biology*, Elsevier Science Publishers, Amsterdam, The Netherlands (1984); St. Groth et al., *J. Immunol.* 35:1-21 (1990); Kohler and Milstein, *Nature* 256:495-497 (1975)), the trioma technique, the human B-cell hybridoma technique (Kozbor et al., *Immunology Today* 4:72 (1983); Cole et al., in *Monoclonal Antibodies and Cancer Therapy*, Alan R. Liss, Inc. (1985), pp. 77-96).

Methods for immunization are well known in the art. Such methods include subcutaneous or interperitoneal injection of the polypeptide. One skilled in the art will recognize that the amount of the protein encoded by the reporter gene of the present invention used for immunization will vary based on the animal which is immunized, the antigenicity of the peptide and the site of injection.

The polypeptide or protein of the invention which is used as an immunogen may be modified or administered in an adjuvant in order to increase the polypeptide or protein's antigenicity. Methods of increasing the antigenicity of a polypeptide or protein are well known in the art and include, but are not limited to, coupling the antigen with a heterologous protein (such as globulin or β-galactosidase) or through the inclusion of an adjuvant during immunization.

For monoclonal antibodies, spleen cells from the immunized animals are removed, fused with myeloma cells, such as SP2/0-Ag14 myeloma cells, and allowed to become monoclonal antibody producing hybridoma cells.

Any one of a number of methods well known in the art can be used to identify the hybridoma cell which produces an antibody with the desired characteristics. These include screening the hybridomas with an ELISA assay, western blot analysis, or radioimmunoassay (Lutz et al., *Exp. Cell Research*. 175:109-124 (1988)).

Hybridomas secreting the desired antibodies are cloned and the class and subclass is determined using procedures known in the art (Campbell, A. M., *Monoclonal Antibody Technology: Laboratory Techniques in Biochemistry and Molecular Biology*, Elsevier Science Publishers, Amsterdam, The Netherlands (1984)).

For polyclonal antibodies, antibody containing antisera is isolated from the immunized animal and is screened for the presence of antibodies with the desired specificity using one of the above-described procedures.

The present invention further provides the above-described antibodies in detectably labeled form. Antibodies can be detectably labeled through the use of radioisotopes, affinity labels (such as biotin, avidin, etc.), enzymatic labels (such as horseradish peroxidase, alkaline phosphatase, etc.) fluorescent labels (such as FITC or rhodamine, etc.), paramagnetic atoms, etc. Procedures for accomplishing such labeling are well-known in the art, for example, see (Sternberger, L. A. et al., *J. Histochem. CytoChem.* 18:315 (1970); Bayer, E. A. et al., *Meth. Enzym.* 62:308 (1979); Engval, E. et al., *Immunol.* 109:129 (1972); Goding, J. W. *J. Immunol. Meth.* 13:215 (1976)).

The labeled antibodies of the present invention can be used for in vitro, in vivo, and in situ assays to identify cells or tissues in which the polypeptide or protein of the invention is expressed.

The present invention further provides the above-described antibodies immobilized on a solid support. Examples of such solid supports include plastics such as polycarbonate, complex carbohydrates such as agarose and sepharose, acrylic resins and such as polyacrylamide and latex beads. Techniques for coupling antibodies to such solid supports are well known in the art (Weir, D. M. et al., '*Handbook of Experimental Immunology*' 4th Ed., Blackwell Scientific Publications, Oxford, England, Chapter 10 (1986); Jacoby, W. D. et al., Meth. Enzym. 34 Academic Press, N.Y. (1974)). The immobilized antibodies of the present invention can be used for immuno-affinity purification of host cells that are expressing the polypeptide or protein of the invention.

Host cells are transfected or preferably infected or transformed with the above-described vectors, and cultured in nutrient media appropriate for selecting transductants or transformants containing the vector.

The host cells which express the polypeptide or protein of the invention product may be identified by at least four general approaches; (a) DNA-DNA or DNA-RNA hybridization; (b) the presence or absence of gene functions; (c) assessing the level of transcription as measured by the expression of mRNA transcripts in the host cell; and (d) detection of the gene product as measured by immunoassay or by its biological activity.

In the first approach, the presence of the polypeptide or protein of the invention inserted in the vector can be detected by DNA-DNA or DNA-RNA hybridization using probes comprising nucleotide sequences that are homologous to the polypeptide or protein of the invention, respectively, or portions or derivatives thereof.

In the second approach, the recombinant expression vector/host system can be identified and selected based upon the presence or absence of certain "marker" gene functions (e.g., thymidine kinase activity, resistance to antibiotics, resistance to methotrexate, transformation phenotype, occlusion body formation in baculovirus, etc.). For example, if the polypeptide or protein of the invention is inserted within a marker gene sequence of the vector, recombinant cells containing the polypeptide or protein of the invention can be identified by the absence of the marker gene function. Alternatively, a marker gene can be placed in tandem with the polypeptide or protein of the invention under the control of the same or different promoter used to control the expression of the polypeptide or protein of the invention. Expression of the marker in response to induction or selection indicates expression of the polypeptide or protein of the invention.

In the third approach, transcriptional activity of the polypeptide or protein of the invention can be assessed by hybridization assays. For example, RNA can be isolated and analyzed by Northern blot using a probe homologous to the polypeptide or protein of the invention or particular portions thereof. Alternatively, total nucleic acids of the host cell may be extracted and assayed for hybridization to such probes.

In the fourth approach, the expression of a product from the polypeptide or protein of the invention can be assessed immunologically, for example by Western blots, immunoassays such as radioimmuno-precipitation, enzyme-linked immunoassays and the like.

The polynucleotides of the invention also provide polynucleotides including nucleotide sequences that are substantially equivalent to the polynucleotides of the invention. Polynucleotides according to the invention can have at least about 80%, more typically at least about 90%, and even more typically at least about 95%, sequence identity to a polynucleotide of the invention. The invention also provides the complement of the polynucleotides including a nucleotide sequence that has at least about 80%, more typically at least about 90%, and even more typically at least about 95%, sequence identity to a polynucleotide encoding a polypeptide recited above. The polynucleotide can be DNA (genomic, cDNA, amplified, or synthetic) or RNA. Methods and algorithms for obtaining such polynucleotides are well known to those of skill in the art and can include, for example, methods for determining hybridization conditions which can routinely isolate polynucleotides of the desired sequence identities.

A polynucleotide according to the invention can be joined to any of a variety of other nucleotide sequences by well-established recombinant DNA techniques (see Sambrook J et al. (1989) Molecular Cloning: A Laboratory Manual, Cold Spring Harbor Laboratory, NY). Useful nucleotide sequences for joining to polypeptides include an assortment of vectors, e.g., plasmids, cosmids, lambda phage derivatives, phagemids, and the like, that are well known in the art. Accordingly, the invention also provides a vector including a polynucleotide of the invention and a host cell containing the polynucleotide. In general, the vector contains an origin of replication functional in at least one organism, convenient restriction endonuclease sites, and a selectable marker for the host cell. Vectors according to the invention include expression vectors, replication vectors, probe generation vectors, and sequencing vectors. A host cell according to the invention can be a prokaryotic or eukaryotic cell and can be a unicellular organism or part of a multicellular organism.

The sequences falling within the scope of the present invention are not limited to the specific sequences herein described, but also include a representative fragment thereof, or a nucleotide sequence at least 99.9% identical to a nucleic acid of the invention. Furthermore, to accommodate codon variability, the invention includes nucleic acid molecules encoding the polypeptide sequences of the invention. In other words, in the coding region of a polypeptide sequence of the invention, substitution of one codon for another which encodes the same amino acid is expressly contemplated. Any specific sequence disclosed herein can be readily screened for errors by resequencing a particular fragment, such as an ORF, in both directions (i.e., sequence both strands).

The present invention further provides recombinant constructs comprising a nucleic acid of the invention, or a fragment thereof. The recombinant constructs of the present invention comprise a vector, such as a plasmid or viral vector, into which a nucleic acid of the invention, or a fragment thereof is inserted, in a forward or reverse orientation. In the case of a vector comprising one of the ORFs of the present invention, the vector may further comprise regulatory sequences, including for example, a promoter, operably linked to the ORF. For vectors comprising the EMFs and UMFs of the present invention, the vector may further comprise a marker sequence or heterologous ORF operably linked to the EMF or UMF. Large numbers of suitable vectors and promoters are known to those of skill in the art and are commercially available for generating the recombinant constructs of the present invention. The following vectors are provided by way of example. Bacterial: pBs, phagescript, PsiX174, pBluescript SK, pBs KS, pNH8a, pNH16a, pNH18a, pNH46a (Stratagene); pTrc99A, pKK223-3, pKK233-3, pDR540, pRIT5 (Pharmacia). Eukaryotic: pWLneo, pSV2cat, pOG44, PXTI, pSG (Stratagene) pSVK3, pBPV, pMSG, pSVL (Pharmacia).

The isolated polynucleotide of the invention may be operably linked to an expression control sequence such as the pMT2 or pED expression vectors disclosed in Kaufman et al., Nucleic Acids Res. 19, 4485-4490 (1991), in order to produce the protein or polypeptide recombinantly. Many suitable expression control sequences are known in the art. General methods of expressing recombinant proteins are also known and are exemplified in R. Kaufman, Methods in Enzymology 185, 537-566 (1990). As defined herein "operably linked" means that the isolated polynucleotide of the invention and an expression control sequence are situated within a vector or cell in such a way that the protein or polypeptide is expressed by a host cell which has been transformed (transfected) with the ligated polynucleotide/expression control sequence.

Promoter regions can be selected from any desired gene using CAT (chloramphenicol transferase) vectors or other vectors with selectable markers. Two appropriate vectors are pKK232-8 and pCM7. Particular named bacterial promoters include lacI, lacZ, T3, T7, gpt, lambda $P_R$, and trc. Eukaryotic promoters include CMV immediate early, HSV thymidine kinase, early and late SV40, LTRs from retrovirus, and mouse metallothionein-I. Selection of the appropriate vector and promoter is well within the level of ordinary skill in the art. Generally, recombinant expression vectors will include origins of replication and selectable markers permitting transformation of the host cell, e.g., the ampicillin resistance gene of *E. coli* and *S. cerevisiae* TRP1 gene, and a promoter derived from a highly-expressed gene to direct transcription of a downstream structural sequence. Such promoters can be derived from operons encoding glycolytic enzymes such as 3-phosphoglycerate kinase (PGK), a-factor, acid phosphatase, or heat shock proteins, among others. The heterologous structural sequence is assembled in appropriate phase with translation initiation and termination sequences, and preferably, a leader sequence capable of directing secretion of translated protein or polypeptide into the periplasmic space or extracellular medium. Optionally, the heterologous sequence can encode a fusion protein including an N-terminal identification peptide imparting desired characteristics, e.g., stabilization or simplified purification of expressed recombinant product. Useful expression vectors for bacterial use are constructed by inserting a structural DNA sequence encoding a desired protein or polypeptide together with suitable translation initiation and termination signals in operable reading phase with a functional promoter. The vector will comprise one or more phenotypic selectable markers and an origin of replication to ensure maintenance of the vector and to, if desirable, provide amplification within the host. Suitable prokaryotic hosts for transformation include *E. coli, Bacillus subtilis, Salmonella typhimurium* and various species within the genera *Pseudomonas, Streptomyces,* and *Staphylococcus,* although others may also be employed as a matter of choice.

As a representative but non-limiting example, useful expression vectors for bacterial use can comprise a selectable marker and bacterial origin of replication derived from commercially available plasmids comprising genetic elements of the well known cloning vector pBR322 (ATCC 37017). Such commercial vectors include, for example, pKK223-3 (Pharmacia Fine Chemicals, Uppsala, Sweden) and GEM 1 (Promega Biotec, Madison, Wis., USA). These pBR322 'backbone' sections are combined with an appropriate promoter and the structural sequence to be expressed. Following transformation of a suitable host strain and growth of the host strain to an appropriate cell density, the selected promoter is induced or derepressed by appropriate means (e.g., temperature shift or chemical induction) and cells are cultured for an additional period. Cells are typically harvested by centrifugation, disrupted by physical or chemical means, and the resulting crude extract retained for further purification.

Included within the scope of the nucleic acid sequences of the invention are nucleic acid sequences that hybridize under stringent conditions to a polynucleotide of the invention, which polynucleotide is greater than about 10 bp, preferably 20-50 bp, and even greater than 100 bp. In accordance with the invention, polynucleotide sequences of the invention, or functional equivalents thereof, may be used to generate recombinant DNA molecules that direct the expression of that polynucleotide, or a functional equivalent thereof, in appropriate host cells.

The polynucleotides of the invention are further directed to sequences which encode variants of the polypeptides or proteins of the invention. These amino acid sequence variants may be prepared by methods known in the art by introducing appropriate nucleotide changes into a native or variant polynucleotide. There are two variables in the construction of amino acid sequence variants: the location of the mutation and the nature of the mutation. The amino acid sequence variants of the nucleic acids are preferably constructed by mutating the polynucleotide to give an amino acid sequence that does not occur in nature. These amino acid alterations can be made at sites that differ in the nucleic acids from different species (variable positions) or in highly conserved regions (constant regions). Sites at such locations will typically be modified in series, e.g., by substituting first with conservative choices (e.g., hydrophobic amino acid to a different hydrophobic amino acid) and then with more distant choices (e.g., hydrophobic amino acid to a charged amino acid), and then deletions or insertions may be made at the target site. Amino acid sequence deletions generally range from about 1 to 30 residues, preferably about 1 to 10 residues, and are typically contiguous. Amino acid insertions include amino- and/or carboxyl-terminal fusions ranging in length from one to one hundred or more residues, as well as intrasequence insertions of single or multiple amino acid residues. Intrasequence insertions may range generally from about 1 to 10 amino residues, preferably from 1 to 5 residues. Examples of terminal insertions include the heterologous signal sequences necessary for secretion or for intracellular targeting in different host cells.

Amino acid sequence deletions generally range from about 1 to 30 residues, preferably about 1 to 10 residues, and are typically contiguous. Amino acid insertions include amino- and/or carboxyl-terminal fusions ranging in length from one to one hundred or more residues, as well as intrasequence insertions of single or multiple amino acid residues. Intrasequence insertions may range generally from about 1 to 10 amino residues, preferably from 1 to 5 residues. Examples of terminal insertions include the heterologous signal sequences necessary for secretion or for intracellular targeting in different host cells.

PCR may also be used to create amino acid sequence variants of the polynucleotides of the invention. When small amounts of template DNA are used as starting material, primer(s) that differs slightly in sequence from the corresponding region in the template DNA can generate the desired amino acid variant. PCR amplification results in a population of product DNA fragments that differ from the polynucleotide template encoding the polypeptide or protein at the position specified by the primer. The product DNA fragments replace the corresponding region in the plasmid and this gives the desired amino acid variant.

In a preferred method, polynucleotides encoding the polynucleotides of the invention are changed via site-directed mutagenesis. This method uses oligonucleotide sequences that encode the polynucleotide sequence of the desired amino acid variant, as well as a sufficient adjacent nucleotide on both sides of the changed amino acid to form a stable duplex on either side of the site of being changed. In general, the techniques of site-directed mutagenesis are well known to those of skill in the art and this technique is exemplified by publications such as, Edelman et al., *DNA* 2:183 (1983). A versatile and efficient method for producing site-specific changes in a polynucleotide sequence was published by Zoller and Smith, *Nucleic Acids Res.* 10:6487-6500 (1982). PCR may also be used to create amino acid sequence variants of the novel nucleic acids. When small amounts of template DNA are used as starting material, primer(s) that differs slightly in sequence from the corresponding region in the template DNA can generate the desired amino acid variant. PCR amplification results in a population of product DNA fragments that differ from the polynucleotide template encoding the polypeptide at the position specified by the primer. The product DNA fragments replace the corresponding region in the plasmid and this gives the desired amino acid variant.

A further technique for generating amino acid variants is the cassette mutagenesis technique described in Wells et al., *Gene* 34:315 (1985); and other mutagenesis techniques well known in the art, such as, for example, the techniques in Sambrook et al., supra, and *Current Protocols in Molecular Biology*, Ausubel et al. Due to the inherent degeneracy of the genetic code, other DNA sequences which encode substantially the same or a functionally equivalent amino acid sequence may be used in the practice of the invention for the cloning and expression of these novel nucleic acids. Such DNA sequences include those which are capable of hybridizing to the appropriate novel nucleic acid sequence under stringent conditions.

The invention encompasses polypeptides or proteins encoded by the polynucleotides of the invention. Fragments of the polypeptides or proteins of the present invention which are capable of exhibiting biological activity are also encompassed by the present invention. Fragments of the protein or polypeptide may be in linear form or they may be cyclized using known methods, for example, as described in H. U. Saragovi, et al., Bio/Technology 10, 773-778 (1992) and in R. S. McDowell, et al., J. Amer. Chem. Soc. 114, 9245-9253 (1992), both of which are incorporated herein by reference.

The present invention also provides both full-length and mature forms of the polypeptides or proteins of the invention. The full-length form of the such polypeptides or proteins can be identified by translation of the nucleotide sequence of each polynucleotide of the invention. The mature form of such polypeptide or protein may be obtained by expression of the full-length polynucleotide in a suitable mammalian cell or other host cell. The sequence of the mature form of the polypeptide or protein may also be determinable from the amino acid sequence of the full-length form.

Where the protein or polypeptide of the present invention is membrane-bound (e.g., is a receptor), the present invention also provides for soluble forms of such protein or polypeptide. In such forms part or all of the intracellular and transmembrane domains of the protein or polypeptide are deleted such that the protein or polypeptide is fully secreted from the cell in which it is expressed. The intracellular and transmembrane domains of proteins or polypeptides of the invention can be identified in accordance with known techniques for determination of such domains from sequence information.

The invention also relates to methods for producing a polypeptide or protein of the invention comprising growing a culture of the cells of the invention in a suitable culture medium, and purifying the protein or polypeptide of the invention from the culture. For example, the methods of the invention include a process for producing a polypeptide or protein of the invention in which a host cell containing a suitable expression vector that includes a polynucleotide or protein of the invention is cultured under conditions that allow expression of the encoded polypeptide or protein. The polypeptide or protein can be recovered from the culture, conveniently from the culture medium, and further purified.

The invention further provides a polypeptide or protein of the invention including an amino acid sequence that is substantially equivalent to an amino acid sequence encoded by a polynucleotide of the invention. Polypeptides or proteins according to the invention can have at least about 95%, and more typically at least about 98%, sequence identity to an amino acid sequence encoded by a polynucleotide of the invention.

The present invention further provides isolated polypeptides or proteins encoded by the polynucleotides of the present invention or by degenerate variants of the polynucleotides of the present invention. By 'degenerate variant' is intended polynucleotides which differ from a nucleic acid fragment of the present invention (e.g., an ORF) by nucleotide sequence but, due to the degeneracy of the genetic code, encode an identical polypeptide sequence. Preferred polynucleotides of the present invention are the ORFs that encode proteins or polypeptides. A variety of methodologies known in the art can be utilized to obtain any one of the isolated polypeptides or proteins of the present invention. At the simplest level, the amino acid sequence can be synthesized using commercially available peptide synthesizers. This is particularly useful in producing small peptides and fragments of larger polypeptides. Fragments are useful, for example, in generating antibodies against the native polypeptide. In an alternative method, the polypeptide or protein is purified from bacterial cells which naturally produce the polypeptide or protein. One skilled in the art can readily follow known methods for isolating polypeptides and proteins in order to obtain one of the isolated polypeptides or proteins of the present invention. These include, but are not limited to, immunochromatography, HPLC, size-exclusion chromatography, ion-exchange chromatography, and immuno-affinity chromatography. See, e.g., *Scopes, Protein Purification: Principles and Practice*, Springer-Verlag (1994); Sambrook, et al., in *Molecular Cloning: A Laboratory Manual*; Ausubel et al., *Current Protocols in Molecular Biology*.

The polypeptides and proteins of the present invention can alternatively be purified from cells which have been altered to express the desired polypeptide or protein. As used herein, a cell is said to be altered to express a desired polypeptide or protein when the cell, through genetic manipulation, is made to produce a polypeptide or protein which it normally does not produce or which the cell normally produces at a lower level. One skilled in the art can readily adapt procedures for introducing and expressing either recombinant or synthetic sequences into eukaryotic or prokaryotic cells in order to generate a cell which produces one of the polypeptides or proteins of the present invention. The purified polypeptides or proteins can be used in in vitro binding assays which are well known in the art to identify molecules which bind to the polypeptides or proteins. These molecules include but are not limited to, for e.g., small molecules, molecules from combinatorial libraries, antibodies or other proteins or polypeptides. The molecules identified in the binding assay are then tested for antagonist or agonist activity in in vivo tissue culture or animal models that are well known in the art. In brief, the molecules are titrated into a plurality of cell cultures or animals and then tested for either cell/animal death or prolonged survival of the animal/cells.

In addition, the binding molecules may be complexed with toxins, e.g., ricin or cholera, or with other compounds that are toxic to cells. The toxin-binding molecule complex is then targeted to the tumor or other cell by the specificity of the binding molecule.

The protein or polypeptide of the invention may also be expressed as a product of transgenic animals, e.g., as a component of the milk of transgenic cows, goats, pigs, or sheep which are characterized by somatic or germ cells containing a polynucleotide encoding the protein or polypeptide of the invention.

The protein or polypeptide of the invention may also be produced by known conventional chemical synthesis. Methods for constructing the proteins or polypeptides of the present invention by synthetic means are known to those skilled in the art. The synthetically-constructed proteins or polypeptides, by virtue of sharing primary, secondary or tertiary structural and/or conformational characteristics with proteins or polypeptides may possess biological properties in common therewith, including protein activity. Thus, they may be employed as biologically active or immunological substitutes for natural, purified proteins or polypeptides of the invention in screening of therapeutic compounds and in immunological processes for the development of antibodies.

The proteins or polypeptides of the invention provided herein also include proteins or polypeptides characterized by amino acid sequences similar to those of purified proteins or polypeptides of the invention but into which modifications are naturally provided or deliberately engineered. For example, modifications in the peptide or DNA sequences can be made by those skilled in the art using known techniques. Modifications of interest in the protein sequences may include the alteration, substitution, replacement, insertion or deletion of a selected amino acid residue in the coding sequence. For example, one or more of the cysteine residues may be deleted or replaced with another amino acid to alter the conformation of the molecule. Techniques for such alteration, substitution, replacement, insertion or deletion are well known to those skilled in the art (see, e.g., U.S. Pat. No. 4,518,584). Preferably, such alteration, substitution, replacement, insertion or deletion retains the desired activity of the protein or polypeptide.

Other fragments and derivatives of the polypeptides or proteins of the invention which would be expected to retain protein activity in whole or in part and may thus be useful for screening or other immunological methodologies may also be easily made by those skilled in the art given the disclosures herein. Such modifications are encompassed by the present invention.

The protein or polypeptide of the invention may also be produced by operably linking a polynucleotide of the invention to suitable control sequences in one or more insect expression vectors, and employing an insect expression system. Materials and methods for baculovirus/insect cell expression systems are commercially available in kit form from, e.g., Invitrogen, San Diego, Calif., U.S.A. (the MaxBat® kit), and such methods are well known in the art, as described in Summers and Smith, Texas Agricultural Experiment Station Bulletin No. 1555 (1987), incorporated herein by reference. As used herein, an insect cell capable of expressing a polynucleotide of the present invention is "transformed."

The protein or polypeptide of the invention may be prepared by culturing transformed host cells under culture conditions suitable to express the recombinant protein or polypeptide. The resulting expressed protein or polypeptide may then be purified from such culture (i.e., from culture medium or cell extracts) using known purification processes, such as gel filtration and ion exchange chromatography. The purification of the protein or polypeptide may also include an affinity column containing agents which will bind to the protein or polypeptide; one or more column steps over such affinity resins as concanavalin A-agarose, Heparin-Toyopearl® or Cibacrom blue 3GA Sepharose®; one or more steps involving hydrophobic interaction chromatography using such resins as phenyl ether, butyl ether, or propyl ether; or immunoaffinity chromatography.

Alternatively, the protein or polypeptide of the invention may also be expressed in a form which will facilitate purification. For example, it may be expressed as a fusion protein, such as those of maltose binding protein (MBP), glutathione-S-transferase (GST) or thioredoxin (TRX). Kits for expression and purification of such fusion proteins are commercially available from New England BioLab (Beverly, Mass.), Pharmacia (Piscataway, N.J.) and In Vitrogen, respectively. The protein or polypeptide can also be tagged with an epitope and subsequently purified by using a specific antibody directed to such epitope. One such epitope ("Flag") is commercially available from Kodak (New Haven, Conn.).

Finally, one or more reverse-phase high performance liquid chromatography (RP-HPLC) steps employing hydrophobic RP-HPLC media, e.g., silica gel having pendant methyl or other aliphatic groups, can be employed to further purify the protein or polypeptide. Some or all of the foregoing purification steps, in various combinations, can also be employed to provide a substantially homogeneous isolated recombinant protein or polypeptide. The protein or polypeptide thus purified is substantially free of other mammalian proteins and is defined in accordance with the present invention as an "isolated protein."

The polynucleotides and polypeptides of the present invention are expected to exhibit one or more of the uses or biological activities (including those associated with assays cited herein) identified below. Uses or activities described for the polypeptides or proteins of the present invention may be provided by administration or use of such proteins or polypeptides or by administration or use of polynucleotides encoding such proteins or polypeptides (such as, for example, in gene therapies or vectors suitable for introduction of DNA).

The polynucleotides provided by the present invention can be used by the research community for various purposes. The polynucleotides can be used to express recombinant protein or polypeptide for analysis, characterization, diagnostic or therapeutic use; as markers for tissues in which the target protein is abnormally or normally expressed (e.g., constitutively or at a particular stage of tissue differentiation or development or in disease states); as molecular weight markers on Southern gels; as chromosome markers or tags (when labeled) to identify chromosomes or to map related gene positions; to compare with endogenous DNA sequences in patients to identify potential genetic disorders; as probes to hybridize and thus discover novel, related DNA sequences; as a source of information to derive PCR primers for genetic fingerprinting; as a probe to "subtract-out" known sequences in the process of discovering other novel polynucleotides; for selecting and making oligomers for attachment to a "gene chip" or other support, including for examination of expression patterns; for attachment to a substrate to make an antibody chip for examining protein (target) expression patterns or target expression levels or the presence of the target, and as an antigen to raise anti-idiotype antibodies. When the target protein binds or potentially binds to another protein or other factor, the polynucleotides of the invention can also be used in interaction trap assays (such as, for example, that described in Gyuris et al., Cell 75:791-803 (1993)) to identify polynucleotides encoding the other protein or factor with which binding occurs or to identify other factors or proteins involved in the binding interation.

The proteins or polypeptides provided by the present invention can similarly be used to determine biological activity, including in a panel of multiple proteins or polypeptides for high-throughput screening; as a reagent (including the labeled reagent) in assays designed to quantitatively determine levels of the target protein in biological samples; as markers for tissues in which the target protein of the invention is normally or abnormally expressed (either constitutively or at a particular stage of tissue differentiation or development or in a disease state); and, of course, to isolate correlative receptors or ligands. Where the target protein binds or potentially binds to another protein or factor (such as, for example, in a receptor-ligand interaction), the polypeptide of the invention can be used to identify the other protein or factor with which binding occurs or to identify inhibitors of the binding interaction. Proteins involved in these binding interactions can also be used to screen for peptide or small molecule inhibitors or agonists of the binding interaction.

Any or all of these research utilities are capable of being developed into reagent grade or kit format for commercialization as research products.

Methods for performing the uses listed above are well known to those skilled in the art. References disclosing such methods include without limitation "Molecular Cloning: A Laboratory Manual", 2d ed., Cold Spring Harbor Laboratory Press, Sambrook, J., E. F. Fritsch and T. Maniatis eds., 1989, and "Methods in Enzymology: Guide to Molecular Cloning Techniques", Academic Press, Berger, S. L. and A. R. Kimmel eds., 1987.

Polynucleotides, proteins, and polypeptides of the present invention can also be used as nutritional sources or supplements. Such uses include without limitation use as a protein or polypeptide or amino acid supplement, use as a carbon source, use as a nitrogen source and use as a source of carbohydrate. In such cases the protein, polypeptide, or polynucleotide of the invention can be added to the feed of a particular organism or can be administered as a separate solid or liquid preparation, such as in the form of powder, pills, solutions, suspensions or capsules. In the case of microorganisms, the protein, polypeptide, or polynucleotide of the invention can be added to the medium in or on which the microorganism is cultured.

A protein or polypeptide of the present invention may exhibit cytokine, cell proliferation (either inducing or inhibiting) or cell differentiation (either inducing or inhibiting) activity or may induce production of other cytokines in certain cell populations, or may be an antagonist or agonist of any of the above. A polynucleotide of the invention can encode a polypeptide exhibiting such attributes. Many protein factors discovered to date, including all known cytokines, have exhibited activity in one or more factor-dependent cell proliferation assays, and hence the assays serve as a convenient confirmation of cytokine agonist or antagonist activity. The activity of a protein or polypeptide of the present invention is evidenced by any one of a number of routine factor dependent cell proliferation assays for cell lines including, without limitation, 32D, DA2, DA1G, T10, B9, B9/11, BaF3, MC9/G, M+(preB M+), 2E8, RB5, DA1, 123, T1165, HT2, CTLL2, TF-1, Mo7e and CMK.

The activity of a protein or polypeptide of the invention may, among other means, be measured by the following methods:

Assays for T-cell or thymocyte proliferation include without limitation those described in: Current Protocols in Immunology, Ed by J. E. coligan, A. M. Kruisbeek, D. H. Margulies, E. M. Shevach, W. Strober, Pub. Greene Publishing Associates and Wiley-Interscience (Chapter 3, In vitro assays for Mouse Lymphocyte Function 3.1-3.19; Chapter 7, Immunologic studies in Humans); Takai et al., J. Immunol. 137:3494-3500, 1986; Bertagnolli et al., J. Immunol. 145:1706-1712, 1990; Bertagnolli et al., Cellular Immunology 133:327-341, 1991; Bertagnolli, et al., I. Immunol. 149:3778-3783, 1992; Bowman et al., I. Immunol. 152: 1756-1761, 1994.

Assays for cytokine production and/or proliferation of spleen cells, lymph node cells or thymocytes include, without limitation, those described in: Polyclonal T cell stimulation, Kruisbeek, A. M. and Shevach, E. M. In Current Protocols in Immunology. J. E. e.a. Coligan eds. Vol 1 pp. 3.12.1-3.12.14, John Wiley and Sons, Toronto. 1994; and Measurement of mouse and human interleukin .gamma., Schreiber, R. D. In Current Protocols in Immunology. J. E. e.a. Coligan eds. Vol 1 pp. 6.8.1-6.8.8, John Wiley and Sons, Toronto. 1994.

Assays for proliferation and differentiation of hematopoietic and lymphopoietic cells include, without limitation, those described in: Measurement of Human and Murine Interleukin 2 and Interleukin 4, Bottomly, K., Davis, L. S. and Lipsky, P. E. In Current Protocols in Immunology. J. E. e.a. Coligan eds. Vol 1 pp. 6.3.1-6.3.12, John Wiley and Sons, Toronto. 1991; deVries et al., J. Exp. Med. 173:1205-1211, 1991; Moreau et al., Nature 336:690-692, 1988; Greenberger et al., Proc. Natl. Acad. Sci. U.S.A. 80:2931-2938, 1983; Measurement of mouse and human interleukin 6—Nordan, R. In Current Protocols in Immunology. J. E. e.a. Coligan eds. Vol 1 pp. 6.6.1-6.6.5, John Wiley and Sons, Toronto. 1991; Smith et al., Proc. Natl. Aced. Sci. U.S.A. 83:1857-1861, 1986; Measurement of human Interleukin 11—Bennett, F., Giannotti, J., Clark, S. C. and Turner, K. J. In Current Protocols in Immunology. J. E. e.a. Coligan eds. Vol 1 pp. 6.15.1 John Wiley and Sons, Toronto. 1991; Measurement of mouse and human Interleukin 9—Ciarletta, A., Giannotti, J., Clark, S. C. and Turner, K. J. In Current Protocols in Immunology. J. E. e.a. Coligan eds Vol 1 pp. 6.13.1, John Wiley and Sons, Toronto. 1991.

Assays for T-cell clone responses to antigens (which will identify, among others, proteins that affect APC-T cell interactions as well as direct T-cell effects by measuring proliferation and cytokine production) include, without limitation, those described in: Current Protocols in Immunology, Ed by J. E. Coligan, A. M. Kruisbeek, D. H. Margulies, E. M. Shevach, W Strober, Pub. Greene Publishing Associates and Wiley-Interscience (Chapter 3, In vitro assays for Mouse Lymphocyte Function; Chapter 6, Cytokines and their cellular receptors; Chapter 7, Immunologic studies in Humans); Weinberger et al., Proc. Natl. Acad. Sci. USA 77:6091-6095, 1980; Weinberger et al., Eur. J. Immun. 11:405-411, 1981; Takai et al., J. Immunol. 137:3494-3500, 1986; Takai et al., J. Immunol. 140:508-512, 1988.

In all the above assays, the polypeptide or protein of the invention is added into the assay system and activity of a target cytokine is determined in the presence and absence of the polypeptide or protein of the invention.

Further, the polypeptides of the invention may be used to examine the expression level or presence of a cytokine. In alternate embodiments, the detection of a cytokine or of a the level of a cytokine will be diagnostic for a disease state or condition.

A protein or polypeptide of the present invention may also exhibit immune stimulating or immune suppressing activity, or may be antogonists or agonists of either activity, including without limitation the activities for which assays are described herein. A polynucleotide of the invention can encode a polypeptide or protein exhibiting such activities. A protein or polypeptide of the invention may be useful in the treatment and/or detection (e.g., a diagnostic) of various immune deficiencies and disorders (including severe combined immunodeficiency (SCID)), e.g., in regulating (up or down) growth and proliferation of T and/or B lymphocytes, as well as effecting the cytolytic activity of NK cells and other cell populations. These immune deficiencies may be genetic or be caused by viral (e.g., HIV) as well as bacterial or fungal infections, or may result from autoimmune disorders. More specifically, infectious diseases caused by viral, bacterial, fungal or other infections may be treatable or detectable (e.g., a diagnostic test) using a protein or polypeptide of the present invention, including infections by HIV, hepatitis viruses, herpesviruses, mycobacteria, *Leishmania* spp., *malaria* spp. and various fungal infections such as candidiasis. Of course, in this regard, a protein or polypeptide of the present invention may also be useful where a boost to the immune system generally may be desirable, i.e., in the treatment of cancer.

Autoimmune disorders which may be treated or detected using a protein or polypeptide of the present invention include, for example, connective tissue disease, multiple sclerosis, systemic lupus erythematosus, rheumatoid arthritis, autoimmune pulmonary inflammation, Guillain-Barre syndrome, autoimmune thyroiditis, insulin dependent diabetes mellitus, myasthenia gravis, graft-versus-host disease and autoimmune inflammatory eye disease. Such a protein or polypeptide of the present invention may also to be useful in the treatment of allergic reactions and conditions, such as asthma (particularly allergic asthma) or other respiratory problems. Other conditions, in which immune suppression is desired (including, for example, organ transplantation), may also be treatable using a protein or polypeptide of the present invention.

Using the proteins or polypeptides of the invention it may also be possible to modulate immune responses, in a number of ways. Down regulation may be in the form of inhibiting or blocking an immune response already in progress or may involve preventing the induction of an immune response. The functions of activated T cells may be inhibited by suppressing T cell responses or by inducing specific tolerance in T cells, or both. Immunosuppression of T cell responses is generally an active, non-antigen-specific, process which requires continuous exposure of the T cells to the suppressive agent. Tolerance, which involves inducing non-responsiveness or anergy in T cells, is distinguishable from immunosuppression in that it is generally antigen-specific and persists after exposure to the tolerizing agent has ceased. Operationally, tolerance can be demonstrated by the lack of a T cell response upon reexposure to specific antigen in the absence of the tolerizing agent.

Down regulating or preventing one or more antigen functions (including without limitation B lymphocyte antigen functions (such as, for example, B7)), e.g., preventing high level lymphokine synthesis by activated T cells, will be useful in situations of tissue, skin and organ transplantation and in graft-versus-host disease (GVHD). For example, blockage of T cell function should result in reduced tissue destruction in tissue transplantation. Typically, in tissue transplants, rejection of the transplant is initiated through its recognition as foreign by T cells, followed by an immune reaction that destroys the transplant. The administration of a molecule which inhibits or blocks interaction of a B7 lymphocyte antigen with its natural ligand(s) on immune cells (such as a soluble, monomeric form of a peptide having B7-2 activity alone or in conjunction with a monomeric form of a peptide having an activity of another B lymphocyte antigen (e.g., B7-1, B7-3) or blocking antibody), prior to transplantation can lead to the binding of the molecule to the natural ligand(s) on the immune cells without transmitting the corresponding costimulatory signal. Blocking B lymphocyte antigen function in this matter prevents cytokine synthesis by immune cells, such as T cells, and thus acts as an immunosuppressant. Moreover, the lack of costimulation may also be sufficient to anergize the T cells, thereby inducing tolerance in a subject. Induction of long-term tolerance by B lymphocyte antigen-blocking reagents may avoid the necessity of repeated administration of these blocking reagents. To achieve sufficient immunosuppression or tolerance in a subject, it may also be necessary to block the function of a combination of B lymphocyte antigens.

The efficacy of particular blocking reagents in preventing organ transplant rejection or GVHD can be assessed using animal models that are predictive of efficacy in humans. Examples of appropriate systems which can be used include allogeneic cardiac grafts in rats and xenogeneic pancreatic islet cell grafts in mice, both of which have been used to examine the immunosuppressive effects of CTLA4Ig fusion proteins in vivo as described in Lenschow et al., Science 257:789-792 (1992) and Turka et al., Proc. Natl. Acad. Sci USA, 89:11102-11105 (1992). In addition, murine models of GVHD (see Paul ed., Fundamental Immunology, Raven Press, New York, 1989, pp. 846-847) can be used to determine the effect of blocking B lymphocyte antigen function in vivo on the development of that disease. Further, the polypeptides of the invention can be used to detect GVHD after organ transplant.

Blocking antigen function may also be therapeutically useful for treating autoimmune diseases. Many autoimmune disorders are the result of inappropriate activation of T cells that are reactive against self tissue and which promote the production of cytokines and autoantibodies involved in the pathology of the diseases. Preventing the activation of autoreactive T cells may reduce or eliminate disease symptoms. Administration of reagents which block costimulation of T cells by disrupting receptor:ligand interactions of B lymphocyte antigens can be used to inhibit T cell activation and prevent production of autoantibodies or T cell-derived cytokines which may be involved in the disease process. Additionally, blocking reagents may induce antigen-specific tolerance of autoreactive T cells which could lead to long-term relief from the disease. The efficacy of blocking reagents in preventing or alleviating autoimmune disorders can be determined using a number of well-characterized animal models of human autoimmune diseases. Examples include murine experimental autoimmune encephalitis, systemic lupus erythmatosis in MRL/lpr/lpr mice or NZB hybrid mice, murine autoimmune collagen arthritis, diabetes mellitus in NOD mice and BB rats, and murine experimental myasthenia gravis (see Paul ed., Fundamental Immunology, Raven Press, New York, 1989, pp. 840-856). Further, polypeptides of the invention can be used to diagnose an immune disorder and/or the susceptibility of an organism for an immune disorder.

Upregulation of an antigen function (preferably a B lymphocyte antigen function), as a means of up regulating immune responses, may also be useful in therapy. Upregulation of immune responses may be in the form of enhancing an existing immune response or eliciting an initial immune response. For example, enhancing an immune response through stimulating B lymphocyte antigen function may be useful in cases of viral infection. In addition, systemic viral diseases such as influenza, the common cold, and encephalitis might be alleviated by the administration of stimulatory forms of B lymphocyte antigens systemically.

Alternatively, anti-vital immune responses may be enhanced in an infected patient by removing T cells from the patient, costimulating the T cells in vitro with viral antigen-pulsed APCs either expressing a peptide of the present invention or together with a stimulatory form of a soluble peptide of the present invention and reintroducing the in vitro activated T cells into the patient. Another method of enhancing anti-viral immune responses would be to isolate infected cells from a patient, transfect them with a nucleic acid encoding a protein or polypeptide of the present invention as described herein such that the cells express all or a portion of the protein or polypeptide on their surface, and reintroduce the transfected cells into the patient. The infected cells would now be capable of delivering a costimulatory signal to, and thereby activate, T cells in vivo.

The presence of a polypeptide or protein of the present invention having the activity of a B lymphocyte antigen(s) on the surface of the tumor cell provides the necessary costimulation signal to T cells to induce a T cell mediated immune response against the transfected tumor cells. In addition, tumor cells which lack MHC class I or MHC class II molecules, or which fail to reexpress sufficient mounts of MHC class I or MHC class II molecules, can be transfected with nucleic acid encoding all or a portion of (e.g., a cytoplasmic-domain truncated portion) of an MHC class I a chain protein and $\beta_2$ microglobulin protein or an MHC class II" chain protein and an MHC class II β chain protein to thereby express MHC class I or MHC class II proteins on the cell surface. Expression of the appropriate class I or class II MHC in conjunction with a peptide having the activity of a B lymphocyte antigen (e.g., B7-1, B7-2, B7-3) induces a T cell mediated immune response against the transfected tumor cell. Optionally, a gene encoding an antisense construct which blocks expression of an MHC class II associated protein, such as the invariant chain, can also be cotransfected with a DNA encoding a peptide having the activity of a B lymphocyte antigen to promote presentation of tumor associated antigens and induce tumor specific immunity. Thus, the induction of a T cell mediated immune response in a human subject may be sufficient to overcome tumor-specific tolerance in the subject.

The activity of a protein or polypeptide of the invention may, among other means, be measured by the following methods:

Suitable assays for thymocyte or splenocyte cytotoxicity include, without limitation, those described in: Current Protocols in Immunology, Ed by J. E. Coligan, A. M. Kruisbeek, D. H. Margulies, E. M. Shevach, W. Strober, Pub. Greene Publishing Associates and Wiley-Interscience (Chapter 3, In vitro assays for Mouse Lymphocyte Function 3.1-3.19; Chapter 7, Immunologic studies in Humans); Herrmann et al., Proc. Natl. Acad. Sci. USA 78:2488-2492, 1981; Herrmann et al., J. Immunol. 128:1968-1974, 1982; Handa et al., J. Immunol. 135:1564-1572, 1985; Takai et al., I. Immunol. 137:3494-3500, 1986; Takai et al., J. Immunol. 140:508-512, 1988; Herrmann et al., Proc. Natl. Acad. Sci. USA 78:2488-2492, 1981; Herrmann et al., J. Immunol. 128:1968-1974, 1982; Handa et al., J. Immunol. 135:1564-1572, 1985; Takai et al., J. Immunol. 137:3494-3500, 1986; Bowman et al., J. Virology 61:1992-1998; Takai et al., J. Immunol. 140:508-512, 1988; Bertagnolli et al., Cellular Immunology 133:327-341, 1991; Brown et al., J. Immunol. 153:3079-3092, 1994.

Assays for T-cell-dependent immunoglobulin responses and isotype switching (which will identify, among others, proteins that modulate T-cell dependent antibody responses and that affect Th1/Th2 profiles) include, without limitation, those described in: Maliszewski, J. Immunol. 144:3028-3033, 1990; and Assays for B cell function: In vitro antibody production, Mond, J. J. and Brunswick, M. In Current Protocols in Immunology. J. E. e.a. Coligan eds. Vol 1 pp. 3.8.1-3.8.16, John Wiley and Sons, Toronto. 1994.

Mixed lymphocyte reaction (MLR) assays (which will identify, among others, proteins that generate predominantly Th1 and CTL responses) include, without limitation, those described in: Current Protocols in Immunology, Ed by J. E. Coligan, A. M. Kruisbeek, D. H. Margulies, E. M. Shevach, W. Strober, Pub. Greene Publishing Associates and Wiley-Interscience (Chapter 3, In vitro assays for Mouse Lymphocyte Function 3.1-3.19; Chapter 7, Immunologic studies in Humans); Takai et al., J. Immunol. 137:3494-3500, 1986; Takai et al., J. Immunol. 140:508-512, 1988; Bertagnolli et al., J. Immunol. 149:3778-3783, 1992.

Dendritic cell-dependent assays (which will identify, among others, proteins expressed by dendritic cells that activate naive T-cells) include, without limitation, those described in: Guery et al., J. Immunol. 134:536-544, 1995; Inaba et al., Journal of Experimental Medicine 173:549-559, 1991; Macatonia et al., Journal of Immunology 154:5071-5079, 1995; Porgador et al., Journal of Experimental Medicine 182:255-260, 1995; Nair et al., Journal of Virology 67:4062-4069, 1993; Huang et al., Science 264:961-965, 1994; Macatonia et al., Journal of Experimental Medicine 169:1255-1264, 1989; Bhardwaj et al., Journal of Clinical Investigation 94:797-807, 1994; and Inaba et al., Journal of Experimental Medicine 172:631-640, 1990.

Assays for lymphocyte survival/apoptosis (which will identify, among others, proteins that prevent apoptosis after superantigen induction and proteins that regulate lymphocyte homeostasis) include, without limitation, those described in: Darzynkiewicz et al., Cytometry 13:795-808, 1992; Gorczyca et al., Leukemia 7:659-670, 1993; Gorczyca et al., Cancer Research 53:1945-1951, 1993; Itoh et al., Cell 66:233-243, 1991; Zacharchuk, Journal of Immunology 145:4037-4045, 1990; Zamai et al., Cytometry 14:891-897, 1993; Gorczyca et al., International Journal of Oncology 1:639-648, 1992.

Assays for proteins that influence early steps of T-cell commitment and development include, without limitation, those described in: Antica et al., Blood 84:111-117, 1994; Fine et al., Cellular Immunology 155:111-122, 1994; Galy et al., Blood 85:2770-2778, 1995; Toki et al., Proc. Nat. Acad. Sci. USA 88:7548-7551, 1991.

A protein or polypeptide of the present invention may be useful in regulation of hematopoiesis (as an antagonist or agonist) and, consequently, in the treatment and/or detection (e.g., a diagnostic) of myeloid or lymphoid cell deficiencies. Even marginal biological activity in support of colony forming cells or of factor-dependent cell lines indicates involvement in regulating hematopoiesis, e.g., in supporting the growth and proliferation of erythroid progenitor cells alone or in combination with other cytokines, thereby indicating utility, for example, in treating and/or detecting (e.g., a diagnostic) various anemias or for use in conjunction with irradiation/chemotherapy to stimulate the production of erythroid precursors and/or erythroid cells; in supporting the growth and proliferation of myeloid cells such as granulocytes and monocytes/macrophages (i.e., traditional CSF activity), for example, in conjunction with chemotherapy to prevent or treat consequent myelo-suppression; in supporting the growth and proliferation of megakaryocytes and consequently of platelets thereby allowing prevention or treatment of various platelet disorders such as thrombocytopenia, and generally for use in place of or complimentary to platelet transfusions; and/or in supporting the growth and proliferation of hematopoietic stem cells which are capable of maturing to any and all of the above-mentioned hematopoietic cells and therefore find therapeutic utility in various stem cell disorders (such as those usually treated with transplantation, including, without limitation, aplastic anemia and paroxysmal nocturnal hemoglobinuria), as well as in repopulating the stem cell compartment post irradiation/chemotherapy, either in-vivo or ex-vivo (i.e., in conjunction with bone marrow transplantation or with peripheral progenitor cell transplantation (homologous or heterologous)) as normal cells or genetically manipulated for gene therapy.

The activity of a protein or polypeptide of the invention may, among other means, be measured by the following methods:

Suitable assays for proliferation and differentiation of various hematopoietic lines are cited above.

Assays for embryonic stem cell differentiation (which will identify, among others, proteins that influence embryonic differentiation hematopoiesis) include, without limitation, those described in: Johansson et al. Cellular Biology 15:141-151, 1995; Keller et al., Molecular and Cellular Biology 13:473-486, 1993; McClanahan et al., Blood 81:2903-2915, 1993.

Assays for stem cell survival and differentiation (which will identify, among others, proteins that regulate lympho-hematopoiesis) include, without limitation, those described in: Methylcellulose colony forming assays, Freshney, M. G. In Culture of Hematopoietic Cells. R. I. Freshney, et al. eds. Vol pp. 265-268, Wiley-Liss, Inc., New York, N.Y. 1994; Hirayama et al., Proc. Natl. Acad. Sci. USA 89:5907-5911, 1992; Primitive hematopoietic colony forming cells with high proliferative potential, McNiece, I. K. and Briddell, R. A. In Culture of Hematopoietic Cells. R. I. Freshney, et al. eds. Vol pp. 23-39, Wiley-Liss, Inc., New York, N.Y. 1994; Neben et al., Experimental Hematology 22:353-359, 1994; Cobblestone area forming cell assay, Ploemacher, R. E. In Culture of Hematopoietic Cells. R. I. Freshney, et al. eds. Vol pp. 1-21, Wiley-Liss, Inc., New York, N.Y. 1994; Long term bone marrow cultures in the presence of stromal cells, Spooncer, E., Dexter, M. and Allen, T. In Culture of Hematopoietic Cells. R. I. Freshney, et al. eds. Vol pp. 163-179, Wiley-Liss, Inc., New York, N.Y. 1994; Long term culture initiating cell assay, Sutherland, H. J. In Culture of Hematopoietic Cells. R. I. Freshney, et al. eds. Vol pp. 139-162, Wiley-Liss, Inc., New York, N.Y. 1994.

A protein or polypeptide of the present invention also may have utility in compositions used for bone, cartilage, tendon, ligament and/or nerve tissue growth or regeneration, as well as for wound healing and tissue repair and replacement, and in the treatment of burns, incisions and ulcers (as an antagonist or agonist).

A protein or polypeptide of the present invention, which acts as an antagonist or agonist of cartilage and/or bone growth, has application in the healing of bone fractures and cartilage damage or defects in humans and other animals. Such a preparation employing a protein or polypeptide of the invention may have prophylactic use in closed as well as open fracture reduction and also in the improved fixation of artificial joints. De novo bone formation induced by an osteogenic agent contributes to the repair of congenital, trauma induced, or oncologic resection induced craniofacial defects, and also is useful in cosmetic plastic surgery.

A protein or polypeptide of this invention may also be used in the treatment and/or detection (e.g., a diagnostic) of periodontal disease, and in other tooth repair processes. Such agents may provide an environment to attract bone-forming cells, stimulate growth of bone-forming cells or induce differentiation of progenitors of bone-forming cells. A protein or polypeptide of the invention may also be useful in the treatment of osteoporosis or osteoarthritis, such as through stimulation of bone and/or cartilage repair or by blocking inflammation or processes of tissue destruction (collagenase activity, osteoclast activity, etc.) mediated by inflammatory processes.

Another category of tissue regeneration activity that may be attributable to the protein or polypeptide of the present invention is tendon/ligament formation. A protein or polypeptide of the present invention, which induces tendon/ligament-like tissue or other tissue formation in circumstances where such tissue is not normally formed, has application in the healing of tendon or ligament tears, deformities and other tendon or ligament defects in humans and other animals. Such a preparation employing a tendon/ligament-like tissue inducing protein (as an antagonist or agonist) may have prophylactic use in preventing damage to tendon or ligament tissue, as well as use in the improved fixation of tendon or ligament to bone or other tissues, and in repairing defects to tendon or ligament tissue. De novo tendon/ligament-like tissue formation induced by a composition of the present invention contributes to the repair of congenital, trauma induced, or other tendon or ligament defects of other origin, and is also useful in cosmetic plastic surgery for attachment or repair of tendons or ligaments. The compositions of the present invention may provide environment to attract tendon- or ligament-forming cells, stimulate growth of tendon- or ligament-forming cells, induce differentiation of progenitors of tendon- or ligament-forming cells, or induce growth of tendon/ligament cells or progenitors ex vivo for return in vivo to effect tissue repair. The compositions of the invention may also be useful in the treatment of tendinitis, carpal tunnel syndrome and other tendon or ligament defects. The compositions may also include an appropriate matrix and/or sequestering agent as a carrier as is well known in the art.

The protein or polypeptide of the present invention may also be useful for proliferation of neural cells and for regeneration of nerve and brain tissue, i.e., for the treatment and/or detection (e.g., a diagnostic) of central and peripheral nervous system diseases and neuropathies, as well as mechanical and traumatic disorders, which involve degeneration, death or trauma to neural cells or nerve tissue. More specifically, a protein or polypeptide may be used in the treatment and/or detection (e.g., a diagnostic) of diseases of the peripheral nervous system, such as peripheral nerve injuries, peripheral neuropathy and localized neuropathies, and central nervous system diseases, such as Alzheimer's, Parkinson's disease, Huntington's disease, amyotrophic lateral sclerosis, and Shy-Drager syndrome. Further conditions which may be treated in accordance with the present invention include mechanical and traumatic disorders, such as spinal cord disorders, head trauma and cerebrovascular diseases such as stroke. Peripheral neuropathies resulting from chemotherapy or other medical therapies may also be treatable using a protein or polypeptide of the invention.

Proteins or polypeptides of the invention may also be useful to promote better or faster closure of non-healing wounds, including without limitation pressure ulcers, ulcers associated with vascular insufficiency, surgical and traumatic wounds, and the like.

It is expected that a protein or polypeptide of the present invention may also exhibit activity for generation or regeneration of other tissues, such as organs (including, for example, pancreas, liver, intestine, kidney, skin, endothelium), muscle (smooth, skeletal or cardiac) and vascular (including vascular endothelium) tissue, or for promoting the growth of cells comprising such tissues. Part of the desired effects may be by inhibition or modulation of fibrotic scarring to allow normal tissue to regenerate. A protein or polypeptide of the invention may also exhibit angiogenic activity.

A protein or polypeptide of the present invention may also be useful for gut protection or regeneration and treatment of lung or liver fibrosis, reperfusion injury in various tissues, and conditions resulting from systemic cytokine damage.

A protein or polypeptide of the present invention may also be useful for promoting or inhibiting differentiation of tissues described above from precursor tissues or cells; or for inhibiting the growth of tissues described above.

The activity of a protein or polypeptide of the invention may, among other means, be measured by the following methods:

Assays for tissue generation activity include, without limitation, those described in: International Patent Publication No. WO95/16035 (bone, cartilage, tendon); International Patent Publication No. WO95/05846 (nerve, neuronal); International Patent Publication No. WO91/07491 (skin, endothelium).

Assays for wound healing activity include, without limitation, those described in: Winter, Epidermal Wound Healing, pps. 71-112 (Maibach, H. I. and Rovee, D. T., eds.), Year Book Medical Publishers, Inc., Chicago, as modified by Eaglstein and Mertz, J. Invest. Dermatol 71:382-84 (1978).

A protein or polypeptide of the present invention may also exhibit agonist or antagonist activity against activin- or inhibin-related activities. Inhibins are characterized by their ability to inhibit the release of follicle stimulating hormone (FSH), while activins and are characterized by their ability to stimulate the release of follicle stimulating hormone (FSH). Thus, a protein or polypeptide of the present invention that are agonists of inhibin, may be useful as a contraceptive based on the ability of inhibins to decrease fertility in female mammals and decrease spermatogenesis in male mammals. Additionally, the proteins or polypeptides of the invention that are antagonists of activin, may be useful as a contraceptive based on the ability of activin molecules in stimulating FSH release from cells of the anterior pituitary. Alternatively, the protein or polypeptide of the invention that are agonists of activin, may be useful as a fertility inducing therapeutic, based upon the ability of activin molecules in stimulating FSH release from cells of the anterior pituitary. See, for example, U.S. Pat. No. 4,798,885. Further, a proteins or polypeptides of the present invention that are antagonists of inhibin, may be useful as a fertility inducing therapeutic, based upon the ability of inhibins to decrease fertility in female mammals and decrease spermatogenesis in male mammals. A protein or polypeptide of the invention may also be useful for advancement of the onset of fertility in sexually immature mammals, so as to increase the lifetime reproductive performance of domestic animals such as cows, sheep and pigs.

The activity of a protein or polypeptide of the invention may, among other means, be measured by the following methods:

Assays for activin/inhibin activity include, without limitation, those described in: Vale et al., Endocrinology 91:562-572, 1972; Ling et al., Nature 321:779-782, 1986; Vale et al., Nature 321:776-779, 1986; Mason et al., Nature 318:659-663, 1985; Forage et al., Proc. Natl. Acad. Sci. USA 83:3091-3095, 1986.

A protein or polypeptide of the present invention may be an antogonist or agonist of chemotactic or chemokinetic activity (e.g., act as a chemokine) for mammalian cells, including, for example, monocytes, fibroblasts, neutrophils, T-cells, mast cells, eosinophils, epithelial and/or endothelial cells. Chemotactic and chemokinetic proteins can be used to mobilize or attract a desired cell population to a desired site of action. Antagonists or agonists of chemotactic or chemokinetic proteins provide particular advantages in treatment of inflammation, or wounds and other trauma to tissues, as well as in treatment of localized infections. For example, attraction of lymphocytes, monocytes or neutrophils to tumors or sites of infection may result in improved immune responses against the tumor or infecting agent.

A protein or polypeptide or peptide is an agonist of chemotactic activity for a particular cell population if it can stimulate, directly or indirectly, the directed orientation or movement of such cell population. Preferably, the protein or polypeptide or peptide has the ability to directly stimulate directed movement of cells. Whether a particular protein has chemotactic activity for a population of cells can be readily determined by employing such protein or peptide in any known assay for cell chemotaxis.

The activity of a protein or polypeptide of the invention may, among other means, be measured by the following methods:

Assays for chemotactic activity (which will identify proteins that induce or prevent chemotaxis) consist of assays that measure the ability of a protein to induce the migration of cells across a membrane as well as the ability of a protein to induce the adhesion of one cell population to another cell population. Suitable assays for movement and adhesion include, without limitation, those described in: Current Protocols in Immunology, Ed by J. E. Coligan, A. M. Kruisbeek, D. H. Marguiles, E. M. Shevach, W. Strober, Pub. Greene Publishing Associates and Wiley-Interscience (Chapter 6.12, Measurement of alpha and beta Chemokines 6.12.1-6.12.28; Taub et al. J. Clin. Invest. 95:1370-1376, 1995; Lind et al. APMIS 103:140-146, 1995; Muller et al Eur. J. Immunol. 25:1744-1748; Gruber et al., J. of Immunol. 152:5860-5867, 1994; Johnston et al., J. of Immunol. 153:1762-1768, 1994.

A protein or polypeptide of the invention may also be an antagonist or agonist of hemostatic or thrombolytic activity. Such a protein or polypeptide is expected to be useful in treatment and/or detection (e.g., a diagnostic) of various coagulation disorders (including hereditary disorders, such as hemophilias) or to enhance coagulation and other hemostatic events in treating wounds resulting from trauma, surgery or other causes. A protein or polypeptide of the invention may also be useful for dissolving or inhibiting formation of thromboses and for treatment and prevention of conditions resulting therefrom (such as, for example, infarction of cardiac and central nervous system vessels (e.g., stroke).

The activity of a protein or polypeptide of the invention may, among other means, be measured by the following methods:

Assay for hemostatic and thrombolytic activity include, without limitation, those described in: Linet et al., J. Clin. Pharmacol. 26:131-140, 1986; Burdick et al., Thrombosis Res. 45:413-419, 1987; Humphrey et al., Fibrinolysis 5:71-79 (1991); Schaub, Prostaglandins 35:467-474, 1988.

A protein or polypeptide of the present invention may also demonstrate activity as receptors, receptor ligands or antagonists or agonists of receptor/ligand interactions. Examples of such receptors and ligands include, without limitation, cytokine receptors and their ligands, receptor kinases and their ligands, receptor phosphatases and their ligands, receptors involved in cell-cell interactions and their ligands (including without limitation, cellular adhesion molecules (such as selectins, integrins and their ligands) and receptor/ligand pairs involved in antigen presentation, antigen recognition and development of cellular and humoral immune responses). Receptors and ligands are also useful for screening of potential peptide or small molecule inhibitors of the relevant receptor/ligand interaction. A protein or polypeptide of the present invention (including, without limitation, fragments of receptors and ligands) may themselves be useful as inhibitors of receptor/ligand interactions.

The activity of a protein or polypeptide of the invention may, among other means, be measured by the following methods:

Suitable assays for receptor-ligand activity include without limitation those described in: Current Protocols in Immunology, Ed by J. E. Coligan, A. M. Kruisbeek, D. H. Margulies, E. M. Shevach, W. Strober, Pub. Greene Publishing Associates and Wiley-Interscience (Chapter 7.28, Measurement of Cellular Adhesion under static conditions 7.28.1-7.28.22), Takai et al., Proc. Natl. Acad. Sci. USA 84:6864-6868, 1987; Bierer et al., J. Exp. Med. 168:1145-1156, 1988; Rosenstein et al., J. Exp. Med. 169:149-160 1989; Stoltenborg et al., J. Immunol. Methods 175:59-68, 1994; Stitt et al., Cell 80:661-670, 1995.

Proteins or polypeptides of the present invention may also be antagonists or agonists of inflammation. Anti-inflammatory activity may be achieved by providing a stimulus to cells involved in the inflammatory response, by inhibiting or promoting cell-cell interactions (such as, for example, cell adhesion), by inhibiting or promoting chemotaxis of cells involved in the inflammatory process, inhibiting or promoting cell extravasation, or by stimulating or suppressing production of other factors which more directly inhibit or promote an inflammatory response. Proteins or polypeptides of the invention can be used to treat and/or detect (e.g., a diagnostic) inflammatory conditions including chronic or acute conditions, including without limitation intimation associated with infection (such as septic shock, sepsis or systemic inflammatory response syndrome (SIRS)), ischemia-reperfusion injury, endotoxin lethality, arthritis, complement-mediated hyperacute rejection, nephritis, cytokine or chemokine-induced lung injury, inflammatory bowel disease, Crohn's disease or resulting from over production of cytokines such as TNF or IL-1. Proteins or polypeptides of the invention may also be useful to treat anaphylaxis and hypersensitivity to an antigenic substance or material.

Nervous system disorders, which can be treated and/or detected (e.g., a diagnostic) with the polypeptides or proteins of the invention include but are not limited to nervous system injuries, and diseases or disorders which result in either a disconnection of axons, a diminution or degeneration of neurons, or demyelination. Nervous system lesions which may be treated and/or detected (e.g., a diagnostic) in a patient (including human and non-human mammalian patients) according to the invention include but are not limited to the following lesions of either the central (including spinal cord, brain) or peripheral nervous systems:
  (i) traumatic lesions, including lesions caused by physical injury or associated with surgery, for example, lesions which sever a portion of the nervous system, or compression injuries;
  (ii) ischemic lesions, in which a lack of oxygen in a portion of the nervous system results in neuronal injury or death, including cerebral infarction or ischemia, or spinal cord infarction or ischemia;
  (iii) malignant lesions, in which a portion of the nervous system is destroyed or injured by malignant tissue which is either a nervous system associated malignancy or a malignancy derived from non-nervous system tissue;
  (iv) infectious lesions, in which a portion of the nervous system is destroyed or injured as a result of infection, for example, by an abscess or associated with infection by human immunodeficiency virus, herpes zoster, or herpes simplex virus or with Lyme disease, tuberculosis, syphilis;
  (v) degenerative lesions, in which a portion of the nervous system is destroyed or injured as a result of a degenerative process including but not limited to degeneration associated with Parkinson's disease, Alzheimer's disease, Huntington's chorea, or amyotrophic lateral sclerosis;
  (vi) lesions associated with nutritional diseases or disorders, in which a portion of the nervous system is destroyed or injured by a nutritional disorder or disorder of metabolism including but not limited to, vitamin B12 deficiency, folic acid deficiency, Wernicke disease, tobacco-alcohol amblyopia, Marchiafava-Bignami disease (primary degeneration of the corpus callosum), and alcoholic cerebellar degeneration;
  (vii) neurological lesions associated with systemic diseases including but not limited to diabetes (diabetic neuropathy, Bell's palsy), systemic lupus erythematosus, carcinoma, or sarcoidosis;
  (viii) lesions caused by toxic substances including alcohol, lead, or particular neurotoxins; and
  (ix) demyelinated lesions in which a portion of the nervous system is destroyed or injured by a demyelinating disease including but not limited to multiple sclerosis, human immunodeficiency virus-associated myelopathy, transverse myelopathy or various etiologies, progressive multifocal leukoencephalopathy, and central pontine myelinolysis.

Therapeutics which are useful according to the invention for treatment of a nervous system disorder may be selected by testing for biological activity in promoting the survival or differentiation of neurons. For example, and not by way of limitation, therapeutics which elicit any of the following effects may be useful according to the invention:
  (i) increased survival time of neurons in culture;
  (ii) increased sprouting of neurons in culture or in vivo;
  (iii) increased production of a neuron-associated molecule in culture or in vivo, e.g., choline acetyltransferase or acetylcholinesterase with respect to motor neurons; or
  (iv) decreased symptoms of neuron dysfunction in vivo.

Such effects may be measured by any method known in the art. In preferred, non-limiting embodiments, increased survival of neurons may be measured by the method set forth in Arakawa et al. (1990, J. Neurosci. 10:3507-3515); increased sprouting of neurons may be detected by methods set forth in Pestronk et al. (1980, Exp. Neurol. 70:65-82) or Brown et al. (1981, Ann. Rev. Neurosci. 4:17-42); increased production of neuron-associated molecules may be measured by bioassay, enzymatic assay, antibody binding, Northern blot assay, etc., depending on the molecule to be measured; and motor neuron dysfunction may be measured by assessing the physical manifestation of motor neuron disorder, e.g., weakness, motor neuron conduction velocity, or functional disability.

In a specific embodiments, motor neuron disorders that may be treated and/or detected (e.g., a diagnostic) according to the invention include but are not limited to disorders such as infarction, infection, exposure to toxin, trauma, surgical damage, degenerative disease or malignancy that may affect motor neurons as well as other components of the nervous system, as well as disorders that selectively affect neurons such as amyotrophic lateral sclerosis, and including but not limited to progressive spinal muscular atrophy, progressive bulbar palsy, primary lateral sclerosis, infantile and juvenile muscular atrophy, progressive bulbar paralysis of childhood (Fazio-Londe syndrome), poliomyelitis and the post polio syndrome, and Hereditary Motorsensory Neuropathy (Charcot-Marie-Tooth Disease).

A protein or polypeptide of the invention may also exhibit one or more of the following additional activities or effects: inhibiting the growth, infection or function of, or killing, infectious agents, including, without limitation, bacteria, viruses, fungi and other parasites; effecting (suppressing or enhancing) bodily characteristics or plant characteristics, including, without limitation, height, weight, hair color, eye color, skin, fat to lean ratio or other tissue pigmentation, or organ or body part size or shape (such as, for example, breast augmentation or diminution, change in bone form or shape); effecting biorhythms or caricadic cycles or rhythms; effecting the fertility of male or female subjects; effecting the metabolism, catabolism, anabolism, processing, utilization, storage or elimination of dietary fat, lipid, protein, carbohydrate, vitamins, minerals, co-factors or other nutritional factors or component(s); effecting behavioral characteristics, including, without limitation, appetite, libido, stress, cognition (including cognitive disorders), depression (including depressive disorders) and violent behaviors; providing analgesic effects or other pain reducing effects; promoting differentiation and growth of embryonic stem cells in lineages other than hematopoietic lineages; hormonal or endocrine activity; in the case of enzymes, correcting deficiencies of the enzyme and treating deficiency-related diseases; treatment of hyperproliferative disorders (such as, for example, psoriasis); immunoglobulin-like activity (such as, for example, the ability to bind antigens or complement); and the ability to act as an antigen in a vaccine composition to raise an immune response against such protein or another material or entity which is cross-reactive with such protein.

A protein or polypeptide of the present invention (from whatever source derived, including without limitation from recombinant and non-recombinant sources) may be administered to a patient in need, by itself, or in pharmaceutical compositions where it is mixed with suitable carriers or excipient(s) at doses to treat or ameliorate a variety of disorders. Such a composition may also contain (in addition to protein or polypeptide and a carrier) diluents, fillers, salts, buffers, stabilizers, solubilizers, and other materials well known in the art. The term "pharmaceutically acceptable" means a non-toxic material that does not interfere with the effectiveness of the biological activity of the active ingredient(s). The characteristics of the carrier will depend on the route of administration. The pharmaceutical composition of the invention may also contain cytokines, lymphokines, or other hematopoietic factors such as M-CSF, GM-CSF, INF, IL-1, IL-2, IL-3, IL-4, IL-5, IL-6, IL-7, IL-8, IL-9, IL-10, IL-11, IL-12, IL-13, IL-14, IL-15, IFN, TNF0, TNF1, TNF2, G-CSF, Meg-CSF, thrombopoietin, stem cell factor, and erythropoietin. The pharmaceutical composition may further contain other agents which either enhance the activity of the protein or polypeptide or compliment its activity or use in treatment. Such additional factors and/or agents may be included in the pharmaceutical composition to produce a synergistic effect with protein or polypeptide of the invention, or to minimize side effects. Conversely, protein or polypeptide of the present invention may be included in formulations of the particular cytokine, lymphokine, other hematopoietic factor, thrombolytic or anti-thrombotic factor, or anti-inflammatory agent to minimize side effects of the cytokine, lymphokine, other hematopoietic factor, thrombolytic or anti-thrombotic factor, or anti-inflammatory agent. A protein or polypeptide of the present invention may be active in multimers (e.g., heterodimers or homodimers) or complexes with itself or other proteins. As a result, pharmaceutical compositions of the invention may comprise a protein or polypeptide of the invention in such multimeric or complexed form.

Techniques for formulation and administration of the compounds of the instant application may be found in "Remington's Pharmaceutical Sciences," Mack Publishing Co., Easton, Pa., latest edition. A therapeutically effective dose further refers to that amount of the compound sufficient to result in amelioration of symptoms, e.g., treatment, healing, prevention or amelioration of the relevant medical condition, or an increase in rate of treatment, healing, prevention or amelioration of such conditions. When applied to an individual active ingredient, administered alone, a therapeutically effective dose refers to that ingredient alone. When applied to a combination, a therapeutically effective dose refers to combined amounts of the active ingredients that result in the therapeutic effect, whether administered in combination, serially or simultaneously.

In practicing the method of treatment or use of the present invention, a therapeutically effective amount of protein or polypeptide of the present invention is administered to a mammal having a condition to be treated. Protein or polypeptide of the present invention may be administered in accordance with the method of the invention either alone or in combination with other therapies such as treatments employing cytokines, lymphokines or other hematopoietic factors. When co-administered with one or more cytokines, lymphokines or other hematopoietic factors, protein or polypeptide of the prese effective amount of protein or polypeptide of the present invention is administered to a mammal having a condition to be treated. Protein or polypeptide of the present invention may be administered in accordance with the method of the invention either alone or in combination with other therapies such as treatments employing cytokines, lymphokines or other hematopoietic factors. When co-administered with one or more cytokines, lymphokines or other hematopoietic factors, protein or polypeptide of the preseoutes of administration may, for example, include oral, rectal, transmucosal, or intestinal administration; parenteral delivery, including intramuscular, subcutaneous, intramedullary injections, as well as intrathecal, direct intraventricular, intravenous, intraperitoneal, intranasal, or intraocular injections. Administration of protein or polypeptide of the present invention used in the pharmaceutical composition or to practice the method of the present invention can be carried out in a variety of conventional ways, such as oral ingestion, inhalation, topical application or cutaneous, subcutaneous, intraperitoneal, parenteral or intravenous injection. Intravenous administration to the patient is preferred.

Alternately, one may administer the compound in a local rather than systemic manner, for example, via injection of the compound directly into a arthritic joints or in fibrotic tissue, often in a depot or sustained release formulation. In order to prevent the scarring process frequently occurring as complication of glaucoma surgery, the compounds may be administered topically, for example, as eye drops. Furthermore, one may administer the drug in a targeted drug delivery system, for example, in a liposome coated with a specific antibody, targeting, for example, arthritic or fibrotic tissue. The liposomes will be targeted to and taken up selectively by the afflicted tissue.

Pharmaceutical compositions for use in accordance with the present invention thus may be formulated in a conventional manner using one or more physiologically acceptable carriers comprising excipients and auxiliaries which facilitate processing of the active compounds into preparations which can be used pharmaceutically. These pharmaceutical compositions may be manufactured in a manner that is itself known, e.g., by means of conventional mixing, dissolving, granulating, dragee-making, levigating, emulsifying, encapsulating, entrapping or lyophilizing processes. Proper formulation is dependent upon the route of administration chosen. When a therapeutically effective amount of protein or polypeptide of the present invention is administered orally, protein or polypeptide of the present invention will be in the form of a tablet, capsule, powder, solution or elixir. When administered in tablet form, the pharmaceutical composition of the invention may additionally contain a solid carrier such as a gelatin or an adjuvant. The tablet, capsule, and powder contain from about 5 to 95% protein or polypeptide of the present invention, and preferably from about 25 to 90% protein or polypeptide of the present invention. When administered in liquid form, a liquid carrier such as water, petroleum, oils of animal or plant origin such as peanut oil, mineral oil, soybean oil, or sesame oil, or synthetic oils may be added. The liquid form of the pharmaceutical composition may further contain physiological saline solution, dextrose or other saccharide solution, or glycols such as ethylene glycol, propylene glycol or polyethylene glycol. When administered in liquid form, the pharmaceutical composition contains from about 0.5 to 90% by weight of protein or polypeptide of the present invention, and preferably from about 1 to 50% protein or polypeptide of the present invention.

When a therapeutically effective amount of protein or polypeptide of the present invention is administered by intravenous, cutaneous or subcutaneous injection, protein or polypeptide of the present invention will be in the form of a pyrogen-free, parenterally acceptable aqueous solution. The preparation of such parenterally acceptable protein solutions, having due regard to pH, isotonicity, stability, and the like, is within the skill in the art. A preferred pharmaceutical composition for intravenous, cutaneous, or subcutaneous injection should contain, in addition to protein or polypeptide of the present invention, an isotonic vehicle such as Sodium Chloride Injection, Ringer's Injection, Dextrose Injection, Dextrose and Sodium Chloride Injection, Lactated Ringer's Injection, or other vehicle as known in the art. The pharmaceutical composition of the present invention may also contain stabilizers, preservatives, buffers, antioxidants, or other additives known to those of skill in the art. For injection, the agents of the invention may be formulated in aqueous solutions, preferably in physiologically compatible buffers such as Hanks's solution, Ringer's solution, or physiological saline buffer. For transmucosal administration, penetrants appropriate to the barrier to be permeated are used in the formulation. Such penetrants are generally known in the art.

For oral administration, the compounds can be formulated readily by combining the active compounds with pharmaceutically acceptable carriers well known in the art. Such carriers enable the compounds of the invention to be formulated as tablets, pills, dragees, capsules, liquids, gels, syrups, slurries, suspensions and the like, for oral ingestion by a patient to be treated. Pharmaceutical preparations for oral use can be obtained solid excipient, optionally grinding a resulting mixture, and processing the mixture of granules, after adding suitable auxiliaries, if desired, to obtain tablets or dragee cores. Suitable excipients are, in particular, fillers such as sugars, including lactose, sucrose, mannitol, or sorbitol; cellulose preparations such as, for example, maize starch, wheat starch, rice starch, potato starch, gelatin, gum tragacanth, methyl cellulose, hydroxypropylmethyl-cellulose, sodium carboxymethylcellulose, and/or polyvinylpyrrolidone (PVP). If desired, disintegrating agents may be added, such as the cross-linked polyvinyl pyrrolidone, agar, or alginic acid or a salt thereof such as sodium alginate. Dragee cores are provided with suitable coatings. For this purpose, concentrated sugar solutions may be used, which may optionally contain gum arabic, talc, polyvinyl pyrrolidone, carbopol gel, polyethylene glycol, and/or titanium dioxide, lacquer solutions, and suitable organic solvents or solvent mixtures. Dyestuffs or pigments may be added to the tablets or dragee coatings for identification or to characterize different combinations of active compound doses.

Pharmaceutical preparations which can be used orally include push-fit capsules made of gelatin, as well as soft, sealed capsules made of gelatin and a plasticizer, such as glycerol or sorbitol. The push-fit capsules can contain the active ingredients in admixture with filler such as lactose, binders such as starches, and/or lubricants such as talc or magnesium stearate and, optionally, stabilizers. In soft capsules, the active compounds may be dissolved or suspended in suitable liquids, such as fatty oils, liquid paraffin, or liquid polyethylene glycols. In addition, stabilizers may be added. All formulations for oral administration should be in dosages suitable for such administration. For buccal administration, the compositions may take the form of tablets or lozenges formulated in conventional manner.

For administration by inhalation, the compounds for use according to the present invention are conveniently delivered in the form of an aerosol spray presentation from pressurized packs or a nebuliser, with the use of a suitable propellant, e.g., dichlorodifluoromethane, trichlorofluoromethane, dichlorotetrafluoroethane, carbon dioxide or other suitable gas. In the case of a pressurized aerosol the dosage unit may be determined by providing a valve to deliver a metered amount. Capsules and cartridges of, e.g., gelatin for use in an inhaler or insufflator may be formulated containing a powder mix of the compound and a suitable powder base such as lactose or starch. The compounds may be formulated for parenteral administration by injection, e.g., by bolus injection or continuous infusion. Formulations for injection may be presented in unit dosage form, e.g., in ampoules or in multi-dose containers, with an added preservative. The compositions may take such forms as suspensions, solutions or emulsions in oily or aqueous vehicles, and may contain formulatory agents such as suspending, stabilizing and/or dispersing agents.

Pharmaceutical formulations for parenteral administration include aqueous solutions of the active compounds in water-soluble form. Additionally, suspensions of the active compounds may be prepared as appropriate oily injection suspensions. Suitable lipophilic solvents or vehicles include fatty oils such as sesame oil, or synthetic fatty acid esters, such as ethyl oleate or triglycerides, or liposomes. Aqueous injection suspensions may contain substances which increase the viscosity of the suspension, such as sodium carboxymethyl cellulose, sorbitol, or dextran. Optionally, the suspension may also contain suitable stabilizers or agents which increase the solubility of the compounds to allow for the preparation of highly concentrated solutions. Alternatively, the active ingredient may be in powder form for constitution with a suitable vehicle, e.g., sterile pyrogen-free water, before use.

The compounds may also be formulated in rectal compositions such as suppositories or retention enemas, e.g., containing conventional suppository bases such as cocoa butter or other glycerides. In addition to the formulations described previously, the compounds may also be formulated as a depot preparation. Such long acting formulations may be administered by implantation (for example subcutaneously or intramuscularly) or by intramuscular injection. Thus, for example, the compounds may be formulated with suitable polymeric or hydrophobic materials (for example as an emulsion in an acceptable oil) or ion exchange resins, or as sparingly soluble derivatives, for example, as a sparingly soluble salt.

A pharmaceutical carrier for the hydrophobic compounds of the invention is a cosolvent system comprising benzyl alcohol, a nonpolar surfactant, a water-miscible organic polymer, and an aqueous phase. The cosolvent system may be the VPD co-solvent system. VPD is a solution of 3% w/v benzyl alcohol, 8% w/v of the nonpolar surfactant polysorbate 80, and 65% w/v polyethylene glycol 300, made up to volume in absolute ethanol. The VPD co-solvent system (VPD:5W) consists of VPD diluted 1:1 with a 5% dextrose in water solution. This co-solvent system dissolves hydrophobic compounds well, and itself produces low toxicity upon systemic administration. Naturally, the proportions of a co-solvent system may be varied considerably without destroying its solubility and toxicity characteristics. Furthermore, the identity of the co-solvent components may be varied: for example, other low-toxicity nonpolar surfactants may be used instead of polysorbate 80; the fraction size of polyethylene glycol may be varied; other biocompatible polymers may replace polyethylene glycol, e.g., polyvinyl pyrrolidone; and other sugars or polysaccharides may substitute for dextrose. Alternatively, other delivery systems for hydrophobic pharmaceutical compounds may be employed. Liposomes and emulsions are well known examples of delivery vehicles or carriers for hydrophobic drugs. Certain organic solvents such as dimethylsulfoxide also may be employed, although usually at the cost of greater toxicity. Additionally, the compounds may be delivered using a sustained-release system, such as semipermeable matrices of solid hydrophobic polymers containing the therapeutic agent. Various of sustained-release materials have been established and are well known by those skilled in the art. Sustained-release capsules may, depending on their chemical nature, release the compounds for a few weeks up to over 100 days. Depending on the chemical nature and the biological stability of the therapeutic reagent, additional strategies for protein stabilization may be employed.

The pharmaceutical compositions also may comprise suitable solid or gel phase carriers or excipients. Examples of such carriers or excipients include but are not limited to calcium carbonate, calcium phosphate, various sugars, starches, cellulose derivatives, gelatin, and polymers such as polyethylene glycols. Many of the proteinase inhibiting compounds of the invention may be provided as salts with pharmaceutically compatible counterions. Such pharmaceutically acceptable base addition salts are those salts which retain the biological effectiveness and properties of the free acids and which are obtained by reaction with inorganic or organic bases such as sodium hydroxide, magnesium hydroxide, ammonia, trialkylamine, dialkylamine, monoalkylamine, dibasic amino acids, sodium acetate, potassium benzoate, triethanol amine and the like.

The pharmaceutical composition of the invention may be in the form of a complex of the protein(s) or polypeptide(s) of present invention along with protein or peptide antigens. The protein and/or peptide antigen will deliver a stimulatory signal to both B and T lymphocytes. B lymphocytes will respond to antigen through their surface immunoglobulin receptor. T lymphocytes will respond to antigen through the T cell receptor (TCR) following presentation of the antigen by MHC proteins. MHC and structurally related proteins including those encoded by class I and class II MHC genes on host cells will serve to present the peptide antigen(s) to T lymphocytes. The antigen components could also be supplied as purified MHC-peptide complexes alone or with co-stimulatory molecules that can directly signal T cells. Alternatively antibodies able to bind surface immunoglobulin and other molecules on B cells as well as antibodies able to bind the TCR and other molecules on T cells can be combined with the pharmaceutical composition of the invention. The pharmaceutical composition of the invention may be in the form of a liposome in which protein or polypeptide of the present invention is combined, in addition to other pharmaceutically acceptable carriers, with amphipathic agents such as lipids which exist in aggregated form as micelles, insoluble monolayers, liquid crystals, or lamellar layers in aqueous solution. Suitable lipids for liposomal formulation include, without limitation, monoglycerides, diglycerides, sulfatides, lysolecithin, phospholipids, saponin, bile acids, and the like. Preparation of such liposomal formulations is within the level of skill in the art, as disclosed, for example, in U.S. Pat. Nos. 4,235,871; 4,501,728; 4,837,028; and 4,737,323, all of which are incorporated herein by reference.

The amount of protein or polypeptide of the present invention in the pharmaceutical composition of the present invention will depend upon the nature and severity of the condition being treated, and on the nature of prior treatments which the patient has undergone. Ultimately, the attending physician will decide the amount of protein or polypeptide of the present invention with which to treat each individual patient. Initially, the attending physician will administer low doses of protein or polypeptide of the present invention and observe the patient's response. Larger doses of protein or polypeptide of the present invention may be administered until the optimal therapeutic effect is obtained for the patient, and at that point the dosage is not increased further. It is contemplated that the various pharmaceutical compositions used to practice the method of the present invention should contain about 0.01 μg to about 100 mg (preferably about 0.1 μg to about 10 mg, more preferably about 0.1 μg to about 1 mg) of protein or polypeptide of the present invention per kg body weight. For compositions of the present invention which are useful for bone, cartilage, tendon or ligament regeneration, the therapeutic method includes administering the composition topically, systematically, or locally as an implant or device. When administered, the therapeutic composition for use in this invention is, of course, in a pyrogen-free, physiologically acceptable form. Further, the composition may desirably be encapsulated or injected in a viscous form for delivery to the site of bone, cartilage or tissue damage. Topical administration may be suitable for wound healing and tissue repair. Therapeutically useful agents other than a protein or polypeptide of the invention which may also optionally be included in the composition as described above, may alternatively or additionally, be administered simultaneously or sequentially with the composition in the methods of the invention. Preferably for bone and/or cartilage formation, the composition would include a matrix capable of delivering the protein-containing composition to the site of bone and/or cartilage damage, providing a structure for the developing bone and cartilage and optimally capable of being resorbed into the body. Such matrices may be formed of materials presently in use for other implanted medical applications.

The choice of matrix material is based on biocompatibility, biodegradability, mechanical properties, cosmetic appearance and interface properties. The particular application of the compositions will define the appropriate formulation. Potential matrices for the compositions may be biodegradable and chemically defined calcium sulfate, tricalciumphosphate, hydroxyapatite, polylactic acid, polyglycolic acid and polyanhydrides. Other potential materials are biodegradable and biologically well-defined, such as bone or dermal collagen. Further matrices are comprised of pure proteins or extracellular matrix components. Other potential matrices are nonbiodegradable and chemically defined, such as sintered hydroxyapatite, bioglass, aluminates, or other ceramics. Matrices may be comprised of combinations of any of the above mentioned types of material, such as polylactic acid and hydroxyapatite or collagen and tricalciumphosphate. The bioceramics may be altered in composition, such as in calcium-aluminate-phosphate and processing to alter pore size, particle size, particle shape, and biodegradability. Presently preferred is a 50:50 (mole weight) copolymer of lactic acid and glycolic acid in the form of porous particles having diameters ranging from 150 to 800 microns. In some applications, it will be useful to utilize a sequestering agent, such as carboxymethyl cellulose or autologous blood clot, to prevent the protein or polypeptide compositions from disassociating from the matrix.

A preferred family of sequestering agents is cellulosic materials such as alkylcelluloses (including hydroxyalkylcelluloses), including methylcellulose, ethylcellulose, hydroxyethylcellulose, hydroxypropylcellulose, hydroxypropyl-methylcellulose, and carboxymethylcellulose, the most preferred being cationic salts of carboxymethylcellulose (CMC). Other preferred sequestering agents include hyaluronic acid, sodium alginate, poly(ethylene glycol), polyoxyethylene oxide, carboxyvinyl polymer and poly(vinyl alcohol). The amount of sequestering agent useful herein is 0.5-20 wt %, preferably 1-10 wt % based on total formulation weight, which represents the amount necessary to prevent desorbtion of the protein or polypeptide from the polymer matrix and to provide appropriate handling of the composition, yet not so much that the progenitor cells are prevented from infiltrating the matrix, thereby providing the protein or polypeptide the opportunity to assist the osteogenic activity of the progenitor cells. In further compositions, proteins or polypeptides of the invention may be combined with other agents beneficial to the treatment of the bone and/or cartilage defect, wound, or tissue in question. These agents include various growth factors such as epidermal growth factor (EGF), platelet derived growth factor (PDGF), transforming growth factors (TGF-.alphA. and TGF-.beta.), and insulin-like growth factor (IGF).

The therapeutic compositions are also presently valuable for veterinary applications. Particularly domestic animals and thoroughbred horses, in addition to humans, are desired patients for such treatment with proteins or polypeptides of the present invention. The dosage regimen of a protein-containing pharmaceutical composition to be used in tissue regeneration will be determined by the attending physician considering various factors which modify the action of the proteins or polypeptides, e.g., amount of tissue weight desired to be formed, the site of damage, the condition of the damaged tissue, the size of a wound, type of damaged tissue (e.g., bone), the patient's age, sex, and diet, the severity of any infection, time of administration and other clinical factors. The dosage may vary with the type of matrix used in the reconstitution and with inclusion of other proteins in the pharmaceutical composition. For example, the addition of other known growth factors, such as IGF I (insulin like growth factor I), to the final composition, may also effect the dosage. Progress can be monitored by periodic assessment of tissue/bone growth and/or repair, for example, X-rays, histomorphometric determinations and tetracycline labeling.

Polynucleotides of the present invention can also be used for gene therapy. Such polynucleotides can be introduced either in vivo or ex vivo into cells for expression in a mammalian subject. Polynucleotides of the invention may also be administered by other known methods for introduction of nucleic acid into a cell or organism (including, without limitation, in the form of viral vectors or naked DNA).

Cells may also be cultured ex vivo in the presence of proteins or polypeptides of the present invention in order to proliferate or to produce a desired effect on or activity in such cells. Treated cells can then be introduced in vivo for therapeutic purposes.

Pharmaceutical compositions suitable for use in the present invention include compositions wherein the active ingredients are contained in an effective amount to achieve its intended purpose. More specifically, a therapeutically effective amount means an amount effective to prevent development of or to alleviate the existing symptoms of the subject being treated. Determination of the effective amounts is well within the capability of those skilled in the art, especially in light of the detailed disclosure provided herein. For any compound used in the method of the invention, the therapeutically effective dose can be estimated initially from cell culture assays. For example, a dose can be formulated in animal models to achieve a circulating concentration range that includes the $IC_{50}$ as determined in cell culture (i.e., the concentration of the test compound which achieves a half-maximal inhibition of the C-proteinase activity). Such information can be used to more accurately determine useful doses in humans.

A therapeutically effective dose refers to that amount of the compound that results in amelioration of symptoms or a prolongation of survival in a patient. Toxicity and therapeutic efficacy of such compounds can be determined by standard pharmaceutical procedures in cell cultures or experimental animals, e.g., for determining the $LD_{50}$ (the dose lethal to 50% of the population) and the $ED_{50}$ (the dose therapeutically effective in 50% of the population). The dose ratio between toxic and therapeutic effects is the therapeutic index and it can be expressed as the ratio between $LD_{50}$ and $ED_{50}$. Compounds which exhibit high therapeutic indices are preferred. The data obtained from these cell culture assays and animal studies can be used in formulating a range of dosage for use in human. The dosage of such compounds lies preferably within a range of circulating concentrations that include the $ED_{50}$ with little or no toxicity. The dosage may vary within this range depending upon the dosage form employed and the route of administration utilized. The exact formulation, route of administration and dosage can be chosen by the individual physician in view of the patient's condition. See, e.g., Fingl et al., 1975, in "The Pharmacological Basis of Therapeutics", Ch. 1 p. 1. Dosage amount and interval may be adjusted individually to provide plasma levels of the active moiety which are sufficient to maintain the C-proteinase inhibiting effects, or minimal effective concentration (MEC). The MEC will vary for each compound but can be estimated from in vitro data; for example, the concentration necessary to achieve 50-90% inhibition of the C-proteinase using the assays described herein. Dosages necessary to achieve the MEC will depend on individual characteristics and route of administration. However, HPLC assays or bioassays can be used to determine plasma concentrations.

Dosage intervals can also be determined using MEC value. Compounds should be administered using a regimen which maintains plasma levels above the MEC for 10-90% of the time, preferably between 30-90% and most preferably between 50-90%. In cases of local administration or selective uptake, the effective local concentration of the drug may not be related to plasma concentration.

The amount of composition administered will, of course, be dependent on the subject being treated, on the subject's weight, the severity of the affliction, the manner of administration and the judgment of the prescribing physician.

The compositions may, if desired, be presented in a pack or dispenser device which may contain one or more unit dosage forms containing the active ingredient. The pack may, for example, comprise metal or plastic foil, such as a blister pack. The pack or dispenser device may be accompanied by instructions for administration. Compositions comprising a compound of the invention formulated in a compatible pharmaceutical carrier may also be prepared, placed in an appropriate container, and labelled for treatment of an indicated condition.

In one application of this embodiment, a nucleotide sequence of the present invention can be recorded on computer readable media. As used herein, 'computer readable media' refers to any medium which can be read and accessed directly by a computer. Such media include, but are not limited to: magnetic storage media, such as floppy discs, hard disc storage medium, and magnetic tape; optical storage media such as CD-ROM; electrical storage media such as RAM and ROM; and hybrids of these categories such as magnetic/optical storage media. A skilled artisan can readily appreciate how any of the presently known computer readable mediums can be used to create a manufacture comprising computer readable medium having recorded thereon a nucleotide sequence of the present invention. As used herein, 'recorded' refers to a process for storing information on computer readable medium. A skilled artisan can readily adopt any of the presently known methods for recording information on computer readable medium to generate manufactures comprising the nucleotide sequence information of the present invention.

A variety of data storage structures are available to a skilled artisan for creating a computer readable medium having recorded thereon a nucleotide sequence of the present invention. The choice of the data storage structure will generally be based on the means chosen to access the stored information. In addition, a variety of data processor programs and formats can be used to store the nucleotide sequence information of the present invention on computer readable medium. The sequence information can be represented in a word processing text file, formatted in commercially-available software such as WordPerfect and Microsoft Word, or represented in the form of an ASCII file, stored in a database application, such as DB2, Sybase, Oracle, or the like. A skilled artisan can readily adapt any number of dataprocessor structuring formats (e.g. text file or database) in order to obtain computer readable medium having recorded thereon the nucleotide sequence information of the present invention. Computer software is publicly available which allows a skilled artisan to access sequence information provided in a computer readable medium. The examples which follow demonstrate how software which implements the BLAST (Altschul et al., *J. Mol. Biol.* 215:403-410 (1990)) and BLAZE (Brutlag et al., *Comp. Chem.* 17:203-207 (1993)) search algorithms on a Sybase system is used to identify open reading frames (ORFS) within a nucleic acid sequence. Such ORFs may be protein or polypeptide encoding fragments and may be useful in producing commercially important protein or polypeptides such as enzymes used in fermentation reactions and in the production of commercially useful metabolites.

As used herein, 'a computer-based system' refers to the hardware means, software means, and data storage means used to analyze the nucleotide sequence information of the present invention. The minimum hardware means of the computer-based systems of the present invention comprises a central processing unit (CPU), input means, output means, and data storage means. A skilled artisan can readily appreciate that any one of the currently available computer-based systems are suitable for use in the present invention. As stated above, the computer-based systems of the present invention comprise a data storage means having stored therein a nucleotide sequence of the present invention and the necessary hardware means and software means for supporting and implementing a search means. As used herein, 'data storage means' refers to memory which can store nucleotide sequence information of the present invention, or a memory access means which can access manufactures having recorded thereon the nucleotide sequence information of the present invention.

As used herein, 'search means' refers to one or more programs which are implemented on the computer-based system to compare a target sequence or target structural motif with the sequence information stored within the data storage means. Search means are used to identify fragments or regions of a known sequence which match a particular target sequence or target motif. A variety of known algorithms are disclosed publicly and a variety of commercially available software for conducting search means are and can be used in the computer-based systems of the present invention. Examples of such software includes, but is not limited to, MacPattern (EMBL), BLASTN and BLASTA (NPOLYPEPTIDEIA). A skilled artisan can readily recognize that any one of the available algorithms or implementing software packages for conducting homology searches can be adapted for use in the present computer-based systems. As used herein, a 'target sequence' can be any nucleic acid or amino acid sequence of six or more nucleotides or two or more amino acids. A skilled artisan can readily recognize that the longer a target sequence is, the less likely a target sequence will be present as a random occurrence in the database. The most preferred sequence length of a target sequence is from about 10 to 100 amino acids or from about 30 to 300 nucleotide residues. However, it is well recognized that searches for commercially important fragments, such as sequence fragments involved in gene expression and protein or polypeptide processing, may be of shorter length.

As used herein, 'a target structural motif,' or 'target motif,' refers to any rationally selected sequence or combination of sequences in which the sequence(s) are chosen based on a three-dimensional configuration which is formed upon the folding of the target motif. There are a variety of target motifs known in the art. Protein or polypeptide target motifs include, but are not limited to, enzyme active sites and signal sequences. Nucleic acid target motifs include, but are not limited to, promoter sequences, hairpin structures and inducible expression elements (protein or polypeptide binding sequences).

The present invention further provides methods to identify the presence or expression of one of the targets recognized by a polypeptide or protein of the present invention, or homolog thereof, in a test sample.

In general, methods for detecting a target recognized by a polypeptide or protein of the invention can comprise contacting a sample with a polypeptide or protein of the invention that binds to and forms a complex with the target for a period sufficient to form a complex, and detecting the complex, so that if a complex is detected, a target of the invention is detected in the sample.

In detail, such methods comprise incubating a test sample with one or more of the antibodies of the present invention and assaying for binding of the antibodies to the target within the test sample.

Conditions for incubating an antibody, including a Fab fragment of the invention, with a test sample vary. Incubation conditions depend on the format employed in the assay, the detection methods employed, and the type and nature of the antibody used in the assay. One skilled in the art will recognize that any one of the commonly available amplification or immunological assay formats can readily be adapted to employ the antibodies of the present invention. Examples of such assays can be found in Chard, T., *An Introduction to Radioimmunoassay and Related Techniques*, Elsevier Science Publishers, Amsterdam, The Netherlands (1986); Bullock, G. R. et al., *Techniques in Immunocytochemistry*, Academic Press, Orlando, Fla. Vol. 1 (1982), Vol. 2 (1983), Vol. 3 (1985); Tijssen, P., *Practice and Theory of immunoassays: Laboratory Techniques in Biochemistry and Molecular Biology*, Elsevier Science Publishers, Amsterdam, The Netherlands (1985); and Kuwata et al., BioChem. Biophys. Res. Commun. 245:764-73 (1998), Hillenkamp et al., Anal. Chem. 63:1193-202 (1991), U.S. Pat. Nos. 5,111, 937 and 5,719,060. The test samples of the present invention include cells, protein or polypeptide or membrane extracts of cells, or biological fluids such as sputum, blood, serum, plasma, or urine. The test sample used in the above-described method will vary based on the assay format, nature of the detection method and the tissues, cells or extracts used as the sample to be assayed. Methods for preparing protein or polypeptide extracts or membrane extracts of cells are well known in the art and can be readily be adapted in order to obtain a sample which is compatible with the system utilized.

In another embodiment of the present invention, kits are provided which contain the necessary reagents to carry out the assays of the present invention. Specifically, the invention provides a compartment kit to receive, in close confinement, one or more containers which comprises: (a) a first container comprising one of the antibodies of the present invention; and (b) one or more other containers comprising one or more of the following: wash reagents, reagents capable of detecting presence of a bound antibody.

In detail, a compartment kit includes any kit in which reagents are contained in separate containers. Such containers include small glass containers, plastic containers or strips of plastic or paper. Such containers allows one to efficiently transfer reagents from one compartment to another compartment such that the samples and reagents are not cross-contaminated, and the agents or solutions of each container can be added in a quantitative fashion from one compartment to another. Such containers will include a container which will accept the test sample, a container which contains the antibodies used in the assay, containers which contain wash reagents (such as phosphate buffered saline, Tris-buffers, etc.), and containers which contain the reagents used to detect the bound antibody or probe. Types of detection reagents include labeled secondary antibodies, or in the alternative, if the primary antibody is labeled, the enzymatic, or antibody binding reagents which are capable of reacting with the labeled antibody. One skilled in the art will readily recognize that the disclosed probes and antibodies of the present invention can be readily incorporated into one of the established kit formats which are well known in the art.

Using the polypeptides or proteins of the invention, the present invention further provides methods of obtaining and identifying agents which bind to a target recognized by the polypeptide or protein. In detail, said method comprises the steps of:

(a) contacting a target with an isolated protein or polypeptide of the present invention; and
(b) determining whether the target binds to said protein or polypeptide.

In general, such methods for identifying compounds that bind to a polypeptide of the invention can comprise contacting a compound with a polypeptide of the invention for a time sufficient to form a polypeptide/compound complex, and detecting the complex, so that if a polypeptide/compound complex is detected, a compound that binds to a polynucleotide of the invention is identified.

Methods for identifying compounds that bind to a polypeptide of the invention can also comprise contacting a compound with a polypeptide of the invention in a cell for a time sufficient to form a polypeptide/compound complex, wherein the complex drives expression of a receptor gene sequence in the cell, and detecting the complex by detecting reporter gene sequence expression, so that if a polypeptide/compound complex is detected, a compound that binds a polypeptide of the invention is identified.

Compounds identified via such methods can include compounds which modulate the activity of a target recognized by a polypeptide or protein of the invention (that is, increase or decrease the target's activity, relative to activity observed in the absence of the compound). Alternatively, compounds identified via such methods can include compounds which modulate the expression of a polynucleotide of the invention (that is, increase or decrease expression relative to expression levels observed in the absence of the compound). Compounds, such as compounds identified via the methods of the invention, can be tested using standard assays well known to those of skill in the art for their ability to modulate activity/expression.

The agents screened in the above assay can be, but are not limited to, peptides, carbohydrates, vitamin derivatives, or other pharmaceutical agents. The agents can be selected and screened at random or rationally selected or designed using protein modeling techniques.

For random screening, agents such as peptides, carbohydrates, pharmaceutical agents and the like are selected at random and are assayed for their ability to bind to the target recognized by the polypeptide or protein of the present invention. Alternatively, agents may be rationally selected or designed. As used herein, an agent is said to be 'rationally selected or designed' when the agent is chosen based on the configuration of the particular protein or polypeptide. For example, one skilled in the art can readily adapt currently available procedures to generate peptides, pharmaceutical agents and the like capable of binding to a specific peptide sequence in order to generate rationally designed antipeptide peptides, for example see Hurby et al., Application of Synthetic Peptides: Antisense Peptides,' In *Synthetic Peptides, A User's Guide*, W. H. Freeman, NY (1992), pp. 289-307, and Kaspczak et al., *Biochemistry* 28:9230-8 (1989), or pharmaceutical agents, or the like.

In addition to the foregoing, one class of agents of the present invention, as broadly described, can be used to control gene expression through binding to one of the ORFs or EMFs of the present invention. As described above, such agents can be randomly screened or rationally designed/selected. Targeting the ORF or EMF allows a skilled artisan to design sequence specific or element specific agents, modulating the expression of either a single ORF or multiple ORFs which rely on the same EMF for expression control.

As choice of antibody format, we preferred the Fab format above the scFv format, because the Fab format allows rapid high through-put affinity-screening assays for crude antibody preparations. Many scFv's indeed form higher molecular weight species including dimers (Weidner, et al., (1992) *J. Biol. Chem.* 267, 10281-10288; Holliger, et al., (1993) *Proc. Natl. Acad. Sci. U.S.A* 90, 6444-6448) and trimers (Kortt et al., (1997) *Protein Eng.* 10, 423-433), which complicate both selection and characterisation. We chose the Fab display format in which a variable domain from a heavy or light chain gene is linked to a phage coat protein, and in some embodiments, also carries a tag for detection and purification. The other chain is expressed as separate fragment secreted into the periplasm, where it can pair with the gene that is in a protein fusion with the phage coat protein (Hoogenboom, et al., (1991) *Nucleic Acids Res.* 19, 4133-4137). In some embodiments, the phage coat protein a pIII coat protein. In other embodiments, the variable domain from a heavy chain gene is fused to the phage coat protein and the light chain gene is expressed as a separate fragment.

The choice for the Fab format was based on the notion that the monomeric appearance of the Fab permits the rapid screening of large numbers of clones for kinetics of binding (off-rate) with crude protein fractions. This reduces the time for post-selection analysis dramatically when compared to that needed for selected single-chain Fv (scFv) antibodies from phagemid libraries (Vaughan, et al., (1996) *Nat. Biotechnol.* 14, 309-314; Sheets, et al., (1998) *Proc. Natl. Acad.*

Sci. U.S.A 95, 6157-6162), or Fab fragments from other phage libraries (Griffiths, et al., (1993) *EMBO J.* 12, 725-734).

The Fab library of the invention produced on average 14 different Fab's against 6 antigens that were tested. These include tetanus toxoid, the hapten phenyl-oxazolone, the breast cancer associated MUC1 antigen and three highly related glycoprotein hormones: human Chorionic Gonadotropin ('hCG'), human Luteinizing Hormone ('hLH') and human Follicle Stimulating Hormone ('hFSH'). For the glycoprotein hormones, the Fab library of the invention produced a panel of either hormone-specific or cross-reactive antibodies. Thus, without using sophisticated selection protocols, hormone specific as well as cross-reactive Fab's were retrieved against these highly homologous glycohormones, demonstrating that the library is a rich source of antibody specificities. The affinities of the anti-glycohormone antibodies varied between 2.7 and 38 nM. Finally, the Fab-format indeed permitted the rapid screening and a reliable ranking of individual clones based on off-rate using crude fractions.

Furthermore, the specificities of the antibodies obtained by selections on the gonadotropins are unique: due to the high degree of homology between hLH and hCG it has been very difficult to isolate hCG specific monoclonal antibodies with the hybridoma technology, whereas there are very few hLH specific antibodies (Moyle, et al., (1990) *J. Biol. Chem.* 265, 8511-8518; Cole, (1997) *Clin. Chem.* 43, 2233-2243). Using a straight forward selection procedure, taking no precaution to avoid the selection of cross-reactive Fab's, we have readily isolated fragments with all possible specificities: Fab's specific for any of the three hormones hCG, hLH and hFSH, and cross-reactive Fab's recognizing the common α-chain or epitopes on the α-chain shared by hCG and hLH. These selections demonstrated that antibodies directed against different epitopes within single antigen molecules can be retrieved from the library. The Fab library of the invention permits the monitoring of selections with polyclonal phage preparations and large scale screening of antibody off-rates with unpurified Fab fragments.

Overall, antibodies with off-rates in the order of $10^{-2}$ to $10^{-4}$ $s^{-1}$ and affinities up to 2.7 nM, were recovered. The kinetics of these phage antibodies are of the same order of magnitude as antibodies associated with a secondary immune response.

An indication that antibodies from the Fab library behave similarly or better than antibodies from a scFv library with regards to affinity comes from a comparison of selections of two different libraries on the same two antigens under identical conditions. Antibodies to MUC1 selected from a large naVve scFv library (Henderikx et al., (1998) *Cancer Res.* 58, 4324-4332) have faster off-rates then the equivalent Fab's isolated from the library described in this study. Further, they show a very distinct V-gene usage and have a different fine specificity. Similarly, when comparing the off-rates of phage antibodies against the pancarcinoma marker Epithelial Glycoprotein-2, one of the Fab's selected from the present library appears to have a 10-fold slower off-rate than the best scFv (Vaughan et al., (1996) *Nat. Biotechnol.* 14, 309-314).

The affinities of the selected antibody fragments is, however, very much dependent on the antigen used for selection. Sheets and colleagues reported an affinity varying between 26 and 71 nM for the selected scFv fragments specific for the anti-*Clostridia botulinum* neurotoxin type A fragments, whereas for antibodies to the extracellular domain of human ErbB-2, $K_d$'s between 0.22 and 4.03 nM were found (Sheets et al., (1998) *Proc. Natl. Acad. Sci. U.S.A* 95, 6157-6162). The affinities of the gonadotropin specific Fab's selected from our library varied between 2.7 and 38 nM, which is comparable to the protein binding scFv's from the naVve library made by Vaughan et al. and Sheets et al., and approaches the values of the best antibodies in their kind.

The size of the Fab library of the invention is not only important for affinity, but it also determines the success rate of selection of antibodies against a large set of different antigens. In this respect the Fab library of the invention performs very well: over 24 antibodies to the hapten phOx, and on average 13 antibodies against the other antigens were selected.

In the limited set of 14 Fab clones that were sequenced, we identify antibodies with variable region genes from all large V-gene families, including $V_{H1/3/4}$, $V_{61/3}$, and $V_{81/2}$, but also less frequently used segments of family $V_{H6}$, $V_{62/7}$ and $V_{87}$ were retrieved. Most likely the use of an extended set of variable region gene primers, designed on the most recent sequence information of the germline V-regions, and/or the separate PCRs, combined with partially separate cloning, ensured access to a highly diverse sample of the human V-gene repertoire.

According to the present invention, a library is prepared from polynucleotides which are capable of encoding the desired specific binding pair member. A variety of techniques exist for preparing the library, which may be prepared, for example, from either genomic DNA or cDNA. See, e.g., Sambrook et al., Molecular Cloning, A Laboratory Manual, 2nd ed., Cold Spring Harbor Laboratory Press, Cold Spring Harbor, N.Y., 1989, which is incorporated herein by reference. Cells may serve as the source of the polynucleotides which encode the specific binding pair members of interest. Enrichment procedures and means for amplifying the regions containing the gene(s), may be employed. For instance, when the desired specific binding pair member is an antibody, RNA and or genomic DNA may be prepared, for example, from spleen cells obtained from an unimmunized animal, from an animal immunized with target(s) of interest, from hybridoma cells, or from lymphoblastoid cells. The library of antibodies obtained from the unimmunized animals contain an unbiased representation of the entire antibody repertoire, while the library of antibodies obtained from the immunized animals contain a biased population of antibodies directed against epitopes of the target(s). Spleen cells, or immune cells from other tissues or the circulatory system may be obtained from a variety of animal species, such as human, mouse, rat, equine, bovine, avian, etc.

Amplification of messenger RNA (mRNA) isolated from cells of interest, such as spleen or hybridoma cells, may be performed according to protocols outlined in, e.g., U.S. Pat. No. 4,683,202, Orlandi, et al. Proc. Natl. Acad. Sci. USA 86:3833-3837 (1989), Sastry et al., Proc. Natl. Acad. Sci. USA 86:5728-5732 (1989), and Huse et al. Science 246: 1275-1281 (1989), Abelson, J. and Simon, M. (eds), Methods in Enzymology, combinatorial chemistry, Vol. 267, San Diego: Academic Press (1996), Kay, B. K., Winter, J., McCafferty, J. (eds), Phage Display of peptides and Proteins, a Laboratory Manual, San Diego: Academic Press (1996), each incorporated herein by reference. Oligonucleotide primers useful in amplification protocols may be unique or degenerate or incorporate inosine at degenerate positions. Thus, for multi-chain immunoglobulins, primers would be generally used for amplification of sequences encoding the variable regions of both the heavy and light chains. Restriction endonuclease recognition sequences may be incorporated into the primers to allow for the cloning of the amplified fragment into a vector in a predetermined reading frame for expression.

Expression libraries containing the amplified cDNA are typically prepared in a vector such as a bacteriophage or phagemid. The characteristics of the suitable bacteriophage or phagemid depends on the specific embodiment employed, and will generally be those which conveniently allow insertion of the recombinant polynucleotides into host cells by in vitro packaging or transformation.

Host cells are then infected with the phage or phagemid and helper phage, and cultivated under conditions allowing for the expression and assembly of phage particles. In one embodiment, the appropriate host cells for the bacteriophage or phagemids of the invention are various strains of E. coli, specific examples depending on which of the several suitable vectors is chosen. Of course, phage or phagemid having bacterial hosts other than E. coli may also be used.

To enrich for and isolate phage particles or phage which contain cloned library sequences that encode a desired specific binding pair member, and thus to ultimately isolate the nucleic acid sequences themselves, phage particles or phage harvested from the host cells are affinity purified. A target or binding partner for the desired specific binding pair member is used in the affinity purification. For example, when the desired specific binding pair member is an antibody which specifically binds a particular target, the target is used to retrieve phage particles or phage having the desired antibody on its outer surface. The target is typically adsorbed to an insoluble substrate, such as a particle or bead or plate. The phage particles or phage so obtained may then be amplified by infecting into host cells (with helper phage for the phage particles containing the phagemids). Additional rounds of affinity enrichment and amplification may be employed until the desired level of enrichment is reached or the desired phage particles or phage are no longer enriched relative to the background phage particles or phage.

The enriched antibody-phage particles or phage are also screened with additional detection techniques such as expression plaque (or colony) lift (see, e.g., Young and Davis, Science, 222:778-782 (1983), incorporated herein by reference) whereby the same or another binding partner is used as a probe. Screening may employ additional assays (for a catalytic activity, for example) which are used to detect, in situ, plaques expressing specific binding pair members having the desired characteristics. The phage particles or phage obtained from the screening protocol are infected into cells, propagated, and the phage particle or phage DNA isolated and sequenced, and/or recloned into a vector intended for gene expression in prokaryotes or eukaryotes to obtain larger amounts of the selected specific binding pair member.

In another embodiment, the specific binding pair member encoded in the library (or multiple chains comprising said specific binding pair member) is transported to an extra-cytoplasmic compartment of the host cell, usually the periplasmic space, to facilitate processing and/or proper assembly. When extra-cytoplasmic transport of the desired specific binding pair member is employed, the sequences encoding the specific binding pair member are cloned adjacent to appropriate transcriptional and translational signals and signal peptide leaders that will direct the mature chains to the periplasm. As above, at least one of the chains is cloned as a fusion protein with a phage coat protein so that the phage coat protein does not substantially interfere with the ability of the specific binding pair member of interest to bind a target which is used in the affinity enrichment protocol.

A preferred example of this embodiment is the placement of a specific binding pair member in the N-terminus region of the minor coat protein pIII of bacteriophage fd. Before incorporation into the phage, pIII resides in the inner membrane of the host cell with its N-terminus protruding into the periplasm. In this configuration the polypeptide of a specific binding pair member in the N-terminus of pIII is available for binding to other polypeptide chains that make up the specific binding pair member of interest. This complex is then incorporated into the mature phage particle or phage as it exits the cell and the C-terminus embeds in the coat of the phage particle or phage.

In this embodiment the synthesis and amplification of polynucleotides is as described above, and then is cloned into or near a vector sequence encoding a coat protein, where the vector is, or is derived from, a filamentous phage, such as f1, fd, Pf1, M13, etc. In a preferred embodiment the filamentous phage is fd-tet. The phage vector is chosen to contain a cloning site located in the 5' region of a gene encoding a phage coat protein, such as, for example, the pIII coat protein. An appropriate vector (e.g., fd-tet B1 which is described below) allows oriented cloning of foreign sequences so that they are expressed at or near the N-terminus of the mature coat protein.

A library is constructed by cloning the polynucleotides (e.g., the $V_H$ region) from the donor cells into a coat protein gene (e.g., gene III, "gIII") cloning site. The cloned sequences of, for example, the $V_H$ domains are ultimately expressed as polypeptides or proteins fused to the N-terminus of the mature coat protein on the outer, accessible surface of the assembled phage particles or phage.

When the desired protein is a multi-chain protein, such as an antibody or binding fragment thereof, the polynucleotide encoding the chain(s) not cloned into a phage coat protein may be cloned directly into an appropriate site (as described below) of the vector containing the first chain-coat protein library; or, preferably, the subsequent chain(s) may be cloned as a separate library in a different plasmid vector, amplified, and subsequently the fragments installed in the first chain-coat protein library vector. For example, when the first chain is an antibody heavy chain or binding fragment thereof, the ultimate destination of light chain $V_L$ cDNA sequence is in a vector that already contains a $V_H$ sequence in a coat protein gene, thus randomly recombining $V_H$ and $V_L$ sequences in a single vector.

The second or subsequent chain of the desired multi-chain protein, such as $V_L$, is cloned so that it is expressed with a signal peptide leader sequence that will direct its secretion into the periplasm of the host cell. For example, several leader sequences have been shown to direct the secretion of antibody sequences in E. coli, such as OmpA (Hsiung, et al., Biotechnology 4:991-995 (1986)), pelB (Better, et al., Science 240:1041-1043 (1988)), phoA (Skerra and Pluckthun, Science 240:1038-1043 (1988)), beta-lactamase (Zemel-Dreasen and Zamir, Gene 27:315-322 (1984)), and those described in Abelson, J. and Simon, M. (eds), Methods in Enzymology, combinatorial chemistry, Vol. 267, San Diego: Academic Press (1996), and Kay, B. K., Winter, J., McCafferty, J. (eds), Phage Display of peptides and Proteins, a Laboratory Manual, San Diego: Academic Press (1996), each incorporated herein by reference.

Generally, the successful cloning strategy utilizing a phage coat protein, such as pIII of filamentous phage fd, will provide: (1) expression of a protein chain (or a first polypeptide chain when the desired protein is multichained, e.g., the $V_H$ chain) fused to the N-terminus of a full sized (or nearly full sized) coat protein (e.g., pIII) and transport to the inner membrane of the host where the hydrophobic domain in the C-terminal region of the coat protein anchors the fusion protein in the membrane, with the N-terminus containing the chain protruding into the periplasmic space and available for interaction with a second or subsequent chain (e.g., $V_L$ to form an Fab fragment) which is thus attached to the coat protein; and (2) adequate expression of a second or subsequent polypeptide chain if present (e.g., $V_L$) and transport of this chain to the soluble compartment of the periplasm.

In one embodiment for affinity enrichment of desired clones, about $10^3$ to $10^4$ library equivalents (a library equivalent is one of each recombinant—$10^4$ equivalents of a library of $10^9$ members is $10^9 \times 10^4 = 10^{13}$ phage particles or phage) are incubated with target to which the desired specific binding pair member (e.g., antibody) is sought. The target is in one of several forms appropriate for affinity enrichment schemes. In one example the target is immobilized on a surface or particle, optionally anchored by a tether of enough length (3 to 12 carbons, for example) to hold the target far enough away from the surface to permit free interaction with the antibody combining site. The library of phage particle or phage bearing antibodies is then panned on the immobilized target generally according to procedures well-known in the art, for example, those described in Abelson, J. and Simon, M. (eds), Methods in Enzymology, combinatorial chemistry, Vol. 267, San Diego: Academic Press (1996), Kay, B. K., Winter, J., McCafferty, J. (eds), Phage Display of peptides and Proteins, a Laboratory Manual, San Diego: Academic Press (1996), each incorporated herein by reference.

A second example of target presentation is target attached to a recognizable ligand (again optionally with a tether of some length). A specific example of such a ligand is biotin. The target, so modified, is incubated with the library of phage particles or phage and binding occurs with both reactants in solution. The resulting complexes are then bound to streptavidin (or avidin) through the biotin moiety. The streptavidin may be immobilized on a surface such as a plastic plate or on particles, in which case the complexes are physically retained; or the streptavidin may be labelled, with a fluorophore, for example, to tag the active phage/antibody for detection and/or isolation by sorting procedures, e.g., on a fluorescence-activated cell sorter.

In one embodiment, the phage particles or phage bearing antibodies without the desired specificity are removed by various means, for example, by washing. The degree and stringency of washing required will be determined for each specific binding pair member of interest. A certain degree of control can be exerted over the binding characteristics of the antibodies recovered by adjusting the conditions of the binding incubation and the subsequent washing. The temperature, pH, ionic strength, divalent cations concentration, and the volume and duration of the washing will select for antibodies within particular ranges of affinity for the hapten. Selection based on slow dissociation rate, which is usually predictive of high affinity, is the most practical route. This may be done either by continued incubation in the presence of a saturating amount of free hapten, or by increasing the volume, number, and length of the washes. In each case, the rebinding of dissociated antibody-phage is prevented, and with increasing time, antibody-phage of higher and higher affinity are recovered.

Antibodies with certain catalytic activities may be enriched in groups of antibodies with high affinity for reactants (substrates and intermediates) but low affinity for products. A double screen to enrich for antibodies with these characteristics may be useful in finding antibodies to catalyze certain reactions. Further, catalytic antibodies capable of certain cleavage reactions may also be selected. One category of such reactions is the cleavage of a specific end group from a molecule. For example, a catalytic antibody to cleave a specific amino acid from an end of a peptide may be selected by immobilizing the peptide and panning the antibody library under conditions expected to promote binding but not cleavage (e.g., low temperature, particular ionic strength, pH, cation concentration, etc., depending on the nature of the end group and the cleavage reaction) and followed by a wash. This allows antibodies that recognize the end group to bind and become immobilized, and from this group will come those capable of cleavage. To find those capable of cleavage, the conditions are shifted to those favorable for cleavage. This step will release those antibody-phage capable of cleaving themselves free of the immobilized peptide.

An alternative way to accomplish this is to pan for antibodies that bind to the specific end group by attaching that end group to a bond different from that to be cleaved (a non-peptide bond, for example). By subsequent panning (of the positive phage from the first screen) on the end group attached via the proper bond under cleavage conditions, the non-binding fraction will be enriched for those with the desired catalytic activity.

To elute the active antibody-phage particle or phage from the immobilized target, after washing at the appropriate stringency, the bound (active) phage particle or phage can be recovered by eluting with pH shift. For example, pH2 or pH11 may be used, which is then neutralized and the eluted phage are amplified by infecting or transforming the host cells. The cells are then grown as tetracycline resistant colonies. The colonies are scraped up and the extruded phage are purified by standard procedures as before. These phage are then used in another round of affinity enrichment (panning), and this cycle is repeated until the desired level of enrichment is reached or until the target phage are no longer enriched relative to the background phage particles or phage. To isolate individual clones, phage particles or phage from the final round of panning and elution are infected into cells or their DNA is transformed into cells and grown on agar (usually L-agar) and antibiotics (usually tet) to form well separated individual colonies, each of which is a clone carrying vectors with both $V_H$ and $V_L$ sequences. The single stranded DNA from phage particles or phage extruded from each colony may be isolated and DNA coding for the $V_H$ and $V_L$ fragments sequenced. The replicative form of the phage DNA (double stranded) may be isolated by standard means and the DNA in the cloning sites ($V_H$ and $V_L$ sequences) recloned into a vector designed for gene product expression in prokaryotes or eukaryotes to obtain larger amounts of the particular antibodies selected in the screening process.

Phage identified as having an antibody recognized by the target ligand are propagated as appropriate for the particular phage vector used. For fd-tet this is done in a liquid culture of rich medium (L-broth, for example) with antibiotic (Tet) selection. The phage are harvested and DNA prepared and sequenced by standard methods to determine the DNA and amino acid sequence of the particular antibody.

The DNA may be recloned in a suitable eukaryotic or prokaryotic expression vector and transfected into an appropriate host for production of large amounts of protein. Antibody is purified from the expression system using standard procedures. The binding affinity of the antibody is confirmed by well known immunoassays with the target antigen or catalytic activity as described in Harlow and Lane, Antibodies, A Laboratory Manual, Cold Spring Harbor, N.Y. (1988), Abelson, J. and Simon, M. (eds), Methods in Enzymology, combinatorial chemistry, Vol. 267, San Diego: Academic Press (1996), Kay, B. K., Winter, J., McCafferty, J. (eds), Phage Display of peptides and Proteins, a Laboratory Manual, San Diego: Academic Press (1996), each incorporated herein by reference.

In another embodiment, phage particles or phage displaying the desired specific binding pair member are affinity purified as follows: approximately $10^3$-$10^4$ library equivalents of phage particles or phage are reacted overnight with 1 micropgram purified antibody at 4° C. The mixture is panned by a procedure as follows. A polystyrene petri plate is coated with 1 ml of streptavidin solution (1 mg/ml in 0.1M NaHCO$_3$, pH 8.6, 0.02% NaN$_3$) and is incubated overnight at 4° C. The following day the streptavidin solution is removed. The plate is filled with 10 ml blocking solution (30 mg/ml BSA, 3 micrograms/ml streptavidin in 0.1M NaHCO$_3$, pH 9.2, 0.02% NaN$_3$) and incubated for 2 hours at room temperature. Two micrograms of biotinylated goat anti-mouse IgG (BRL) are added to the antibody-reacted library and incubated for 2 hours at 4° C. Immediately before panning, blocking solution is removed from streptavidin coated plate, and the plate is washed 3 times with TBS/0.05% Tween 20. The antibody-reacted library is then added to the plate and incubated for 30 minutes at room temperature. Streptavidin coated agarose beads (BRL) may also be used for this affinity purification. The library solution is removed and the plate is washed ten times with TBS/0.05% Tween 20 over a period of 60 minutes. Bound phage are removed by adding elution buffer (1 mg/ml BSA, 0.1N HCl, pH adjusted to 2.2 with glycine) to the petri plate and incubating for 10 minutes to dissociate the immune complexes. The eluate is removed, neutralized with 2M Tris (pH unadjusted) and used to infect log phase F'-containing bacterial cells. These cells are then plated on LB agar plates containing tetracycline (20 .mu.g/ml), and grown overnight at 37° C. Phage-particles or phage are isolated from these plates as described and the affinity purification process was repeated for two to three rounds. After the final round of purification, a portion of the eluate is used to infect cells and plated at low density on LB tetracycline plates. Individual colonies are transferred to culture tubes containing 2 ml LB tetracycline and grown to saturation. Phage or phagemid DNA is isolated using a method designed for the Beckman Biomek Workstation (Mardis and Roe., Biotechniques, 7:840-850 (1989)) which employs 96-well microtiter plates. Single stranded DNA is sequenced by the dideoxy method using Sequenase (U.S. Biochemicals) and an oligonucleotide sequencing primer (5'-CGATCTAAAGTTTT-GTCGTCT-3' SEQ ID NO: 2) which is complementary to the sequence located 40 nucleotides 3' of the second BstXI site in fdTetB1.

We considered a number of variables to address in the construction of a novel, very large antibody phage library: (i) the primer design was optimised for amplification of variable gene pools to maintain maximum diversity; (ii) a highly efficient two-step cloning method was developed to obtain a very large naive library; (iii) an antibody format and compatible cloning vector were chosen, which should permit the rapid down-stream analysis of selected clones.

In order to achieve access to as many different human heavy and light chain V-region gene segments as possible, a new set of oligonucleotide primers was developed (Table I), the design of which was based on the most recent sequence information provided by the V-base.

The primers were designed to be the or several consensus sequences which would have at least a 70% homology to the respective 5' or 3' end based coding region in the human germ line gene segments of the specific V gene family they would have to amplify. The primers would amplify at least one V-gene segment using the PCR conditions described below, and in one embodiment are appended with appropriate positioned restriction sites for cloning into the vector for Fab expression.

The primers should allow efficient amplification of all commonly used V-gene segments. Further, to obtain the large sized Fab libraries of the invention (over 10" in diversity), we used a two-step cloning procedure: heavy and light chain variable genes were first separately cloned as digested PCR products, and were then combined by restriction fragment cloning to form a large library of Fab fragments. This cloning procedure should be a more efficient route for library construction than the relatively inefficient direct cloning of digested PCR-products, while avoiding the DNA instability often associated with in vivo recombination systems (Griffiths, et al., (1994) EMBO J. 13, 3245-3260).

Figure 1B:
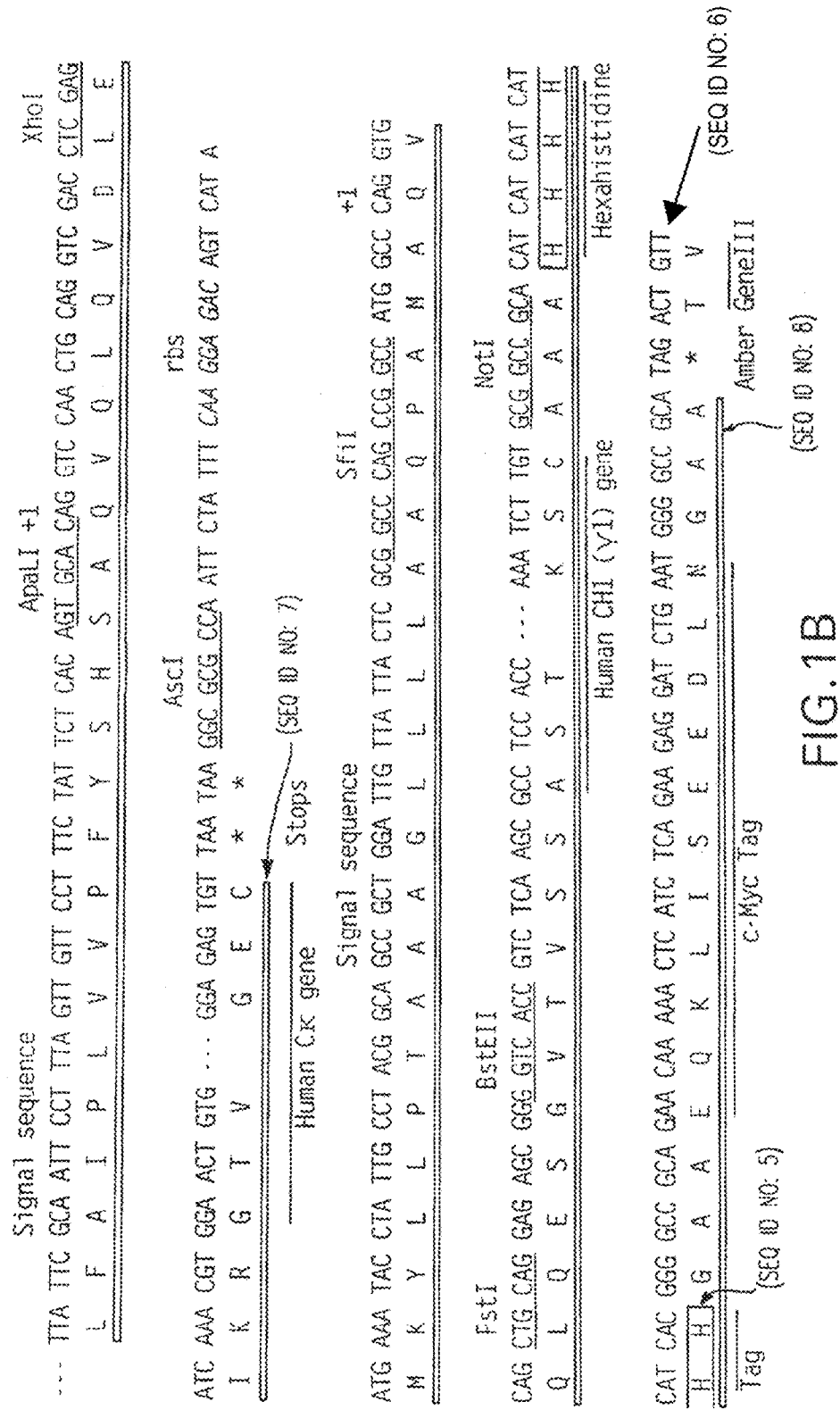
FIG. 1B. shows polylinker region of the phagemid vector pCES1 (SEQ ID NO:6)

A new phagemid vector, pCES1 (FIG. 1), was constructed, that allows the stepwise cloning of antibody fragments in Fab format. In this vector system, the variable heavy chain region genes are cloned as $V_H$-gene fragments; the vector supplies all Fab's with a human gamma-1 $C_{H1}$ domain. The $V_H C_{H1}$ formed by insertion of the $V_H$-gene fragments to the vector is fused (in the vector) to two tags for purification and detection (a histidine tail for Immobilised Metal Affinity Chromatography (Hochuli, et al., (1988) *BioTechnology* 6, 1321-1325) and a c-myc-derived tag (Munro, et al., H. R. (1986) *Cell* 46, 291-300)), followed by an amber stop codon (Hoogenboom, et al., (1991) *Nucleic Acids Res.* 19, 4133-4137) and the minor coat protein III of filamentous phage $f_d$. The antibody light chain is cloned as full $V_L C_L$ fragment, for directed secretion and assembly with the $V_H C_{H1}$ on the phage particle.

In one embodiment, the vector comprises an expression cassette with a bicistronic or double cistronic expression cassette to allow linked (for the bicistronic) or independent (for the double cistronic) expression of the antibody light and heavy chain or their fusions, such expression cassette consisting of the following elements: (1) a promoter suited for non-inducible and inducible expression (e.g lacZ); (2) a ribosome binding site and signal sequence preceeding the light and heavy chain cloning regions; (3) possible, but not necessarily, a region following the heavy or light chain cloning region that encodes a tag sequence such as a stretch of 5-6 histidines or a sequence recognised by an antibody and an amber codon; (4) a phage coat protein encoded as a fusion to the 3' end of either the heavy or light chain.

This new phage library will be a valuable source of antibodies to essentially any target. The antibodies may be used as research reagents or as starting point for the development of therapeutic antibodies or agricultural products. As the list of sequenced genomes and disease-related gene products is expanding rapidly, there will be a growing need for an in vitro and eventually automated method for antibody isolation. As antibodies have been and will be ideal probes for investigating the nature, localization and purification of novel gene products, this library is envisaged to play an important role in target validation and target discovery in the area of functional genomics.

Protein variants expressed on the surface of bacteriophage have been selected on the basis of their affinity for ligand (antigen) using chromatography, panning or adsorption to cells. Elution from affinity matrices has been achieved by specific elution using the ligand (antigen or a related compound) or non-specific elution using, for example, 100 mM triethylamine. Washing procedures remove non-specifically bound phage. The phage binds to and is eluted from the matrix according to the affinity or the nature of the binding interaction. Specifically eluted phage are then used to infect male *E. coli* cells expressing the F pilus, allowing recovery of phage containing DNA encoding proteins with the desired binding characteristics.

Selection can be made not only on the basis of specificity, but also on the basis of affinity. Separation is readily attainable by affinity chromatography between phage expressing an antibody with a dissociation constant of $10^{-8}$ M and one with a dissociation constant of $10^{-5}$ M. Clackson, T. et al. (1991). Nature 352: 624-628. The isolation of the latter antibody from an immune repertoire demonstrates that antibodies with affinities characteristic of the primary immune response can be isolated using phage technology.

Antibodies directed against cell surface antigens can also be isolated by selective adsorption of phage on the surface of cells. Similarly, it may be possible to incorporate negative selection with cells to remove undesired cross-reactivities with cell surface markers. As these are rather difficult and as yet poorly understood methods, methods based on the selection on purified antigen should be used whenever possible.

Any selection for binders within a population will automatically tend to select for high affinity variants at the expense of the lower, enriching the high affinity population. This has been used to good effect recently in the isolation of high affinity human antibodies from a naive repertoire. Marks, J. D. et al. (1991) J. Mol. Biol. 222, 581-597. For optimal selection, the antigen concentration should be less than the affinity constant. This should be borne in mind when isolating an antibody with pre-defined characteristics. Further details on various selection methods is given in the reviews in this manual.

With such large panels of antibodies isolated, it is useful to have methods available to readily determine the kinetic parameters of each individual antibody-antigen interaction. We have shown that it is feasible to rapidly and accurately determine the off-rate of non-purified antibodies in periplasmic fractions prepared from small scale cultures using surface plasmon resonance. Using this method, a series of tetanus toxoid specific Fab's showed a monophasic dissociation, which is expected for a truly monomeric Fab-fragment binding to a low density antigen surface. Using this off-rate screening assay, we determined the off-rates for the best tetanus toxoid and MUC1 specific Fab's to be in the order of $10^{-2}$ to $10^{-4}$ $s^{-1}$.

We tested the integrity of selected Fab's obtained from periplasmic fractions using western blots. When incubated in non-reducing sample buffer, two products were detected with the 9E10 antibody, which recognises the myc-tag at the end of the CH1 domain, the major product is the intact Fab-molecule, in which an intermolecular disulfide bridge covalently links heavy and light chain fragments; the low molecular product is most likely derived from non disulfide bridge linked heavy chains. Analysis with anti-light chain sera reveals a similar pattern and shows that the clones use a nearly equal percentage of kappa and lambda chains (found in six and seven clones respectively of a total of 13 tested). Upon reduction of purified, functional antigen-binding Fabs, equal amounts of heavy and light chain are seen, while under non-reducing conditions, the main product is represented by the disulphide linked Fab-molecule, with an equal amount of the non-covalently linked $V_H C_{H1}$ and $V_L C_L$ products visible. Production yields of selected hormone specific Fab's varied between 160 µg and 1.43 mg Fab per liter culture, which was in the same range as was found for the unselected Fabs.

A panel of 14 antigen-specific Fab's was fully sequenced (3 anti-MUC1 antibodies; 11 anti-gonadotropin antibodies). The heavy chain genes are derived from the four largest $V_H$ families ($V_{H1}$, $V_{H3}$, $V_{H4}$ and $V_{H6}$); the $V_L$ genes belong to one of four $V_\kappa$-families or one of three $V_\lambda$-families. Chain promiscuity is seen for the α-chain specific clone SC#4G, the α/β-LH specific clones LH#2H and LH#3G, and β-FSH specific clone FS#8B, which all used a highly homologous $V_{\kappa 2}$ light chain gene segment combined with different heavy chain fragments. The 3 anti-MUC1 antibodies use heavy and light chain genes derived from 2 different VH and V6 families; clone MUC#9 uses a VH with a cross-over of 2 segments.

The present invention is further illustrated in the following examples. Upon consideration of the present disclosure, one of skill in the art will appreciate that many other embodiments and variations may be made in the scope of the present invention. Accordingly, it is intended that the broader aspects of the present invention not be limited to the disclosure of the following examples.

As source of lymphoid tissues we used peripheral blood lymphocytes from 4 healthy donors and part of a tumor-free spleen removed from a patient with gastric carcinoma. B lymphocytes were isolated from 2-L of blood on a Ficoll-Pacque gradient. For RNA isolation, the cell pellet was immediately dissolved in 50 ml 8 M guanidinium thiocyanate/0.1 M 2-mercaptoethanol (Chirgwin, et al., (1979) *Biochemistry* 18, 5294-5299). Chromosomal DNA was sheared to completion by passing through a narrow syringe (1.2/0.5 mm gauge), and insoluble debris was removed by low speed centrifugation (15 min 2,934×g at room temperature). RNA was pelleted by centrifugation through a CsCl-block gradient (12 ml supernatant on a layer of 3.5 ml 5.7 M CsCl/0.1 M EDTA; in total 4 tubes) during 20 h at 125,000×g at 20° C. in a SW41-rotor (Beckman). The yield of total RNA was approx. 600 µg. RNA was stored at $-20^E C$ in ethanol.

From the spleen, 2 g of tissue was used for homogenisation with a polytron in 20 ml 8 M guanidinium thiocyanate/0.1 M 2-mercaptoethanol. The total volume was increased to 80 ml with guanidinium thiocyanate buffer, and after passage through a narrow syringe for shearing and removal of debris, RNA was pelleted as described before, except for 15 h at 85,000×g at 20EC in a SW28.1 rotor (12 ml supernatant on 3.5 ml 5.7 M CsCl/0.1 M EDTA in 5 SW28.1 tubes). From 2 g of tissue, 3 mg of total RNA was extracted.

Random primed cDNA was prepared with 250 µg PBL RNA, while in a separate reaction 300 µg spleen RNA was used as template. RNA was heat denatured for 5 min at 65° C. in the presence of 20 µg random primer (Promega), subsequently buffer and DTT were added according to the suppliers instructions (Gibco-BRL), as well as 250 µM dNTP (Pharmacia), 800 U RNAsin (40 U/µl; Promega) and 2,000 U MMLV-RT (200 U/µl; Gibco-BRL) in a total volume of 500 µl. After 2 h at 42° C., the incubation was stopped by a phenol/chloroform extraction; cDNA was precipitated and dissolved in 85 µl water.

Oligonucleotides used for PCR amplification of human heavy and light chain V-regions are described in FIG. 2. IgM-derived heavy chain variable regions were obtained by a primary PCR with an IgM constant region primer. All primary PCRs were carried out with separate BACK primers and combined FOR primers, to maintain maximal diversity. The PCR-products were reamplified with a combination of JHFOR-primers, annealing to the 3' end of $V_H$, and Sfi-tagged VHBACK-primers, annealing to the 5' end, and subsequently cloned as $V_H$-fragments. The light chain V-genes of the kappa and lambda families were obtained by PCR with a set of CKFOR- or CλFOR-primer annealing to the 3' end of the constant domain and BACK-primers, priming at the 5' end of the V-regions. The DNA-segments were reamplified with primers tagged with restriction sites and cloned as $V_\kappa C_\kappa$- and $V_\lambda C_\lambda$-fragments.

PCR was performed in a volume of 50 μl using AmpliTaq polymerase (Cetus) and 500 μM of each primer for 28 cycles (1 min at $94^EC$, 1 min at $55^EC$ and 2 min at $72^EC$), 9 separate IgM derived VH-amplifications were generated with 2 μl random primed cDNA (equivalent to 6 μg PBL RNA or to 7 μg spleen RNA) as template for each reaction. For the light chain families, 6 different $V_\kappa C_\kappa$-products and 11 $V_\lambda C_\lambda$-products ($C_{\lambda 2}$- and $C_{\lambda 7}$-primers combined in each reaction) were obtained. All products were purified from agarose gel with the QIAex-II extraction kit (Qiagen). As input for reamplification to introduce restriction sites, 100-200 ng purified DNA-fragment was used as template in a 100 μl reaction volume. The large amount of input, ensuring the maintenance of variability, was checked by analysis of 4 λl of the "unamplified" PCR-mixture on agarose gel.

For the construction of the primary heavy chain and the two primary light chain repertoires, the PCR-products, appended with restriction sites, were gel purified prior to digestion and the different $V_H$-, $V_\kappa$- and $V_\lambda$-families combined into three groups. The $V_\kappa C_\kappa$- and $V_\lambda C_\lambda$-fragments were digested with ApaLI and AscI, and cloned into the phagemid vector pCES1. The $V_H$-fragments, 1.5 μg in total, were digested with SfiI and BstEII and ligated in a 100-200 μl reaction mixture with 9 U $T_4$-DNA ligase at room temperature to 4 μg, gel-purified vector pUC119-CES1 (similar to vector pCES1, but with the pIII gene deleted). The desalted ligation mixture for light or heavy chain pools was used for electroporation of the *E. coli* strain TG1, to create the one-chain libraries.

The Fab library was obtained by cloning of $V_H$ fragments, digested from plasmid-DNA prepared from the heavy chain repertoires, into the plasmid collection containing the light chain repertoires. Plasmid DNA isolated from at least 3×10⁹ bacteria of the $V_H$ library was digested with SfiI and BstEII for cloning in the vector that already contained λ and κ light chain libraries. To retain clones with internal BstEII site in the Vλ__ (this site is relatively frequent in some λ germline V-segments (Persic, et al., (1997) *Gene* 187, 9-18), and also in the constant domain of one of the λ families), the cloning of $V_H C_{H1}$ in the λ light chain repertoire containing vector was also carried out using SfiI and NotI cloning sites, to create a less restriction-biased $V_\lambda$ libary.

The rescue of phagemid particles with helper phage M13-K07 was performed according to (Marks, et al., (1991) J. Mol. Biol. 222, 581-597) on 10-L scale, using representative numbers of bacteria from the library for inoculation, to ensure the presence of at least 10 bacteria from each clone in the start inoculum. For selections, 10¹³ cfu's (colony forming units) were used with antigens immobilised in immunotubes (Maxisorp tubes, Nunc) (Marks, et al., (1991) J. Mol. Biol. 222, 581-597) or with soluble biotinylated antigens (Hawkins, et al., (1992b) J. Mol. Biol. 226, 889-896). The amount of the immobilised antigens tetanus toxoid and the hapten phenyl-oxazolone (conjugated to BSA in a ratio of 17 to 1) was reduced 10-fold during subsequent selection rounds, starting at 100 μg/ml at round 1. Capture with biotinylated antigen in solution was used for a 100-mer peptide encoding five copies of the tandem repeat of MUC1 (Henderikx, et al., (1998) *Cancer Res.* 58, 4324-4332), or with human Chorionic Gonadotropin (hCG), human Luteinizing Hormone (hLH), human Follicle Stimulating Hormone (hFSH) and its chimeric derivative (hFSH-CTP, containing the carboxy terminal peptide from the hCG β-subunit fused to the β-subunit of hFSH). Antigens were biotinylated at a ratio of ten to twenty molecules NHS-Biotin (Pierce) per molecule antigen according to the suppliers recommendations. Unless stated otherwise, the antigens were used for selection at concentrations of 100 nM, 30 nM and 10 nM during round 1, 2 and 3 respectively. For hFSH-CTP 50, 15 and 10 nM was used respectively; for MUC1 peptide, 500, 100, 20 and 5 nM was used.

Soluble Fab was produced from individual clones as described before (Marks, et al., (1991) J. Mol. Biol. 222, 581-597). Culture supernatants were tested in ELISA with directly coated antigen or indirectly captured biotinylated antigen via immobilised biotinylated BSA-streptavidin. Tetanus toxoid and phOx-BSA were coated at 10 μg/ml in 0.1 M $NaHCO_3$ pH 9.6 for 16 h at 4° C. For coating of hCG and hFSH-CTP a concentration of 4 μg/ml in 50 mM $NaHCO_3$ pH 9.6 was used. For capture of biotinylated antigens, biotinylated BSA was coated at 2 μg/ml in PBS during 1 h at 37° C. After 3 washes with PBS-0.1% (v/v) Tween 20 (PBST), plates were incubated during 1 h with streptavidin (10 μg/ml in PBS/0.5% gelatin) (Henderikx, et al., (1998) *Cancer Res.* 58, 4324-4332). Following washing as above, biotinylated antigen was added for an overnight incubation at 4° C. at a concentration of 0.5 μg/ml for MUC-1 peptide, 3 μg/ml for hLH, and 0.6 μg/ml for hFSH (binding to hCG was tested with directly coated antigen). The plates were blocked during 30 min at room temperature with 2% (w/v) semi-skimmed milk powder (Marvel) in PBS. The culture supernatant was diluted 1 or 5-fold in 2% (w/v) Marvel/PBS and incubated 2 h; bound Fab was detected with anti-myc antibody 9E10 (5 μg/ml) recognising the myc-peptide tag at the carboxyterminus of the heavy Fd chain, and rabbit anti-mouse-HRP conjugate (DAKO) (Marks, et al., (1991) J. Mol. Biol. 222, 581-597). Following the last incubation, staining was performed with tetramethylbenzidine (TMB) and $H_2O_2$ as substrate and stopped by adding half a volume of 2 N $H_2SO_4$; the optical density was measured at 450 nm. Clones giving a positive signal in ELISA (over 2× the background), were analysed by BstNI-fingerprinting of the PCR-products obtained by amplification with the oligonucleotide primers M13-reverse and geneIII-forward (Marks, et al., (1991) J. Mol. Biol. 222, 581-597).

Large-scale induction of soluble Fab fragments from individual clones was performed on 50 ml scale in 2×TY containing 100 μg/ml ampicillin and 2% glucose. After growth at 37° C. to an $OD_{600}$ of 0.9, the cells were pelleted (10 min at 2,934×g) and resuspended in 2×TY with ampicillin and 1 mM IPTG. Bacteria were harvested after 3.5 h growing at 30° C. by centrifugation (as before); periplasmic fractions were prepared by resuspending the cell pellet in 1 ml ice cold PBS. After 2 to 16 h rotating head-over-head at 4° C., the spheroplasts were removed by two centrifugation steps: after spinning during 10 min at 3,400×g, the supernatant was clarified by an additional centrifugation step during 10 min at 13,000×g in an eppendorf centrifuge. The periplasmic fraction obtained was directly used for determination of fine specificities by surface plasmon resonance or for western blot studies.

For sequencing, plasmid DNA was prepared from 50 ml cultures grown at 30° C. in LB-medium, containing 100 μg/ml ampicillin and 2% glucose, using the QIAGEN midikit (Qiagen). Sequencing was performed with the thermocycling kit (Amersham) with CY5-labeled primers CH1FOR (5'-GTC CTT GAC CAG GCA GCC CAG GGC-3'—SEQ ID NO: 3) and M13REV (5'-CAG GAA ACA GCT ATG AC-3'—SEQ ID NO: 4); samples were run on the ALF-Express (Pharmacia). V-gene sequences were aligned to V-base (Tomlinson et al., V-BASE, MRC Centre for Protein Engineering, 1997, http://www.mrc-cpe.cam.ac.uk/imt-doc/public/INTRO.html) or the Sanger Centre (Sanger Centre Germline Query, 1997, http//www.sanger.ac.uk/Data Search/gq-search.html).

An hCG-preparation purified from urine and immunoaffinity purified recombinant hLH, hFSH and hFSH-CTP produced in CHO-cells (Matzuk, et al., (1989) *J. Cell. Biol.* 109, 1429-1438; Muyan, et al., (1996) *Mol. Endocrinol.* 10, 1678-1687) were used for western blot studies as was described (Moyle, et al., (1990) *J. Biol. Chem.* 265, 8511-8518). Between 0.5 and 1 µg of each hormone was loaded per lane; proteins were diluted in non-reducing sample buffer and boiled during 5 min or directly applied on gel without heat-treatment; proteins were transferred to blotting membrane by electrotransfer. Blots were subsequently incubated for 16 h at room temperature with a 10-fold diluted periplasmic fraction in PBS/4% Marvel. Bound Fab was detected with anti-myc antibody 9E10 (5 µg/ml) and 4,000-fold diluted anti-mouse alkaline phosphatase-conjugate (Promega), using the substrates 5-bromo-1-chloro-3-indolyl phosphate (BCIP) and nitro blue tetrazolium (NBT) (Boehringer Mannheim) for visualisation.

The specificity of the Fab's was further characterised by surface plasmon resonance (BIAcore 2000, Biacore). Recombinant hLH, hFSH and the urinary hCG were immobilised on the flow-cells of a CM-chip using the NHS/EDC-kit (Pharmacia), yielding a surface of 1906 RU for hLH, 1529 RU for hFSH and 1375 RU for hCG. Periplasmic fractions were diluted three-fold in Hepes Buffered Saline (HBS; 10 mM Hepes, 3.4 mM EDTA, 150 mM NaCl, 0.05% (v/v) surfactant P20, pH 7.4) and analysed using a flow rate of 10 µl/min.

Fab's were obtained by refolding of the total bacterial proteins from a 50 ml culture (de Haard, et al., (1998) *Protein Eng.*, 11:1267-1276). Briefly, the pelleted cells from a 50 ml induced bacterial culture were resuspensed in 8 ml 8 M urea (in PBS). After sonication, the mixture was rotated head over head for 30 min and insoluble material was removed by centrifugation for 30 min at 13,000×g. The supernatant was dialysed against PBS with four buffer changes. Insoluble proteins were removed by centrifugation and the flow through fraction, obtained by filtration through a 0.2 µm membrane, was immediately loaded on an hCG column (bed volume 0.3 ml). The column material was prepared by coupling 8.4 mg protein to one gram Tresyl sepharose according to the suppliers instructions (Pierce). The column (1 ml column material) was washed with 10 volumes 100 mM Tris, 500 mM NaCl pH 7.5, subsequently with 10 volumes 100 mM Tris/500 mM NaCl pH 9.5 and with 2 volumes 0.9% NaCl, bound Fab was eluted with two volumes 0.1 M TEA and immediately neutralised with 0.5 volume 1M Tris pH 7.5.

The Fab fraction was dialysed against PBS using a Microcon 30 spin dialysis filter (Amicon). Finally, a gel-filtration analysis was carried out on a Superdex 75HR column (Pharmacia). The yield was determined by measuring the optical density at 280 nm (using a molar extinction coefficient of 13 for Fab's).

The kinetics of binding were analysed by surface plasmon resonance on three different hCG surfaces (303 RU, 615 RU and 767 RU immobilised, with 4955 RU BSA on a separate flow cell as a negative control). Fab present in crude periplasmic extracts was quantified on a high density surface of purified anti-human-Fab polyclonal antibody (Pierce) as described (Kazemier, et al., (1996) *J. Immunol. Methods* 194, 201-209). Anti-hCG Fab's controls were purified by affinity chromatography on hCG columns as described above and used to calibrate the system.

The Fab library was constructed in two-steps. In the first step, variable region gene pools were amplified from approx. $4 \times 10^8$ B-cells from the PBLs of four healthy donors, and, as a source of possibly more heavily mutated IgM antibodies, from a segment of a (tumor-free) spleen removed from a patient with gastric carcinoma, containing approximately $1.5 \times 10^8$ B-cells (Roit, et al., (1985) *Immunology*, Gower Medical Publishing, Ltd., London). Only IgM-derived $V_H$ segments were amplified by using an amplification with an oligonucleotide primer located in the first constant domain of this isotype. These products were cloned into phagemid vector pCES1 for $V_L$, and in pUC119-CES1 for $V_H$ (cloning was more efficiently in the smaller sized vector, in which gene III was deleted). The PBL and spleen derived $V_H$, $V_\kappa$ and $V_\lambda$-libraries were cloned separately to maintain diversity, to yield one-chain libraries in size typical for libraries made by cloning of PCR-fragments (Marks, et al., (1991) *J. Mol. Biol.* 222, 581-597): $1.75 \times 10^8$ individual clones for the heavy chain, $9.4 \times 10^7$ clones for $V_\kappa$, and $5.2 \times 10^7$ clones for $V_\lambda$. In the second step, the heavy chain fragments were digested from plasmid DNA isolated from the primary $V_H$ repertoire, and cloned into the vector containing the light chain repertoires (again separately for PBL and spleen derived repertoire). The libraries were combined using this efficient cloning procedure, to create a naVve Fab repertoire with $3.7 \times 10^{10}$ individual clones ($4.3 \times 10^{10}$ recombinant clones, 86% of which have a full-length Fab insert), with 70% of clones harbouring a kappa light chain, 30% a lambda chain. All of 20 clones with full length Fab insert tested scored positive in dot-blot analysis with the 9E10 antibody to indicating an expression level of soluble Fab of at least 0.2 mg/L.

We evaluated the library by selection with different antigens. First, the results from three model antigens, the protein tetanus toxoid, the hapten 2-phenyloxazol-5-one (phOx) (Griffiths, et al., (1984) *Nature* 312, 271-275, and the peptide MUC1, are discussed. Three rounds of biopanning on tetanus toxoid yielded a diverse set of ELISA positive Fab's, in a series of 47 tetanus toxoid binding Fab's, at least 21 were different with regard to BstNI-fingerprint. Similarly, an extensive panel of phOx-specific Fab's was retrieved after three rounds of panning: at least 24 different clones were identified in a series of 50 ELISA positive clones. Solution capture with biotinylated MUC1 peptide resulted in the selection of 14 different antibody fragments out of 37 ELISA-positive clones selected after 3 rounds.

As a more stringent test panel of antigens to assay the performance of the library, we chose to derive antibodies to three structurally related glycoproteins: human Chorionic Gonadotropin (hCG), human Luteinizing Hormone (hLH) and human Follicle Stimulating Hormone (hFSH) (reviewed in (Cole, (1997) *Clin. Chem.* 43, 2233-2243)). These hormones are heterodimers sharing an identical α-chain with 92 amino acid residues, but have β-subunits of different composition and length. The β-chain of hCG contains 145 amino acid residues, and the one from hLH only 121 residues, the latter showing 85% homology to β-hCG. The β-chain of hFSH is only 111 amino acids and shares 36% of the residues with hCG. Antibodies that specifically detect hCG have been used extensively in pregnancy tests (Cole, (1997) *Clin. Chem.* 43, 2233-2243) and for cancer diagnosis (Masure, et al., (1981) *J. Clin. Endocrinol. Metab.* 53, 1014-1020; Papapetrou, et al., (1980) *Cancer* 45, 2583-2592). A large set of antibodies to these targets would extend the limited number of hormone specific antibodies (especially against hLH), obtained using the hybridoma technology (Cole, (1997) *Clin. Chem.* 43, 2233-2243). The human origin of the antibodies might be beneficial when using these for imaging or therapy of testicular and bladder cancer (Masure, et al., (1981) *J. Clin. Endocrinol. Metab.* 53, 1014-1020; Papapetrou, et al., (1980) *Cancer* 45, 2583-2592).

Selections were thus performed on biotinylated urinary hCG, recombinant hLH, hFSH and hFSH-CTP (the latter is a chimeric molecule containing the carboxy terminal peptide of β-hCG fused to the α-chain of FSH (Fares, et al., (1992) *Proc. Natl. Acad. Sci. U.S.A* 89, 4304-4308)). The highest degree of enrichment in respect to the increase in the number of eluted phage particles in round 3 versus round 1 was found for hCG (10,000-fold), followed by hFSH-CTP (1,000-fold), hFSH (300-fold) and hLH (150-fold). Polyclonal phage of selected populations were tested for binding using sensorchips containing immobilised hormones (Schier, et al., (1996) *Hum. Antibodies Hybridomas* 7, 97-105). Polyclonal phage selected with hCG showed binding after rounds two and three of selection to all three proteins, i.e., hCG, hLH, and hFSH, with the strongest signal visible for hCG. Similar analysis of the polyclonal phage populations selected for three rounds on hFSH showed a dominance of hFSH-specific binding, while selections on hFSH-CTP yielded binders to both hFSH and hCG. Selections on hLH yielded antibodies reactive with hFSH and hCG. Thus, this polyclonal phage screening provides a rapid test to check the overall quality of the clones in the selected repertoire, and may also be used to guide the choice of the conditions for the next selection round (Schier, et al., (1996) *Hum. Antibodies Hybridomas* 7, 97-105).

ELISA of monoclonal phage antibodies revealed that three rounds of selection with hCG indeed resulted in the isolation of a high percentage (74%) of clones positive for the gonadotropin. 27% of these clones were hLH cross-reactive; none were reactive against streptavidin. BstNI-fingerprint analysis of the ELISA-positive clones revealed a high degree of diversity (8 different patterns). From a representative hCG-specific (coded CG#4F) and hLH cross-reactive (CG#5C) clone, the specificity was tested in BIAcore using unpurified soluble Fab fragments. Clone CG#4F gave a high response on hCG, with no visible binding to either hLH or hFSH-CTP. In contrast, clone CG#5C bound to hCG and hLH, but not to hFSH-CTP. Western blots, with the different hormones in non-reduced form, showed the specific recognition of the β-subunit of hCG by clone CG#4F, while the cross-reactive clone CG#5C reacted with the β-subunit of both hCG and hLH.

Selection with the hormone hLH resulted in the isolation of hLH-specific and hCG cross-reactive clones. Examination of individual clones from selection round three in ELISA revealed a large fraction of hLH specific clones (69%), and a minor group of cross-reactive clones (16%); no streptavidin reactive clones were selected. Within the group of specific clones, a large array of different species (>21) could be discriminated with fingerprint analysis; however, all cross-reactive species had a single pattern. The unique hLH specificity was confirmed for representative clones LH#2H and LH#3G, shown in surface plasmon resonance; and on western blot. LH#3G only recognises the intact α/β-heterodimer of hLH. Two representative clones of a pan-reactive antibody in ELISA, coded LH#1C and LH#3F, reacted in BIAcore with hFSH-CTP, hCG and hLH, and in western blot analysis with the α-chains from all three hormones.

When hFSH was used as antigen during selection, 6 different antibodies were isolated from the library, with one type, represented by clone FS#8B, dominating the selected population. This Fab only recognised hFSH in BIAcore, and, as western blot analysis demonstrated, in particular its β-unit. Further, the specificity of an α-chain binding clone, SC#2B, was confirmed in BIAcore and western blot.

Upon selection with FSH-CTP 7 different α-chain specific Fab's were identified by fingerprint analysis, from which the clones coded SC#2B, SC#2F, SC#2G and SC#4G were examined in more detail. Immunoblot analysis with the recombinant Fab as detecting antibody confirmed the α-chain specificity.

The affinities and off-rates of affinity purified hCG reactive Fab's LH#1C, SC#2B, LH#3F and CG#5C were determined. The off-rates for most Fab's were in the order of $10^{-2}$ and $10^{-3}$ S$^{-1}$. The off-rate values obtained using crude periplasmic fractions were in good agreement with the values found for the purified Fab's, validating the utility of the off-rate screen with unpurified Fab fragments. The affinities, 23 nM and 38 nM for the α-subunit specific antibody LH#1C and the β-subunit hCG/hLH-cross reactive antibody CG#5C respectively, are comparable to the affinity of antibodies selected from a murine immune phage antibody library (H. d. H., B. Kazemier, et al., unpublished); the top affinity, 2.7 nM for the α-chain specific Fab SC#2B, approaches the values of the best anti-hCG monoclonal antibodies (H. d. H., B. Kazemier, et al., unpublished).

The aim of this procedure is to select and enrich for phage-antibodies to an antigen coated on the surface of immunotubes. The antigen is coated to the immunotube (e.g., a Nunc-immunotube) and incubated with the phage library. Non-bound phage are washed away and the binding phage are eluted, therefore the phage library becomes enriched for phage antibodies that specifically bind the antigen.

The aim of this procedure is to biotinylate proteins or peptides. At neutral pH or above, primary amine-groups react with NHS-SS-Biotin, and N-hydroxysulfosuccinimide is released. The N-terminal free NH$_2$-groups as well as lysines (K) of the protein react with NHS-S-S-Biotin, in this pH range.

NHS-SS-Biotin is a unique biotin analog with an extended spacer arm of approximately 24.3 Å in length, the spacer arm of NHS-LC-Biotin is 22.4 Å. These long chain analogs reduce steric hindrances associated with binding of biotinylated molecules to avidin or streptavidin.

The presence of the S-S linker in NHS-S-S-Biotin enables disruption of binding using reducing agents (DTT, DTE, B-mercaptoethanol). NHS-LC-Biotin is used when biotinylated protein/peptide is needed that is not sensitive to reducing agents.

The aim of this procedure is to select phage antibodies against a biotinylated antigen. The selection is done in solution, and can be used to select phage antibodies against antigens that are prone to denaturation when coated onto solid surfaces.

First the biotinylated antigen is incubated with the phage antibody library. After addition of the Dynabeads (Dynal) coated with streptavidin, the biotin of the antigen-antibody-complex will bind to the streptavidin. This Dynabeadantigen-antibody-complex is pulled out with a magnet (e.g., a Dynal magnet) and therefore should contain the specific antibodies.

The aim of this procedure is to select for those antibodies out of a library that bind to antigens present in the cell membrane, using adherent growing cells or cells in suspension. The method can be used for selection of antibodies against targets expressed on (tumor) cell lines.

By incubating whole cells, organelles, or membrane fractions with a high variety phage antibody repertoire, such as the Fab Libraries of the invention (concentrated by PEG precipitation), only (or preferentially) relevant antibodies, to one of the molecules exposed on the surface of the cellular membrane(s), will be retained while not binding phage antibodies are separated from the antibodies bound to the cells, organelles or membrane fractions (by methods well known in the art for separating cells, organelles or membrane fractions from molecules in solution). The retained phage population is enriched for those clones which are specific for cell related molecules. In principle the following factors will positively influence the enrichment of individual clones: Affinity, antigen abundance, and low toxicity of the antibody construct to TG1 host.

The aim of this procedure is to prepare soluble antibody fragments from the periplasm of *E. coli*. In the periplasm there is: less protease activity, less contaminating proteins than in the cytoplasm or supernatants, and the antibody is more concentrated. Therefore, periplasmic preparations are more stable and more pure than culture supernatants.

As a consequence of induction of phagemid containing bacterial cultures in low glucose medium with IPTG, soluble antibody fragments are produced and directed to the periplasm where they are concentrated within 4 hours. Overnight culturing in these circumstances will make the bacterial membrane leaky and antibodies will be found in the supernatant. For preparation of periplasmic fractions, the bacterial cell wall is first lysed by cold osmotic shock (icecold TES) and then rapidly diluted in a chilled solution of low osmotic strength (TES/$H_2O$). The EDTA makes the outer membrane more permeable, and the cold inhibits protease activity. Subsequently, the bacterial cells are spun down and the supernatant then contains the periplasmic proteins.

The antibodies in the periplasmic fraction can be used as a 'crude extract' or the antibodies can be purified by conventional means well known in the art, for e.g., those recited in Section 5.6 and 5.7.

The aim of this procedure is to purify antibodies labeled with a His6 tag from periplasmic fractions of Fabs made as described in Example 6.18.

Immobilized metal affinity chromatography (IMAC) for the purification of recombinant 6×His-tagged proteins under native conditions: Recombinant histidine tagged proteins are captured on a chelated metal containing resin through coordination of free N-atoms of the histidines to the metal (mostly $Ni^{2+}$ or $Co^{2+}$). After washing away contaminating proteins and other cell constituents, the his-tagged protein is specifically eluted from the resin with imidazol which competes for the binding of histidine-residues to the metal ion.

The present invention is not to be limited in scope by the exemplified embodiments which are intended as illustrations of single aspects of the invention, and compositions and methods which are functionally equivalent are within the scope of the invention. Indeed, numerous modifications and variations in the practice of the invention are expected to occur to those skilled in the art upon consideration of the present preferred embodiments. Consequently, the only limitations which should be placed upon the scope of the invention are those which appear in the appended claims.

All references cited within the body of the instant specification are hereby incorporated by reference in their entirety.

---

The invention claimed is:

1. A method for making a Fab library, comprising:
providing a plurality of vectors, wherein each of the plurality of vectors comprises
(a) a first cloning region, and a second cloning region, wherein each cloning region comprises at least one, for the vector unique, restriction enzyme cleavage site, and each cloning region is 5' flanked by a ribosome binding site and a signal sequence
(b) a polynucleotide encoding an anchor region located 3' of the second cloning region, and
(c) a polynucleotide encoding a heavy chain constant region or a portion thereof located between the vector unique restriction enzyme cleavage site of the second cloning region and the anchor region;
introducing into the first cloning region a member of a first plurality of variable polynucleotides encoding a first plurality of variable polypeptides, each of which comprises an antibody light chain variable region, wherein each of the first plurality of variable polypeptides further comprises a light chain constant region fused to the C-terminus of the light chain variable region, separately introducing into the second cloning region of each vector a member of a second plurality of variable polynucleotides encoding a second plurality of variable polypeptides, each of which comprises an antibody heavy chain variable region, thereby producing a plurality of vectors encoding the first and second plurality of variable polypeptides, and introducing the plurality of vectors encoding the first and second plurality of variable polypeptides into host cells to provide a plurality of capsid particles, each comprising a member of the first plurality of variable polynucleotides and a member of the second plurality of variable polynucleotides, wherein the polypeptides encoded by the members of the first and second plurality of variable polynucleotides form a Fab molecule;

wherein the first and second plurality of variable polypeptides form a plurality of Fab molecules.

2. The method of claim 1, wherein the plurality of vectors in the library encode at least $10^9$ different Fab molecules.

3. The method of claim 2, wherein the plurality of vectors in the library encode at least $10^{10}$ different Fab molecules.

4. The method of claim 3, wherein the plurality of vectors in the library encode at least $3.7 \times 10^9$ different Fab molecules.

5. The method of claim 1, wherein the plurality of capsid particles comprise at least $10^9$ different Fab molecules.

6. The method of claim 5, wherein the plurality of capsid particles comprise at least $10^{10}$ different Fab molecules.

7. The method of claim 6, wherein the plurality of capsid particles comprise at least $3.7 \times 10^{10}$ different Fab molecules.

8. The method of claim 1, further comprising:
amplifying the first plurality of variable polynucleotides with a first set of primers, and
amplifying the second plurality of variable polynucleotides with a second set of primers, wherein each set of the primers comprises oligonucleotides are homologous to the 5' and 3' end of polynucleotides encoding antibody variable regions or parts thereof for amplifying variable polynucleotide pools from natural or synthetic sources of antibody genes.

9. The method of claim 1, wherein the anchor region comprises a phage coat protein.

10. The method of claim 9, wherein the coat protein is a gene III product.

11. The method of claim 10, wherein the coat protein comprises minor coat protein III of filamentous phage $f_d$.

12. A method for making a Fab library, comprising:
providing a plurality of vectors, wherein each of the plurality vectors comprises
(a) a first cloning region and a second cloning region, wherein each cloning region comprises at least one, for the vector unique, restriction enzyme cleavage site, and each cloning region is 5' flanked by a ribosome binding site and a signal sequence,
(b) a polynucleotide encoding an anchor region located 3' of the second cloning region,
(c) a polynucleotide encoding a heavy chain constant region or a portion thereof located between the vector unique restriction enzyme cleavage site of the second cloning region and the anchor region, and
(d) a polynucleotide encoding a light chain constant region located 3' end of the first cloning region;

introducing into the first cloning region a member of a first plurality of variable polynucleotides encoding a first plurality of variable polypeptides, each of which comprises an antibody light chain variable region, wherein each of the first plurality of variable polypeptides further comprises a light chain constant region fused to the C-terminus of the light chain variable region, separately introducing into the second cloning region of each vector a member of a second plurality of variable polynucleotides encoding a second plurality of variable polypeptides, each of which comprises an antibody heavy chain variable region, thereby producing a plurality of vectors encoding the first and second plurality of variable polypeptides, and introducing the plurality of vectors encoding the first and second plurality of variable polypeptides into host cells to provide a plurality of capsid particles, each comprising a member of the first plurality of variable polynucleotides and a member of the second plurality of variable polynucleotides, wherein the polypeptides encoded by the members of the first and second plurality of variable polynucleotides form a Fab molecule;

wherein the first and second plurality of variable polypeptides form a plurality of Fab molecules.

13. The method of claim 12, wherein the first plurality of variable polypeptides and the second plurality of variable polypeptides form at least $10^9$ different Fab molecules.

14. The method of claim 13, wherein the first plurality of variable polypeptides and the second plurality of variable polypeptides form at least $10^{10}$ different Fab molecules.

15. The method of claim 14, wherein the first plurality of variable polypeptides and the second plurality of variable polypeptides form at least $3.7 \times 10^9$ different Fab molecules.

16. The method of claim 12, wherein the first plurality of variable polypeptides and the second plurality of variable polypeptides form at least $10^9$ different Fab molecules.

17. The method of claim 12, wherein the first plurality of variable polypeptides and the second plurality of variable polypeptides form at least $10^{10}$ different Fab molecules.

18. The method of claim 17, wherein the first plurality of variable polypeptides and the second plurality of variable polypeptides form at least $3.7 \times 10^{10}$ different Fab molecules.

19. The method of claim 12, further comprising:
amplifying the first plurality of variable polynucleotides with a first set of primers, and
amplifying the second plurality of variable polynucleotides with a second set of primers, wherein each set of the primers comprises oligonucleotides are homologous to the 5' and 3' end of polynucleotides encoding antibody variable regions or parts thereof for amplifying variable polynucleotide pools from natural or synthetic sources of antibody genes.

20. The method of claim 12, wherein the anchor region comprises a phage coat protein.

21. The method of claim 20, wherein the coat protein is a gene III product.

22. The method of claim 21, wherein the coat protein comprises minor coat protein III of filamentous phage fd.

* * * * *

SEQUENCE LISTING

```
<160> NUMBER OF SEQ ID NOS: 71

<210> SEQ ID NO 1
<211> LENGTH: 11
<212> TYPE: PRT
<213> ORGANISM: Artificial Sequence
<220> FEATURE:
<223> OTHER INFORMATION: Description of Artificial Sequence:
      Illustrative peptide

<400> SEQUENCE: 1

Glu Gln Lys Leu Ile Ser Glu Glu Asp Leu Asn
1               5                   10

<210> SEQ ID NO 2
<211> LENGTH: 21
<212> TYPE: DNA
<213> ORGANISM: Artificial Sequence
<220> FEATURE:
<223> OTHER INFORMATION: Description of Artificial Sequence: Primer

<400> SEQUENCE: 2
cgatctaaag ttttgtcgtc t                                              21

<210> SEQ ID NO 3
<211> LENGTH: 24
<212> TYPE: DNA
```

```
<213> ORGANISM: Artificial Sequence
<220> FEATURE:
<223> OTHER INFORMATION: Description of Artificial Sequence: Primer

<400> SEQUENCE: 3
gtccttgacc aggcagccca gggc                                          24

<210> SEQ ID NO 4
<211> LENGTH: 17
<212> TYPE: DNA
<213> ORGANISM: Artificial Sequence
<220> FEATURE:
<223> OTHER INFORMATION: Description of Artificial Sequence: Primer

<400> SEQUENCE: 4
caggaaacag ctatgac                                                  17

<210> SEQ ID NO 5
<211> LENGTH: 6
<212> TYPE: PRT
<213> ORGANISM: Artificial Sequence
<220> FEATURE:
<223> OTHER INFORMATION: Description of Artificial Sequence: 6X-His tag

<400> SEQUENCE: 5

His His His His His His
1               5

<210> SEQ ID NO 6
<211> LENGTH: 349
<212> TYPE: DNA
<213> ORGANISM: Artificial Sequence
<220> FEATURE:
<223> OTHER INFORMATION: Synthetic Polynucleotide

<400> SEQUENCE: 6
ttattcgcaa ttcctttagt tgttcctttc tattctcaca gtgcacaggt ccaactgcag    60
gtcgacctcg agatcaaacg tggaactgtg ggagagtgtt aataaggcgc gccaattcta   120
tttcaaggag acagtcataa tgaaatacct attgcctacg gcagccgctg gattgttatt   180
actcgcggcc cagccggcca tggcccaggt gcagctgcag agagcgggg tcaccgtctc     240 aagcgcctcc accaaatctt gtgcggccgc acatcatcat catcatcacg gggccgcaga   300
acaaaaactc atctcagaag aggatctgaa tggggccgca tagactgtt               349

<210> SEQ ID NO 7
<211> LENGTH: 33
<212> TYPE: PRT
<213> ORGANISM: Artificial Sequence
<220> FEATURE:
<223> OTHER INFORMATION: Synthetic Construct

<400> SEQUENCE: 7

Leu Phe Ala Ile Pro Leu Val Val Pro Phe Tyr Ser His Ser Ala Gln
1               5                   10                  15

Val Gln Leu Gln Val Asp Leu Glu Ile Lys Arg Gly Thr Val Gly Glu
            20                  25                  30

Cys

<210> SEQ ID NO 8
<211> LENGTH: 67
<212> TYPE: PRT
```

<210> SEQ ID NO 8
...

<400> SEQUENCE: 8

Met Lys Tyr Leu Leu Pro Thr Ala Ala Ala Gly Leu Leu Leu Leu Ala
1               5                   10                  15

Ala Gln Pro Ala Met Ala Gln Val Gln Leu Gln Glu Ser Gly Val Thr
            20                  25                  30

Val Ser Ser Ala Ser Thr Lys Ser Cys Ala Ala Ala His His His
        35                  40                  45

His His Gly Ala Ala Glu Gln Lys Leu Ile Ser Glu Glu Asp Leu Asn
    50                  55                  60

Gly Ala Ala
65

<210> SEQ ID NO 9
<211> LENGTH: 24
<212> TYPE: DNA
<213> ORGANISM: Artificial Sequence
<220> FEATURE:
<223> OTHER INFORMATION: Description of Artificial Sequence: Primer

<400> SEQUENCE: 9
tggaagaggc acgttctttt cttt                                          24

<210> SEQ ID NO 10
<211> LENGTH: 24
<212> TYPE: DNA
<213> ORGANISM: Artificial Sequence
<220> FEATURE:
<223> OTHER INFORMATION: Description of Artificial Sequence: Primer

<400> SEQUENCE: 10
acactctccc ctgttgaagc tctt                                          24

<210> SEQ ID NO 11
<211> LENGTH: 23
<212> TYPE: DNA
<213> ORGANISM: Artificial Sequence
<220> FEATURE:
<223> OTHER INFORMATION: Description of Artificial Sequence: Primer

<400> SEQUENCE: 11
tgaacattct gtaggggcca ctg                                           23

<210> SEQ ID NO 12
<211> LENGTH: 23
<212> TYPE: DNA
<213> ORGANISM: Artificial Sequence
<220> FEATURE:
<223> OTHER INFORMATION: Description of Artificial Sequence: Primer

<400> SEQUENCE: 12
agagcattct gcaggggcca ctg                                           23

<210> SEQ ID NO 13
<211> LENGTH: 23
<212> TYPE: DNA
<213> ORGANISM: Artificial Sequence
<220> FEATURE:
<223> OTHER INFORMATION: Description of Artificial Sequence: Primer

<400> SEQUENCE: 13
cagrtgcagc tggtgcartc tgg 23

<210> SEQ ID NO 14
<211> LENGTH: 23
<212> TYPE: DNA
<213> ORGANISM: Artificial Sequence
<220> FEATURE:
<223> OTHER INFORMATION: Description of Artificial Sequence: Primer

<400> SEQUENCE: 14
saggtccagc tggtrcagtc tgg 23

<210> SEQ ID NO 15
<211> LENGTH: 23
<212> TYPE: DNA
<213> ORGANISM: Artificial Sequence
<220> FEATURE:
<223> OTHER INFORMATION: Description of Artificial Sequence: Primer

<400> SEQUENCE: 15
cagrtcacct tgaaggagtc tgg 23

<210> SEQ ID NO 16
<211> LENGTH: 23
<212> TYPE: DNA
<213> ORGANISM: Artificial Sequence
<220> FEATURE:
<223> OTHER INFORMATION: Description of Artificial Sequence: Primer

<400> SEQUENCE: 16
saggtgcagc tggtggagtc tgg 23

<210> SEQ ID NO 17
<211> LENGTH: 23
<212> TYPE: DNA
<213> ORGANISM: Artificial Sequence
<220> FEATURE:
<223> OTHER INFORMATION: Description of Artificial Sequence: Primer

<400> SEQUENCE: 17
gaggtgcagc tggtggagwc ygg 23

<210> SEQ ID NO 18
<211> LENGTH: 23
<212> TYPE: DNA
<213> ORGANISM: Artificial Sequence
<220> FEATURE:
<223> OTHER INFORMATION: Description of Artificial Sequence: Primer

<400> SEQUENCE: 18
caggtgcagc tacagcagtg ggg 23

<210> SEQ ID NO 19
<211> LENGTH: 23
<212> TYPE: DNA
<213> ORGANISM: Artificial Sequence
<220> FEATURE:
<223> OTHER INFORMATION: Description of Artificial Sequence: Primer

<400> SEQUENCE: 19
cagstgcagc tgcaggagtc sgg 23

<210> SEQ ID NO 20
<211> LENGTH: 23
<212> TYPE: DNA
<213> ORGANISM: Artificial Sequence

```
<220> FEATURE:
<223> OTHER INFORMATION: Description of Artificial Sequence: Primer

<400> SEQUENCE: 20
gargtgcagc tggtgcagtc tgg                                              23

<210> SEQ ID NO 21
<211> LENGTH: 23
<212> TYPE: DNA
<213> ORGANISM: Artificial Sequence
<220> FEATURE:
<223> OTHER INFORMATION: Description of Artificial Sequence: Primer

<400> SEQUENCE: 21
caggtacagc tgcagcagtc agg                                              23

<210> SEQ ID NO 22
<211> LENGTH: 23
<212> TYPE: DNA
<213> ORGANISM: Artificial Sequence
<220> FEATURE:
<223> OTHER INFORMATION: Description of Artificial Sequence: Primer

<400> SEQUENCE: 22
gacatccagw tgacccagtc tcc                                              23

<210> SEQ ID NO 23
<211> LENGTH: 23
<212> TYPE: DNA
<213> ORGANISM: Artificial Sequence
<220> FEATURE:
<223> OTHER INFORMATION: Description of Artificial Sequence: Primer

<400> SEQUENCE: 23
gatgttgtga tgactcagtc tcc                                              23

<210> SEQ ID NO 24
<211> LENGTH: 23
<212> TYPE: DNA
<213> ORGANISM: Artificial Sequence
<220> FEATURE:
<223> OTHER INFORMATION: Description of Artificial Sequence: Primer

<400> SEQUENCE: 24
gaaattgtgw tgacrcagtc tcc                                              23

<210> SEQ ID NO 25
<211> LENGTH: 23
<212> TYPE: DNA
<213> ORGANISM: Artificial Sequence
<220> FEATURE:
<223> OTHER INFORMATION: Description of Artificial Sequence: Primer

<400> SEQUENCE: 25
gatattgtga tgacccacac tcc                                              23

<210> SEQ ID NO 26
<211> LENGTH: 23
<212> TYPE: DNA
<213> ORGANISM: Artificial Sequence
<220> FEATURE:
<223> OTHER INFORMATION: Description of Artificial Sequence: Primer

<400> SEQUENCE: 26
gaaacgacac tcacgcagtc tcc                                              23
```

```
<210> SEQ ID NO 27
<211> LENGTH: 23
<212> TYPE: DNA
<213> ORGANISM: Artificial Sequence
<220> FEATURE:
<223> OTHER INFORMATION: Description of Artificial Sequence: Primer

<400> SEQUENCE: 27
gaaattgtgc tgactcagtc tcc                                            23

<210> SEQ ID NO 28
<211> LENGTH: 23
<212> TYPE: DNA
<213> ORGANISM: Artificial Sequence
<220> FEATURE:
<223> OTHER INFORMATION: Description of Artificial Sequence: Primer

<400> SEQUENCE: 28
cagtctgtgc tgactcagcc acc                                            23

<210> SEQ ID NO 29
<211> LENGTH: 23
<212> TYPE: DNA
<213> ORGANISM: Artificial Sequence
<220> FEATURE:
<223> OTHER INFORMATION: Description of Artificial Sequence: Primer

<400> SEQUENCE: 29
cagtctgtgy tgacgcagcc gcc                                            23

<210> SEQ ID NO 30
<211> LENGTH: 23
<212> TYPE: DNA
<213> ORGANISM: Artificial Sequence
<220> FEATURE:
<223> OTHER INFORMATION: Description of Artificial Sequence: Primer

<400> SEQUENCE: 30
cagtctgtcg tgacgcagcc gcc                                            23

<210> SEQ ID NO 31
<211> LENGTH: 21
<212> TYPE: DNA
<213> ORGANISM: Artificial Sequence
<220> FEATURE:
<223> OTHER INFORMATION: Description of Artificial Sequence: Primer

<400> SEQUENCE: 31
cartctgccc tgactcagcc t                                              21

<210> SEQ ID NO 32
<211> LENGTH: 23
<212> TYPE: DNA
<213> ORGANISM: Artificial Sequence
<220> FEATURE:
<223> OTHER INFORMATION: Description of Artificial Sequence: Primer

<400> SEQUENCE: 32
tcctatgwgc tgactcagcc acc                                            23

<210> SEQ ID NO 33
<211> LENGTH: 23
<212> TYPE: DNA
<213> ORGANISM: Artificial Sequence
<220> FEATURE:
<223> OTHER INFORMATION: Description of Artificial Sequence: Primer
```

-continued

<400> SEQUENCE: 33
tcttctgagc tgactcagga ccc                                           23

<210> SEQ ID NO 34
<211> LENGTH: 23
<212> TYPE: DNA
<213> ORGANISM: Artificial Sequence
<220> FEATURE:
<223> OTHER INFORMATION: Description of Artificial Sequence: Primer

<400> SEQUENCE: 34
cacgttatac tgactcaacc gcc                                           23

<210> SEQ ID NO 35
<211> LENGTH: 23
<212> TYPE: DNA
<213> ORGANISM: Artificial Sequence
<220> FEATURE:
<223> OTHER INFORMATION: Description of Artificial Sequence: Primer

<400> SEQUENCE: 35
caggctgtgc tgactcagcc gtc                                           23

<210> SEQ ID NO 36
<211> LENGTH: 23
<212> TYPE: DNA
<213> ORGANISM: Artificial Sequence
<220> FEATURE:
<223> OTHER INFORMATION: Description of Artificial Sequence: Primer

<400> SEQUENCE: 36
aattttatgc tgactcagcc cca                                           23

<210> SEQ ID NO 37
<211> LENGTH: 23
<212> TYPE: DNA
<213> ORGANISM: Artificial Sequence
<220> FEATURE:
<223> OTHER INFORMATION: Description of Artificial Sequence: Primer

<400> SEQUENCE: 37
cagrctgtgg tgacycagga gcc                                           23

<210> SEQ ID NO 38
<211> LENGTH: 23
<212> TYPE: DNA
<213> ORGANISM: Artificial Sequence
<220> FEATURE:
<223> OTHER INFORMATION: Description of Artificial Sequence: Primer

<400> SEQUENCE: 38
cwgcctgtgc tgactcagcc mcc                                           23

<210> SEQ ID NO 39
<211> LENGTH: 51
<212> TYPE: DNA
<213> ORGANISM: Artificial Sequence
<220> FEATURE:
<223> OTHER INFORMATION: Description of Artificial Sequence: Primer

<400> SEQUENCE: 39
accgcctcca ccgggcgcgc cttattaaca ctctcccctg ttgaagctct t            51

<210> SEQ ID NO 40

<211> LENGTH: 50
<212> TYPE: DNA
<213> ORGANISM: Artificial Sequence
<220> FEATURE:
<223> OTHER INFORMATION: Description of Artificial Sequence: Primer

<400> SEQUENCE: 40
accgcctcca ccgggcgcgc cttattatga acattctgta ggggccactg         50

<210> SEQ ID NO 41
<211> LENGTH: 50
<212> TYPE: DNA
<213> ORGANISM: Artificial Sequence
<220> FEATURE:
<223> OTHER INFORMATION: Description of Artificial Sequence: Primer

<400> SEQUENCE: 41
accgcctcca ccgggcgcgc cttattaaga gcattctgca ggggccactg         50

<210> SEQ ID NO 42
<211> LENGTH: 56
<212> TYPE: DNA
<213> ORGANISM: Artificial Sequence
<220> FEATURE:
<223> OTHER INFORMATION: Description of Artificial Sequence: Primer

<400> SEQUENCE: 42
gtcctcgcaa ctgcggccca gccggccatg gcccagrtgc agctggtgca rtctgg   56

<210> SEQ ID NO 43
<211> LENGTH: 56
<212> TYPE: DNA
<213> ORGANISM: Artificial Sequence
<220> FEATURE:
<223> OTHER INFORMATION: Description of Artificial Sequence: Primer

<400> SEQUENCE: 43
gtcctcgcaa ctgcggccca gccggccatg gccsaggtcc agctggtrca gtctgg   56

<210> SEQ ID NO 44
<211> LENGTH: 56
<212> TYPE: DNA
<213> ORGANISM: Artificial Sequence
<220> FEATURE:
<223> OTHER INFORMATION: Description of Artificial Sequence: Primer

<400> SEQUENCE: 44
gtcctcgcaa ctgcggccca gccggccatg gcccagrtca ccttgaagga gtctgg   56

<210> SEQ ID NO 45
<211> LENGTH: 56
<212> TYPE: DNA
<213> ORGANISM: Artificial Sequence
<220> FEATURE:
<223> OTHER INFORMATION: Description of Artificial Sequence: Primer

<400> SEQUENCE: 45
gtcctcgcaa ctgcggccca gccggccatg gccsaggtgc agctggtgga gtctgg   56

<210> SEQ ID NO 46
<211> LENGTH: 56
<212> TYPE: DNA
<213> ORGANISM: Artificial Sequence
<220> FEATURE:
<223> OTHER INFORMATION: Description of Artificial Sequence: Primer

<400> SEQUENCE: 46
gtcctcgcaa ctgcggccca gccggccatg gccgaggtgc agctggtgga gwcygg        56

<210> SEQ ID NO 47
<211> LENGTH: 56
<212> TYPE: DNA
<213> ORGANISM: Artificial Sequence
<220> FEATURE:
<223> OTHER INFORMATION: Description of Artificial Sequence: Primer

<400> SEQUENCE: 47
gtcctcgcaa ctgcggccca gccggccatg gcccaggtgc agctacagca gtgggg        56

<210> SEQ ID NO 48
<211> LENGTH: 56
<212> TYPE: DNA
<213> ORGANISM: Artificial Sequence
<220> FEATURE:
<223> OTHER INFORMATION: Description of Artificial Sequence: Primer

<400> SEQUENCE: 48
gtcctcgcaa ctgcggccca gccggccatg gcccagstgc agctgcagga gtcsgg        56

<210> SEQ ID NO 49
<211> LENGTH: 56
<212> TYPE: DNA
<213> ORGANISM: Artificial Sequence
<220> FEATURE:
<223> OTHER INFORMATION: Description of Artificial Sequence: Primer

<400> SEQUENCE: 49
gtcctcgcaa ctgcggccca gccggccatg gccgargtgc agctggtgca gtctgg        56

<210> SEQ ID NO 50
<211> LENGTH: 56
<212> TYPE: DNA
<213> ORGANISM: Artificial Sequence
<220> FEATURE:
<223> OTHER INFORMATION: Description of Artificial Sequence: Primer

<400> SEQUENCE: 50
gtcctcgcaa ctgcggccca gccggccatg gcccaggtac agctgcagca gtcagg        56

<210> SEQ ID NO 51
<211> LENGTH: 24
<212> TYPE: DNA
<213> ORGANISM: Artificial Sequence
<220> FEATURE:
<223> OTHER INFORMATION: Description of Artificial Sequence: Primer

<400> SEQUENCE: 51
tgaggagacg gtgaccaggg tgcc        24

<210> SEQ ID NO 52
<211> LENGTH: 24
<212> TYPE: DNA
<213> ORGANISM: Artificial Sequence
<220> FEATURE:
<223> OTHER INFORMATION: Description of Artificial Sequence: Primer

<400> SEQUENCE: 52
tgaagagacg gtgaccattg tccc        24

<210> SEQ ID NO 53
<211> LENGTH: 24
<212> TYPE: DNA

<213> ORGANISM: Artificial Sequence
<220> FEATURE:
<223> OTHER INFORMATION: Description of Artificial Sequence: Primer

<400> SEQUENCE: 53
tgaggagacg gtgaccaggg ttcc                                        24

<210> SEQ ID NO 54
<211> LENGTH: 24
<212> TYPE: DNA
<213> ORGANISM: Artificial Sequence
<220> FEATURE:
<223> OTHER INFORMATION: Description of Artificial Sequence: Primer

<400> SEQUENCE: 54
tgaggagacg gtgaccgtgg tccc                                        24

<210> SEQ ID NO 55
<211> LENGTH: 44
<212> TYPE: DNA
<213> ORGANISM: Artificial Sequence
<220> FEATURE:
<223> OTHER INFORMATION: Description of Artificial Sequence: Primer

<400> SEQUENCE: 55
accgcctcca ccagtgcact tgacatccag wtgacccagt ctcc                  44

<210> SEQ ID NO 56
<211> LENGTH: 44
<212> TYPE: DNA
<213> ORGANISM: Artificial Sequence
<220> FEATURE:
<223> OTHER INFORMATION: Description of Artificial Sequence: Primer

<400> SEQUENCE: 56
accgcctcca ccagtgcact tgatgttgtg atgactcagt ctcc                  44

<210> SEQ ID NO 57
<211> LENGTH: 44
<212> TYPE: DNA
<213> ORGANISM: Artificial Sequence
<220> FEATURE:
<223> OTHER INFORMATION: Description of Artificial Sequence: Primer

<400> SEQUENCE: 57
accgcctcca ccagtgcact tgaaattgtg wtgacrcagt ctcc                  44

<210> SEQ ID NO 58
<211> LENGTH: 44
<212> TYPE: DNA
<213> ORGANISM: Artificial Sequence
<220> FEATURE:
<223> OTHER INFORMATION: Description of Artificial Sequence: Primer

<400> SEQUENCE: 58
accgcctcca ccagtgcact tgatattgtg atgacccaca ctcc                  44

<210> SEQ ID NO 59
<211> LENGTH: 44
<212> TYPE: DNA
<213> ORGANISM: Artificial Sequence
<220> FEATURE:
<223> OTHER INFORMATION: Description of Artificial Sequence: Primer

<400> SEQUENCE: 59
accgcctcca ccagtgcact tgaaacgaca ctcacgcagt ctcc                  44

<210> SEQ ID NO 60
<211> LENGTH: 44
<212> TYPE: DNA
<213> ORGANISM: Artificial Sequence
<220> FEATURE:
<223> OTHER INFORMATION: Description of Artificial Sequence: Primer

<400> SEQUENCE: 60
accgcctcca ccagtgcact tgaaattgtg ctgactcagt ctcc        44

<210> SEQ ID NO 61
<211> LENGTH: 41
<212> TYPE: DNA
<213> ORGANISM: Artificial Sequence
<220> FEATURE:
<223> OTHER INFORMATION: Description of Artificial Sequence: Primer

<400> SEQUENCE: 61
accgcctcca ccagtgcaca gtctgtgctg actcagccac c        41

<210> SEQ ID NO 62
<211> LENGTH: 41
<212> TYPE: DNA
<213> ORGANISM: Artificial Sequence
<220> FEATURE:
<223> OTHER INFORMATION: Description of Artificial Sequence: Primer

<400> SEQUENCE: 62
accgcctcca ccagtgcaca gtctgtgytg acgcagccgc c        41

<210> SEQ ID NO 63
<211> LENGTH: 41
<212> TYPE: DNA
<213> ORGANISM: Artificial Sequence
<220> FEATURE:
<223> OTHER INFORMATION: Description of Artificial Sequence: Primer

<400> SEQUENCE: 63
accgcctcca ccagtgcaca gtctgtcgtg acgcagccgc c        41

<210> SEQ ID NO 64
<211> LENGTH: 39
<212> TYPE: DNA
<213> ORGANISM: Artificial Sequence
<220> FEATURE:
<223> OTHER INFORMATION: Description of Artificial Sequence: Primer

<400> SEQUENCE: 64
accgcctcca ccagtgcaca rtctgccctg actcagcct        39

<210> SEQ ID NO 65
<211> LENGTH: 44
<212> TYPE: DNA
<213> ORGANISM: Artificial Sequence
<220> FEATURE:
<223> OTHER INFORMATION: Description of Artificial Sequence: Primer

<400> SEQUENCE: 65
accgcctcca ccagtgcact ttcctatgwg ctgactcagc cacc        44

<210> SEQ ID NO 66
<211> LENGTH: 44
<212> TYPE: DNA
<213> ORGANISM: Artificial Sequence
<220> FEATURE:

-continued

```
<223> OTHER INFORMATION: Description of Artificial Sequence: Primer

<400> SEQUENCE: 66
accgcctcca ccagtgcact ttcttctgag ctgactcagg accc        44

<210> SEQ ID NO 67
<211> LENGTH: 41
<212> TYPE: DNA
<213> ORGANISM: Artificial Sequence
<220> FEATURE:
<223> OTHER INFORMATION: Description of Artificial Sequence: Primer

<400> SEQUENCE: 67
accgcctcca ccagtgcaca cgttatactg actcaaccgc c           41

<210> SEQ ID NO 68
<211> LENGTH: 41
<212> TYPE: DNA
<213> ORGANISM: Artificial Sequence
<220> FEATURE:
<223> OTHER INFORMATION: Description of Artificial Sequence: Primer

<400> SEQUENCE: 68
accgcctcca ccagtgcaca ggctgtgctg actcagccgt c           41

<210> SEQ ID NO 69
<211> LENGTH: 44
<212> TYPE: DNA
<213> ORGANISM: Artificial Sequence
<220> FEATURE:
<223> OTHER INFORMATION: Description of Artificial Sequence: Primer

<400> SEQUENCE: 69
accgcctcca ccagtgcact taattttatg ctgactcagc ccca        44

<210> SEQ ID NO 70
<211> LENGTH: 41
<212> TYPE: DNA
<213> ORGANISM: Artificial Sequence
<220> FEATURE:
<223> OTHER INFORMATION: Description of Artificial Sequence: Primer

<400> SEQUENCE: 70
accgcctcca ccagtgcaca grctgtggtg acycaggagc c           41

<210> SEQ ID NO 71
<211> LENGTH: 41
<212> TYPE: DNA
<213> ORGANISM: Artificial Sequence
<220> FEATURE:
<223> OTHER INFORMATION: Description of Artificial Sequence: Primer

<400> SEQUENCE: 71
accgcctcca ccagtgcacw gcctgtgctg actcagccmc c           41
```